US011033233B2

(12) United States Patent
Hayes et al.

(10) Patent No.: US 11,033,233 B2
(45) Date of Patent: Jun. 15, 2021

(54) PATIENT SUPPORT APPARATUS WITH PATIENT INFORMATION SENSORS

(71) Applicant: Stryker Corporation, Kalamazoo, MI (US)

(72) Inventors: Michael Joseph Hayes, Kalamazoo, MI (US); David Terrance Becker, Grand Rapids, MI (US); Annie Désaulniers, Redmond, WA (US); Aaron Douglas Furman, Kalamazoo, MI (US); Brandon J. Buckingham, Middleville, MI (US); Michael W. Steffler, Kalamazoo, MI (US); Richard A. Derenne, Portage, MI (US); Joshua Elmer Mix, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 16/529,482

(22) Filed: Aug. 1, 2019

(65) Prior Publication Data

US 2019/0350529 A1    Nov. 21, 2019

Related U.S. Application Data

(63) Continuation of application No. 14/776,842, filed as application No. PCT/US2014/026030 on Mar. 13, 2014, now Pat. No. 10,376,214.

(Continued)

(51) Int. Cl.
*A61B 5/00* (2006.01)
*A61B 5/117* (2016.01)
(Continued)

(52) U.S. Cl.
CPC ............ *A61B 5/6891* (2013.01); *A61B 5/002* (2013.01); *A61B 5/024* (2013.01); *A61B 5/0816* (2013.01);
(Continued)

(58) Field of Classification Search
CPC .... A61B 2562/0247; A61B 2562/0252; A61B 5/002; A61B 5/0024; A61B 5/0205;
(Continued)

(56) References Cited

U.S. PATENT DOCUMENTS

| 4,869,266 A * | 9/1989 | Taylor ..................... A61M 1/00 600/587 |
| 6,516,221 B1 * | 2/2003 | Hirouchi ............... A61B 5/0537 600/547 |
| 2002/0138905 A1 * | 10/2002 | Bartlett ................ A61G 7/0513 5/607 |

* cited by examiner

*Primary Examiner* — Niketa I Patel
*Assistant Examiner* — Vynn V Huh
(74) *Attorney, Agent, or Firm* — Warner Norcross + Judd LLP

(57) ABSTRACT

A person support apparatus includes sensors for monitoring aspects of a person positioned thereon. The outputs from the sensors are used to distinguish between new and prior occupants of the support apparatus, automatically zero an integrated scale system, distinguish between objects and humans on the support apparatus, determine if a person is sleeping or awake, monitor and characterize movement levels of the person, record a log of likely events regarding a support surface of the apparatus, propose identifications of objects added to or removed from the support surface, record force outputs, and/or other purposes. A person's sleep state may also be obtained and forwarded to a remote location. The sleep state data may be used to mute and/or control alerts or indicators, and/or to predict when a person is going to wake up and likely exit the support apparatus.

20 Claims, 23 Drawing Sheets

Related U.S. Application Data

(60) Provisional application No. 61/932,574, filed on Jan. 28, 2014, provisional application No. 61/881,581, filed on Sep. 24, 2013, provisional application No. 61/791,117, filed on Mar. 15, 2013.

(51) Int. Cl.
| | |
|---|---|
| *G16H 40/63* | (2018.01) |
| *A61G 7/05* | (2006.01) |
| *A61B 5/11* | (2006.01) |
| *A61B 5/024* | (2006.01) |
| *A61B 5/08* | (2006.01) |
| *A61G 7/00* | (2006.01) |
| *A61G 7/005* | (2006.01) |
| *A61G 7/008* | (2006.01) |
| *A61G 7/015* | (2006.01) |
| *A61G 7/018* | (2006.01) |
| *A61G 7/057* | (2006.01) |
| *G01G 19/44* | (2006.01) |
| *A61B 5/0205* | (2006.01) |

(52) U.S. Cl.
CPC ............. *A61B 5/117* (2013.01); *A61B 5/1115* (2013.01); *A61B 5/1118* (2013.01); *A61B 5/4809* (2013.01); *A61B 5/4812* (2013.01); *A61B 5/7275* (2013.01); *A61B 5/746* (2013.01); *A61B 5/7435* (2013.01); *A61G 7/00* (2013.01); *A61G 7/005* (2013.01); *A61G 7/008* (2013.01); *A61G 7/015* (2013.01); *A61G 7/018* (2013.01); *A61G 7/0509* (2016.11); *A61G 7/0514* (2016.11); *A61G 7/0524* (2016.11); *A61G 7/0527* (2016.11); *A61G 7/05776* (2013.01); *G16H 40/63* (2018.01); *A61B 5/0024* (2013.01); *A61B 5/0205* (2013.01); *A61B 5/6892* (2013.01); *A61B 2562/0247* (2013.01); *A61B 2562/0252* (2013.01); *A61G 2203/30* (2013.01); *A61G 2203/32* (2013.01); *A61G 2203/34* (2013.01); *G01G 19/445* (2013.01)

(58) Field of Classification Search
CPC ..... A61B 5/024; A61B 5/0816; A61B 5/1115; A61B 5/1118; A61B 5/117; A61B 5/4809; A61B 5/4812; A61B 5/6891; A61B 5/6892; A61B 5/7275; A61B 5/7435; A61B 5/746; A61G 2203/30; A61G 2203/32; A61G 2203/34; A61G 7/00; A61G 7/005; A61G 7/008; A61G 7/015; A61G 7/018; A61G 7/0509; A61G 7/0514; A61G 7/0524; A61G 7/0527; A61G 7/05776; G01G 19/445; G16H 40/63

See application file for complete search history.

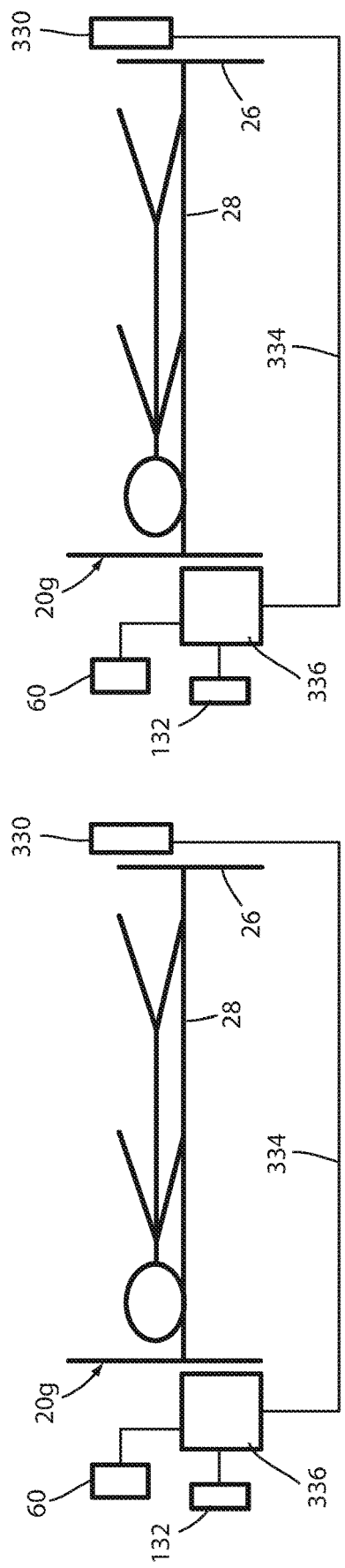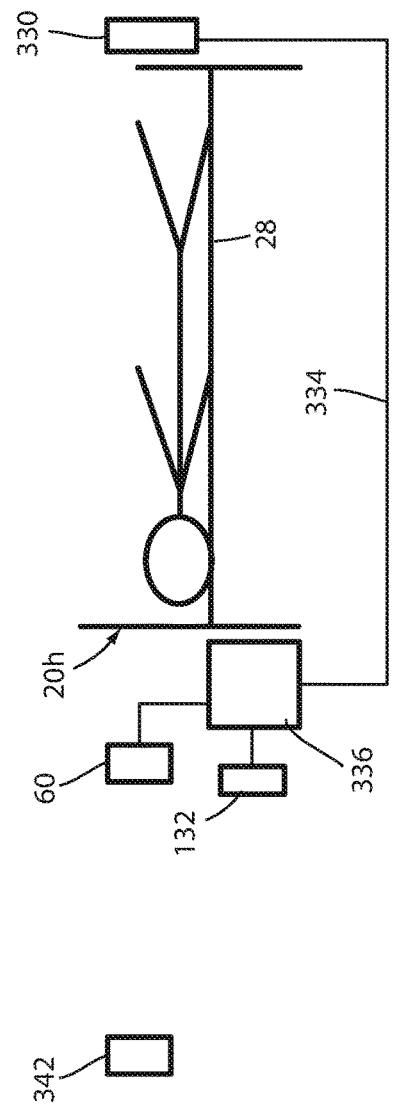
FIG. 27
FIG. 28

PATIENT SUPPORT APPARATUS WITH PATIENT INFORMATION SENSORS

CROSS-REFERENCE TO RELATED APPLICATIONS

This application claims priority to U.S. patent application Ser. No. 14/776,842, filed Sep. 15, 2015, by Joshua Mix et al. and entitled PATIENT SUPPORT APPARATUS WITH PATIENT INFORMATION SENSORS, which is a national stage entry of PCT/2014/026030, filed Mar. 13, 2014 and which claims priority to the following three U.S. provisional patent applications: Ser. No. 61/791,117 filed Mar. 15, 2013 by applicants Michael Hayes et al. and entitled PATIENT SUPPORT APPARATUS WITH PATIENT INFORMATION SENSORS; Ser. No. 61/881,581 filed Sep. 24, 2013 by applicants Joshua Mix et al. and entitled PATIENT SUPPORT APPARATUS; and Ser. No. 61/932,574 filed Jan. 28, 2014 by applicant Annie Desaulniers and entitled SYSTEM AND METHODS OF MANAGING AURAL AND/OR VISUAL INDICATIONS; the complete disclosures of all of which are hereby incorporated herein by reference.

BACKGROUND

The present invention relates to patient support apparatuses, such as beds, stretchers, cots, recliners, operating tables, and the like.

SUMMARY OF THE INVENTION

The various embodiments of the present invention provide improved patient support apparatuses that, in some embodiments, provide improved functionality, ease of use, and/or new or improved features. The improved patient support apparatuses include a plurality of patient information sensors that are able to sense information about patients or objects positioned on a support surface of the patient support apparatus. Such patient information sensors include force sensors adapted to detect downward forces exerted on the patient support apparatus by the patient and/or objects, as well as other patient information sensors. The outputs from the patient information sensors are used, either alone or in combination with other signals, to perform any one or more of the following, depending upon the various embodiments: distinguishing between new and old patients entering onto the support surface; automatically zeroing a scale system on the support apparatus; distinguishing between objects and humans positioned on the support surface; determining if a patient is sleeping or awake; monitoring and characterizing movement levels of the patient; recording for subsequent display a log of likely events regarding the support surface; proposing identifications of objects added to or removed from the support surface; automatically re-arming a patient exit alert system; recording force outputs prior to and during a patient exit from the support apparatus; and transmitting the recorded force outputs to a remote location.

In some embodiments, real time, or near real time, monitoring of weight readings are taken, recorded, analyzed, and the results of the analysis are made available for display to a caregiver, or forwarded to a healthcare computer network where they may be used by other applications or servers (e.g. an electronic medical records server). The patient information sensor may also be used to help ensure that a caregiver is more likely to be available for assisting a patient out of bed prior to the patient's actual departure, and/or also help ensure that the quality of a patient's time in a health care facility is improved through fewer interruptions in the patient's sleep.

In still other embodiments, systems and methods are provided for controlling the manner in which a device that emits aural and/or visual indications is controlled so that the aural and/or visual indications may take into account the sleep status of one or more individuals.

According to one aspect, a patient support apparatus is provided that includes a base, a frame supported on the base, a support surface, a plurality of force sensors, and a controller. The support surface is adapted to support a patient thereon, and the plurality of force sensors are coupled to the frame and adapted to output signals corresponding to downward forces exerted on the support surface. The controller is in communication with the plurality of force sensors and adapted to analyze the signals to determine if the signals are indicative of a prior patient having re-entered onto the support surface, or a new patient having entered on the support surface.

According to other aspects, the patient support apparatus includes a user interface in communication with the controller, wherein the controller provides an indication to a caregiver via the user interface when the controller determines that the signals are indicative of a new patient having entered onto the support surface. The user interface may be configured to prompt the caregiver to confirm or reject that the new patient did in fact enter onto the support surface.

A vital signs sensor is positioned on the patient support apparatus in some embodiments. The vital sign sensor detects a vital sign of a patient when the patient is supported on the support surface. The controller communicates with the vital sign sensor and uses outputs from the vital sign sensor in determining if the signals are indicative of the prior patient or the new patient having entered onto the support surface. The vital sign sensor may be incorporated into a pressure sensing mat positioned on the support surface wherein the pressure sensing mat includes an array of pressure sensors that able to detect at least one vital sign of a patient supported on the support surface. In addition, or alternatively, the vital sign sensor may comprise an air pressure sensor adapted to detect changes in air pressure within an inflatable bladder contained within a mattress supported on the support surface. The vital sign sensor is adapted to detect a patient's heart rate and/or respiration rate, although other vital signs may additionally or alternatively be detected.

In other aspects, when the controller determines that the signals are indicative of a new patient having entered onto the support surface, the controller prompts the caregiver to confirm or reject that a new patient did in fact enter onto the support surface. The prompting takes place in conjunction with a user interface on the patient support apparatus, which may include a display. The controller is further adapted to prompt a caregiver—when a new patient is detected—to clear any old data stored in a memory on the patient support apparatus relating to the prior patient, and to enter new data relating to the new patient. The new data includes any one or more of the following: a height of the new patient, a weight of the new patient, a name of the new patient, a fall risk assessment of the new patient, a bed sore assessment of the new patient, a turn protocol for the new patient, an alert setting for the new patient, a body-mass index for the new patient, or an infection risk assessment for the new patient.

In other aspects, the force sensors repetitively output signals corresponding to the downward forces and the controller uses the repetitively output signals to establish a baseline level of forces. The controller determines that the signals are indicative of the prior patient having entered onto the support surface if the signals exceed the baseline level of forces by an amount substantially equal to a previously stored weight of the prior patient. If the signals exceed the baseline level of forces by an amount that is different from the previously stored weight of the patient by more than a threshold value, the controller determines that a new patient has entered the patient support apparatus.

In some aspects, the plurality of force sensors repetitively output signals corresponding to the downward forces, and the controller uses the repetitively output signals to establish a baseline level of forces. The controller determines that the signals are indicative of a new patient having entered onto the support surface only if both (a) the signals exceed the baseline level of forces by an amount not substantially equal to a previously stored weight of the prior patient, and (b) the vital sign sensor is able to detect a vital sign of a patient positioned on the support surface.

The controller records a time when signals indicative of either the new patient or the prior patient having entered onto the support surface are detected, in some embodiments. In other embodiments, the controller records the signals over a time period prior to detecting the signals indicative of either the prior patient or the new patient having entered onto the support surface, determines a baseline level of forces from the signals recorded over the time period, and allows a caregiver to accept the baseline level of forces as a tare weight.

The controller may further analyze the signals to determine if the signals are indicative of a non-human object placed on the support surface. The controller may further propose an identification of the non-human object based at least partially upon the signals from the force sensors, and the controller may prompt the caregiver to confirm or reject the proposed identification of the non-human object.

An exit alert system can be coupled to the patient support apparatus and adapted to issue an alert if a patient on the support surface moves beyond a threshold amount while the exit alert system is armed. When included, the controller is adapted to automatically re-enable the exit alert system if the signals are indicative of the prior patient having re-entered the support surface and the patient exit alert system was previously armed.

According to another embodiment, a patient support apparatus is provided that includes a base, a frame supported on the base, a support surface, a plurality of force sensors, and a controller. The support surface is adapted to support a patient thereon. The force sensors are coupled to the frame and adapted to output signals corresponding to downward forces exerted on the support surface. The controller is in communication with the plurality of force sensors and adapted to record outputs from the plurality of force sensors over time, to determine if a likely event with respect to the support surface has occurred, and to prompt a caregiver to confirm or reject that the likely event has actually occurred.

In other aspects, the likely event includes any one or more of the following: (a) a new patient has entered the support surface, (b) a prior patient has re-entered the support surface; (c) a non-human object has been placed on the support surface, (d) a person has or is leaning on the support surface, and (e) a non-human object has been removed from the patient support apparatus.

The controller may be adapted to time stamp each likely event and to display a time corresponding to each likely event when prompting the caregiver to confirm or reject that the likely event has actually occurred.

In another embodiment, the controller determines a baseline weight sensed by the sensors prior to the likely event, determines a second weight sensed by the sensors after the likely event, and displays a difference between the baseline weight and the second weight on a display supported on the patient support apparatus. The controller uses the difference between the baseline weight and the second weight to characterize the likely event and display the characterization. The controller prompts a caregiver to accept or reject the displayed characterization. The characterization includes any one or more of the following: (a) a new patient has entered the support surface, (b) a prior patient has re-entered the support surface; (c) a non-human object has been placed on the support surface, (d) a person has or is leaning on the support surface, and (e) a non-human object has been removed from the patient support apparatus. If the controller characterizes the likely event as one of (c) or (e), the controller uses the difference between the baseline weight and the second weight to display a potential identification of the non-human object. The controller prompts the caregiver to accept or reject the displayed possible identification of the non-human object.

According to other aspects, the controller uses at least one vital sign detected by the force sensors to characterize the likely event and display the characterization. If the controller detects either a cessation or a commencement of vital sign signals, the controller determines that the signals from the plurality of force sensors are likely indicative of a human moving onto or off the patient support surface.

According to another embodiment, a patient support apparatus is provided that includes a base, a frame supported on the base, a patient support surface, a plurality of force sensors, and a controller in communication with the plurality of force sensors. The force sensors are coupled to the frame and adapted to output signals corresponding to downward forces exerted on the support surface. The controller monitors the signals from the plurality of force sensors and analyzes the signals to determine if the signals are indicative of a non-human object moving onto or off the support surface.

In other aspects, the controller generates a proposed identification of the non-human object and displays the proposed identification on a display coupled to the controller. The proposed identification is based upon a change in weight detected by the plurality of force sensors before and after the non-human object is moved onto or off of the support surface. The controller is further adapted to use the display to prompt a caregiver to accept or reject the proposed identification of the non-human object. The proposed identification of the non-human object includes at least one of a medical device, bedding, and a pillow. The proposed identification of the medical device includes, in at least one embodiment, an identification of a ventilator and a pump.

The plurality of force sensors may be load cells integrated into the patient support apparatus.

According to yet another embodiment, a patient support apparatus is provided that includes a base, a frame, a support surface, a plurality of force sensors, a display, and a controller. The plurality of force sensors are coupled to the frame and adapted to output signals corresponding to downward forces exerted on the support surface. The controller is in communication with the plurality of force sensors and the display, and the controller is adapted to categorize changes in the outputs and to record a time when each of the categorized changes occurs. The controller is further adapted to display information relating to the categorized changes on the display.

According to still another embodiment, a patient support apparatus is provided that includes a base, a frame, a support surface, a plurality of force sensors, a display, and a controller. The plurality of force sensors are coupled to the frame and adapted to output signals corresponding to downward forces exerted on the support surface. The controller is in communication with the plurality of force sensors and the display, and the controller is adapted use the signals from the plurality of force sensors to propose on the display an identification of a non-human object moving onto or off the support surface.

According to another embodiment, a patient support apparatus is provided that includes a base, a frame, a support surface, a vital sign sensor, an exit alert system, and a controller. The vital sign sensor is supported on the frame and is adapted to output signals corresponding to a vital sign of a patient supported on the support surface. The exit alert system is coupled to the patient support apparatus, and the exit alert system is adapted to issue an alert if a patient on the support surface moves beyond a threshold amount while the exit alert system is armed. The controller is in communication with the vital sign sensor and adapted to use the signals from the vital sign sensor in determining whether to automatically re-arm the exit alert system after the exit alert system has been disarmed.

According to other aspects, the vital sign sensor may include a plurality of force sensors coupled to the frame and adapted to output signals corresponding to downward forces exerted on the support surface. The force sensors may be load cells. The load cells may be integrated into a scale system adapted to measure a weight of a patient positioned on the support surface. Still further, the exit alert system may use the same, or at least some common, components as those of the vital sign sensor. In other embodiments, the vital sign sensor is a fluid pressure sensor positioned inside an inflatable bladder contained within a mattress supported on the support surface. The fluid pressure sensor detects changes in air pressure inside the inflatable bladder corresponding to one or both of a patient's heart rate or respiration rate.

According to another embodiment, a patient support apparatus is provided that includes a base, a frame, a support surface, a scale system, and a controller. The scale system includes a plurality of force sensors coupled to the frame and adapted to output signals corresponding to weight exerted on the support surface. The controller communicates with the scale system and is adapted to automatically record a weight sensed by the scale system prior to a patient entering the support surface and to allow a caregiver to accept the recorded weight as a tare weight.

The controller may be further adapted to display the recorded weight on a display coupled to the patient support apparatus. The controller may prompt the caregiver to accept or reject the recorded weight as a tare weight. If the caregiver accepts the recorded weight as a tare weight, the controller subtracts the tare weight from a weight reading taken after the patient enters onto the support surface. A user interface may be provided that allows a caregiver to view the recorded weight even after the caregiver accepts the recorded weight as the tare weight.

According to still another embodiment, a patient support apparatus is provided that includes a base, a frame, a support surface, a plurality of force sensors, a display, and a controller. The plurality of force sensors are coupled to the frame and adapted to output signals corresponding to downward forces exerted on the support surface. The controller is in communication with the plurality of force sensors and the display, and the controller is adapted to classify the signals from the plurality of force sensors into a plurality of different levels of movement by a patient supported on the support surface. The controller further displays the different levels of movement on the display.

The controller may further record a duration of each of the plurality of different levels of movement and display them on the display. The levels of movement may include a high level of activity, a moderate level of activity, and a low level of activity, as well as other levels of activity. The controller is further able to record starting and ending times for each of the plurality of different levels of movement. The recorded starting and ending times are displayable on the display.

The controller can also be configured to calculate a cumulative amount of time a patient spends engaging in each of the plurality of levels of movement. One level of movement may correspond to the patient being asleep.

One or more vital sign sensors may also be included that, in conjunction with the plurality of force sensors, are used by the controller to classify whether a patient supported on the patient support apparatus is sleeping or not. The vital sign sensors include sensors that detect a patient's respiration rate and/or heart rate. The vital sign sensors may utilize the plurality of force sensors, and/or the vital sign sensors may be incorporated into a mattress supported on the support surface. As yet another alternative, the vital sign sensor may be incorporated into a flexible pressure sensing mat having an array of pressure sensors, wherein the pressure sensing mat is positioned between the support surface and a patient supported thereon, and the pressure sensing mat is in communication with the controller.

The controller may further be adapted to issue an alert regarding potential bed sore development if the patient remains at a low level of movement for more than a predetermined amount of time. The controller allows the caregiver to select the predetermined amount of time. The controller further records cumulative durations of time for each of the plurality of different levels of movement and allows a caregiver to select a range of time over which to display the cumulative durations.

According to yet another embodiment, a patient support apparatus is provided that includes a base, a frame, a support surface, a plurality of force sensors, and a controller. The plurality of force sensors are coupled to the frame and adapted to output signals corresponding to downward forces exerted on the support surface. The controller is in communication with the plurality of force sensors and adapted to use the signals from the plurality of force sensors to estimate whether a patient supported on the support surface is asleep or not.

In some embodiments, the plurality of force sensors include a plurality of load cells that are incorporated into a scale system, and the scale system is adapted to determine both a level of movement of the patient positioned on the support surface, and at least one vital sign of the patient positioned on the support surface. The at least one vital sign includes a patient's respiration rate and/or heart rate. The controller may be configured to use both the level of movement of the patient and the vital sign when estimating whether the patient supported on the support surface is asleep or not.

According to another embodiment, a patient support apparatus is provided that includes a base, a frame, a support surface, an exit alert system, and a controller. The exit alert system is adapted to issue an alert if a patient on the support surface either completely exits the patient support, or otherwise makes initial movements toward exiting the bed while the exit alert system is armed. The controller is in communication with the exit alert system and adapted to record a time when a patient positioned on the support surface exits the support surface, or otherwise triggers the exit alert system, regardless of whether or not the exit alert system is armed or not.

A display may be included that is in communication with the controller, and the controller may be adapted to display the time when the patient positioned on the support surface exited the patient support. The controller may further be adapted to record how long the patient remains off the support surface after exiting the support surface. The exit alert system may include a plurality of force sensors adapted to detect downward forces exerted on the support surface. The force sensors may comprise load cells integrated into the patient support apparatus. The controller, in some embodiments, is adapted to record outputs of the load cells prior to, and during, the exiting of the patient from the support surface. The recorded outputs are stored for transmission to a location remote from the patient support apparatus for analysis. Alternatively, or additionally, the controller is able to use the recorded outputs of the load cells to analyze future outputs of the load cells. Such analysis may include analyzing future outputs of the load cells for similarities to the recorded outputs. Such analysis may also involve looking for patterns in the recorded outputs and using any discovered patterns to analyze future outputs of the load cells in order to predict when a patient may be about to exit the patient support apparatus. Such prediction may occur prior to an alert being triggered by the exit alert system.

According to another embodiment, a patient support apparatus is provided that includes a base, a frame, a support surface, an exit alert system, and a controller. The exit alert system is adapted to issue an alert if a patient on the support surface moves beyond a threshold amount while the exit alert system is armed. The exit alert system includes a plurality of force sensors coupled to the frame and adapted to output signals corresponding to downward forces exerted on the support surface. The controller is in communication with the plurality of force sensors and the transceiver, and the controller records outputs from the force sensors when a patient exits the support surface and transmits the recorded outputs to a remote location, regardless of whether or not the exit alert system is armed.

The transmission of the recorded outputs to the remote location may take place wirelessly via a WiFi link (IEEE 802.11). The controller may record outputs from the force sensors both prior to, and during, the patient exit, and such recordings may be transmitted to the remote location. The plurality of force sensors may be adapted to measure a weight of a patient positioned on the support surface, and/or the plurality of force sensors may be load cells. The controller may be further adapted to receive instructions from the remote location to modify the exit alert system in a manner that is based at least partially upon the recorded outputs transmitted to the remote location.

According to yet another embodiment, a patient support apparatus is provided that includes a base, a frame, a support surface, a plurality of force sensors, and a controller. The plurality of force sensors are coupled to the frame and adapted to output signals corresponding to downward forces exerted on the support surface. The controller is in communication with the plurality of force sensors, and the controller is adapted to use the signals from the plurality of force sensors to estimate whether a patient supported on the support surface has turned or not.

According to other aspects, the controller records a time at which each turn is estimated to have occurred, as well as a duration of time between each turn. The controller may also determine which way a patient has turned, such as, but not limited to, from the patient's back to the patient's right side, from the patient's back to the patient's left side, from the patient's left side to the back, from the patient's right side to the back, and/or from one of the patient's right or left sides to the other of the patient's right or left sides.

According to yet another embodiment, a patient support apparatus is provided that includes a base, a frame, a support surface, a scale system, a user interface, and a controller. The scale system is coupled to the frame and adapted to output weight signals corresponding to weight exerted on the support surface. The user interface allows a caregiver to use the scale system to weigh a patient positioned on the support surface. The controller is in communication with the scale system and the user interface, and the controller is adapted to use the weight signals to automatically record a first weight prior to a patient entering onto the support surface so that a patient weight may be determined by subtracting the first weight from a second weight recorded after a patient has entered onto the support surface.

A display may further be included that is adapted to display any one or more of the first weight, second weight, and/or patient weight.

According to another embodiment, a patient support apparatus is provided that includes a frame, a support surface that is able to support a patient thereon, a vital sign sensor, and a controller. The vital sign sensor is supported by the frame and is adapted to detect at least one vital sign of a patient supported on the support surface. The controller is in communication with the vital sign sensor and adapted to analyze data from the vital sign sensor to predict if the patient supported on the support surface is likely to exit from the patient support apparatus.

The controller issues an alert when it predicts that the patient is likely to exit from the patient support apparatus.

In some embodiments, the patient support apparatus includes a siderail to which the vital sign sensor is coupled. Still further, in some embodiments, multiple vital sign sensors are included on the patient support apparatus, including one in a first siderail located on a first side of the patient support apparatus and one in a second siderail located on a second side opposite the first side.

The vital sign sensor may take on a variety of different forms. In one embodiment, the vital sign sensor emits a radio frequency signal toward the patient supported on the support surface and detects reflections from the patient's torso to determine a breathing rate and/or a heart rate of the patient. In another embodiment, the vital sign sensor emits an ultrasonic signal toward the patient supported on the support surface and detects reflections from the patient's torso to determine a breathing rate and/or a heart rate of the patient. In still another embodiment, the vital sign sensor includes a plurality of load cells adapted to provide support for the support surface and to detect mechanical vibrations caused by the patient's breathing and/or heart beating.

The controller may be in communication with a wireless transceiver positioned on board the patient support apparatus, wherein the controller sends a wireless message indicative of the patient's likely exit from the patient support apparatus to a remote network using the wireless transceiver. The wireless transceiver is, in at least one embodiment, a wireless transceiver that follows at least one of Institute of Electrical and Electronics Engineers (IEEE) standards 802.11(b), (g), or (n).

The controller may also be adapted to determine when a sleeping patient is likely to awaken prior to the patient actually awakening based upon the data from the vital sign sensor. When so configured, the controller issues an alert when it determines that the patient is likely to awaken. The controller may determine when the patient is likely to awaken by identifying accelerations in the patient's heart rate and/or breathing rate.

The controller may be adapted to issue an alert when the patient falls asleep or awakens. Such alert may be a local alert at or in the immediate vicinity of the patient support apparatus, or it may be a remote alert outside of the room in which the patient is located. When issuing a remote alert, the controller may communicate with a wireless transceiver positioned on board the patient support apparatus that sends a wireless message indicating the patient has awoken and/or fallen asleep to a remote network using the wireless transceiver. The wireless message may be forwarded to a software application adapted to wirelessly forward a notification of the wireless message to a mobile electronic device carried by a caregiver. The mobile electronic device may be a smart phone, computer laptop, computer netbook, computer tablet, personal digital assistant, or the like.

In some embodiments, the controller is further adapted to identify a plurality of sleep stages of the patient supported on the support surface and to record a duration of each of the plurality of sleep stages. The controller also communicates with a display to display the duration of each of the sleep stages. The controller may also be adapted to generate an assessment of a patient's sleep quality based upon the data from the vital sign sensor. The plurality of sleep stages includes REM (rapid eye movement) sleep, as well as other types of sleep.

The vital sign sensor used to determine the patient's sleep status may be incorporated into a siderail of the patient support apparatus. The vital sign sensor used to determine the patient's sleep status may be one that emits a radio frequency signal, or an ultrasonic signal, toward the patient supported on the support surface and detects reflections from the patient's torso to determine the breathing rate and/or heart rate of the patient. Alternatively, the vital sign sensor may include a plurality of load cells adapted to provide support for the support surface and to detect mechanical vibrations caused by at least one of the patient's breathing or heart beating.

In still other embodiments, the controller determines when the patient is likely to awaken prior to the patient actually awakening based upon the data from the vital sign sensor. The controller issues an alert when it determines that the patient is likely to awaken. The controller may determine when the patient is likely to awaken by identifying accelerations in the patient's heart rate and/or breathing rate.

In one embodiment, a person support apparatus is provided that includes a support surface, a vital sign sensor, an indicator, and a controller. The vital sign sensor is adapted to detect a vital sign of a person positioned on the support surface, and the indicator is adapted to emit a sound or visual signal in response to a triggering event. The controller is in communication with the vital sign sensor and the indicator, and is use the vital sign sensor to determine a sleep state of the person positioned on the support surface and to control the indicator based upon the determined sleep state.

In another embodiment, a person support apparatus is provided that includes a support surface, a vital sign sensor, an indicator, a sleep detector, and a user interface. The vital sign sensor detects a vital sign of a person positioned on the support surface and the sleep detector determines a sleep state of the person positioned on the support surface. The user interface is in communication with the sleep detector and the indicator, and the user interface is configured to allow a user to choose whether or not the indicator will emit a sound, produce a visual signal, or a combination of the two, when the person is asleep and a triggering event occurs.

In other embodiments, the controller categorizes the sleep state of the person into three or more sleep states, and the controller changes a characteristic of the indicator based upon the determined sleep state. The three or more states may include three or more of the following: awake, asleep, deep sleep, awakening, and/or falling asleep.

The controller may change the volume of the sound, and/or the intensity of light, emitted from the indicator based upon the determined sleep state, and the volume and/or lighting change may include a complete shut off, or a partial but not complete, reduction of the volume and/or intensity.

The vital sign sensor may include both a respiration sensor and a heart rate sensor wherein the respiration sensor is adapted to detect a respiration rate of the person positioned on the support surface, and the heart rate sensor is adapted to detect a heart rate of the person positioned on the support surface. In some embodiments, both the respiration sensor and the heart rate sensor both operate without making direct contact with the person supported on the support surface. Still further, the respiration and heart rate may be stored over time and compared with a current heart rate and current respiration rate in order to determine the sleep state of the person positioned on the person support apparatus.

In other embodiments, the controller is further adapted to forward a sleep status message indicative of the determined sleep state to a device separate from the person support apparatus. Such a device may be a nurse call system, a medical device, another person support apparatus, a mobile communication device (e.g. telephone, pager, smart phone, etc.), or other device.

In some embodiments, the person support apparatus is one of a bed and a stretcher, and the indicator is one or more of a buzzer, beeper, speaker, light bulb, and light emitting diode (LED). When implemented as a bed, the triggering event may include the expiration of a timer associated with medical care of the person supported on the support surface.

In some embodiments, the controller delays activation of the indicator if the controller determines that the sleep state is one of the person being asleep. The controller may alternatively lower the volume, or completely mute, the indicator's sound if the sleep state is one of the person being asleep. The indicator may be adapted to emit sound and/or light in response to multiple different triggering events. Still further, the user interface may be adapted to allow the user to select which of the multiple different triggering events will be affected by the sleep status of the person.

In other embodiments, the person support apparatus includes a user interface adapted to allow the user to select from multiple different options how the controller controls the indicator for the triggering events when the person is asleep. The user interface may also, or alternatively, be configured to allow the user to mute the indicator for a first one of the triggering events when the person is asleep, and to allow the indicator to emit the sound for a different one of the triggering events when the person is asleep. In this manner, aural alerts in response to lower priority triggering events may be muted while still retaining aural alerts for higher priority triggering events.

In still other embodiments, the controller receives a sleep status signal from a second person support apparatus indicative of a sleep status of a second person supported on the second person support apparatus, and the controller controls the indicator based at least partially upon the sleep status signal. In this manner, aural alerts from all person support apparatuses within a nearby vicinity of a sleeping person may be appropriately controlled, such as by muting or reducing their volume, when a person is asleep.

The user interface may allow the user to forward a signal to a remote device when the person is asleep and the triggering event occurs.

The sleep detector may further comprise a movement detector adapted to detect movement of the person supported on the support surface, wherein the sleep detector uses outputs from the movement detector in determining the sleep state of the person.

The person support apparatus may also include a second indicator coupled to the person support apparatus, wherein the user interface is configured to allow a user to choose whether or not the second indicator will emit a sound and/or light when the person is asleep and a second triggering event occurs different from the triggering event.

The controller may be adapted to forward a volume control signal to an electronic device having an audio output when the sleep detector determines that the person is asleep, wherein the volume control signal results in a change in a volume of sound emitted from the electronic device. The electronic device may be a cell phone, television, radio, computer, or other device.

In some embodiments, the controller is in communication with a room light and is adapted to forward a control signal to the room light to change an illumination state of the light. The controller may also, or alternatively, be adapted to forward a control signal to a telephone when the sleep detector determines that the person is asleep, wherein the control signal results in a change in how the telephone rings.

In any of the embodiments discussed herein, the person support apparatus may be one of a bed, a stretcher, a cot, a recliner, or an operating table. In still other embodiments, any of the concepts described herein may be incorporated into non-medical support apparatuses, such as, but not limited to, residential beds, hotel beds, home or office chairs or recliners, or other non-medical devices.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

FIG. 27 is a side elevational diagram of a plurality of person support apparatuses according to another embodiment;

FIG. 28 is a side elevational diagram of a person support apparatus according to yet another embodiment;

FIG. 29b is a continuation of the flow diagram of FIG. 29a.

DETAILED DESCRIPTION OF THE EMBODIMENTS

Figure 1:
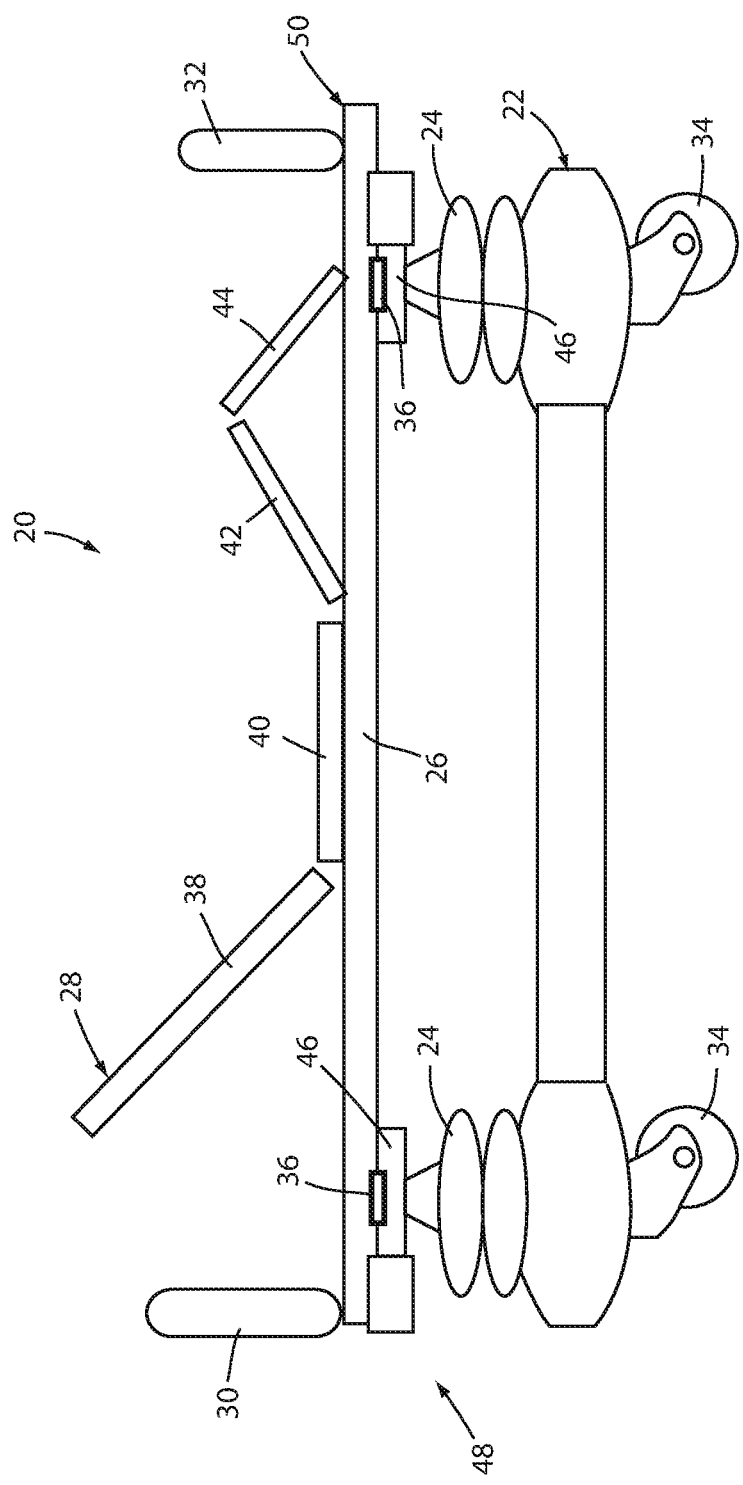
FIG. 1 is a side, elevational diagram of the physical construction of a patient support apparatus that may incorporate any one or more of the various features and functions described herein.

The inventive features and functions described herein are applicable to patient support apparatuses, such as beds, cots, stretchers, operating tables, recliners, and the like. FIG. 1 illustrates in diagrammatic form the general components that are commonly found in some of these patient support apparatuses, particularly when the support apparatuses are beds or stretchers. More particularly, FIG. 1 illustrates a patient support apparatus 20 that includes a base 22, a pair of elevation adjustment mechanisms 24, a frame or litter assembly 26, a patient support surface or deck 28, a headboard 30, and a footboard 32. Base 22 includes a plurality of wheels 34 that can be selectively locked and unlocked so that, when unlocked, patient support apparatus 20 is able to be wheeled to different locations. Elevation adjustment mechanisms 24 are adapted to raise and lower frame 26 with respect to base 22. Elevation adjustment mechanisms 24 may be hydraulic actuators, electric actuators, or any other suitable device for raising and lowering frame 26 with respect to base 22. In some embodiments, elevation adjustment mechanisms 24 operate independently so that the orientation of frame 26 with respect to base 22 may also be adjusted.

Frame 26 provides a structure for supporting patient support surface 28, headboard 30, and footboard 32. Patient support surface 28 provides a surface on which a mattress, or other soft cushion, is positionable so that a patient may lie and/or sit thereon. Patient support surface 28 is made of a plurality of sections, some of which are pivotable about generally horizontal pivot axes. In the embodiment shown in FIG. 1, patient support surface 28 includes a head section 38, a seat section 40, a thigh section 42, and a foot section 44. Head section 38, which is also sometimes referred to as a Fowler section, is pivotable between a generally horizontal orientation (not shown in FIG. 1) and a plurality of raised positions (one of which is shown in FIG. 1). Thigh section 42 and foot section 44 may also be pivotable, such as is shown in FIG. 1.

Patient support apparatus 20 further includes a plurality of load cells 36 positioned between an underside of frame 26 and support structures 46 coupled to elevation adjustment mechanism 24. While only two load cells 36 are visible in FIG. 1, patient support apparatus 20 includes four load cells, two positioned at a head end 48 of support apparatus 20 and another two positioned at a foot end 50 of support apparatus 20. Load cells 36 are any conventional load cells, or similar force measuring sensors, that are positioned to detect the amount of downward force exerted by patient support deck 28, and any objects, patient(s), and/or other persons that are exerting downward forces on support deck 28, whether due to gravity or due to other causes. The physical arrangement of load cells 36 is, in some embodiments, the same as that found in many conventional hospital beds. For example, in one embodiment, the position and physical construction of load cells 36 are the same as that found in the S3® bed sold by Stryker Corporation of Kalamazoo, Mich. These physical details are described in detail in the Stryker Maintenance Manual for Stryker's MedSurg Bed, Model 3002 S3, (doc. 3006-109-002 Rev D), published in 2010, the complete disclosure of which is hereby incorporated herein by reference.

Figure 2:
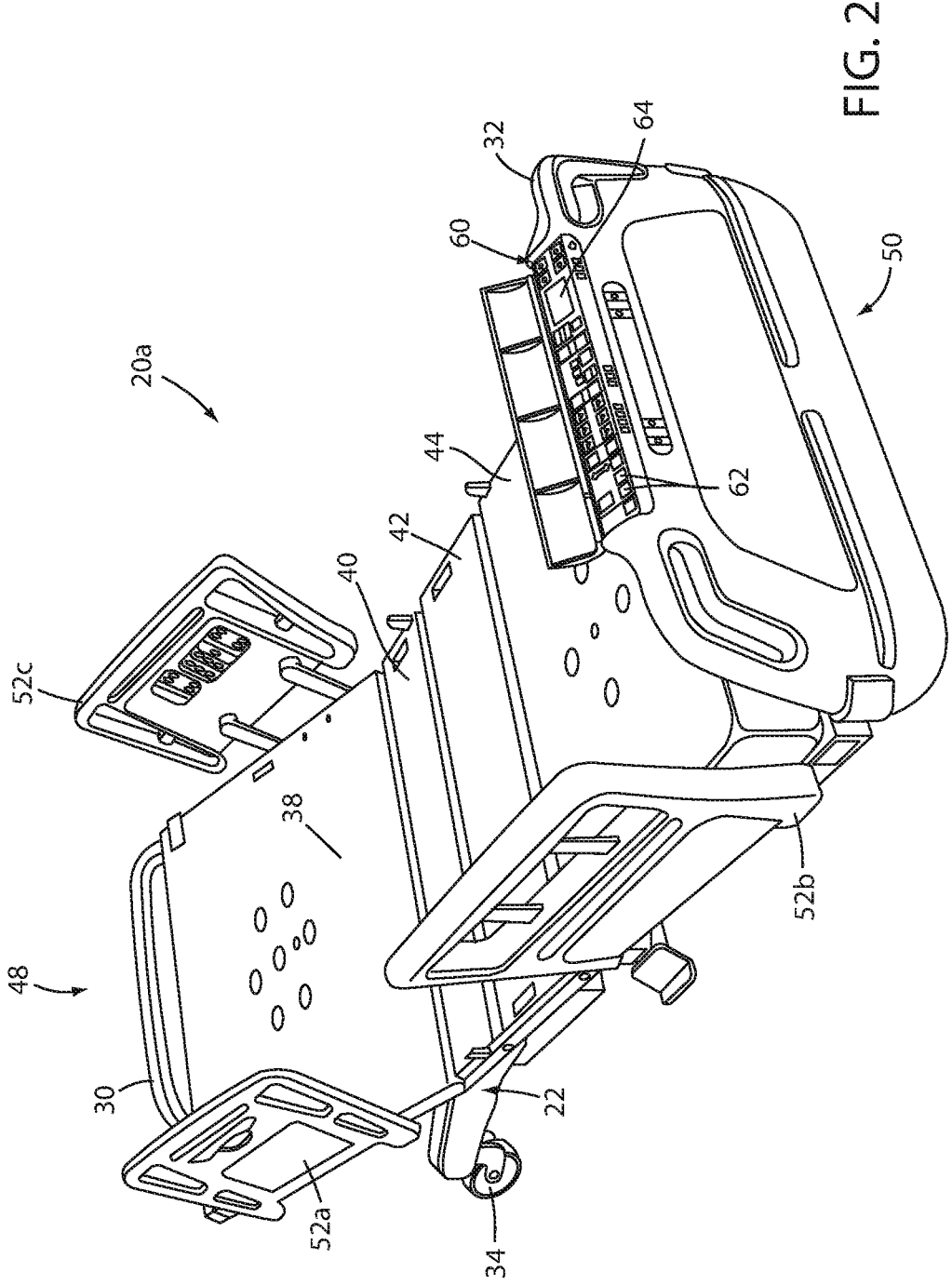
FIG. 2 is a perspective view of the physical construction of another patient support apparatus that may incorporate any one or more of the various features and functions described herein.

FIG. 2 illustrates another patient support apparatus 20a into which any of the inventive features or functions described are able to be incorporated. Patient support apparatus 20a, like support apparatus 20, includes a base 22 having a plurality of wheels 34, a frame 26 (not labeled), a pair of elevation adjustment mechanisms (not visible in FIG. 2), a support surface or deck 28, a headboard 30, and a footboard 32. Support surface 28 of patient support apparatus 20a, like that of support apparatus 20, includes four sections: a head section 38, a seat section 40, a thigh section 42, and a foot section 44. Patient support apparatus 20a, like support apparatus 20, also includes four load cells 36 (not shown) that are adapted to detect downward forces exerted by patients, other people, and/or objects on patient support surface 28.

In addition to the aforementioned components, patient support apparatus 20a includes four side rails: a right head side rail 52a, a right foot side rail 52b, a left head side rail 52c and a left foot side rail 52d (not shown). Side rails 52 are be movable between a raised position and a lowered position. In the configuration shown in FIG. 2, right head side rail 52a, right foot side rail 52b, and left head side rail 52c are shown in the raised position, while left foot side rail 52d (not visible) has been moved to the lowered position.

The physical construction of any of base 22, elevation adjustment mechanisms 24, frame 26, patient support surface 28, headboard 30, footboard 32, and/or side rails 52 may be the same as disclosed in commonly assigned, U.S. Pat. No. 7,690,059 issued to Lemire et al., and entitled HOSPITAL BED, the complete disclosure of which is incorporated herein by reference; or as disclosed in commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosure of which is also hereby incorporated herein by reference, or as disclosed in the aforementioned Stryker Maintenance Manual for the Model 3002 S3 MedSurg Bed, the disclosure of which was previously incorporated herein by reference. The construction of any of base 22, elevation adjustment mechanisms 24, frame 26, patient support surface 28, headboard 30, footboard 32 and/or side rails 52 may also take on forms different from what is disclosed in these documents.

Figure 3:
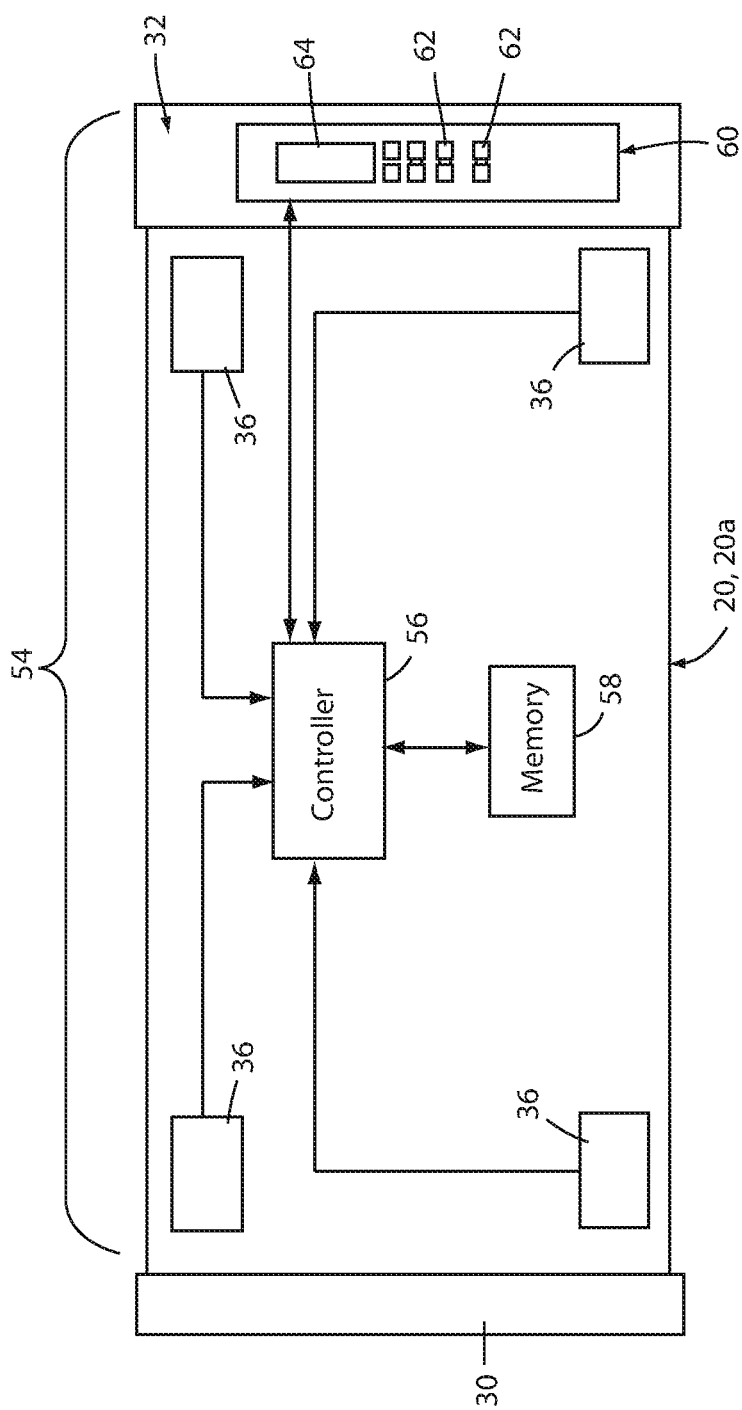
FIG. 3 is a plan view diagram of a measurement subsystem that may be incorporated into either of the patient support apparatuses of FIGS. 1 and 2.

FIG. 3 illustrates a plan view diagram of a patient support apparatus (20 or 20a) having a measurement subsystem 54. Measurement subsystem 54 may be incorporated into either or both of patient support apparatuses 20 and 20a in order to provide those patient support apparatuses with any of the features and functions described herein of measurement subsystem 54 (or the modified versions of subsystem 54 described below). Measurement subsystem 54 includes a controller 56, a memory 58 in communication with the controller 56, a user interface 60, a plurality of buttons 62, a display 64, and four force sensors or load cells 36.

The components of measurement subsystem 54 communicate with each other using conventional electronic communication techniques. In one embodiment, controller 56 communicates with memory 58, user interface 60, and load cells 36 using I-squared-C communications. Other types of serial or parallel communication can alternatively be used. In some other embodiments, different methods may be used for different components. For example, in one embodiment, controller 56 communicates with user interface 60 via a controller area network or LIN, while it communicates with memory 58 and load cells 36 using I squared C. Still other variations are possible.

User interface 60 includes a plurality of buttons 62 that a caregiver presses in order to control various features of the patient support apparatus, such as, but not limited to, raising and lowering the height of frame 26, pivoting one or more of support surface sections 28, turning on and off a brake (not shown), controlling a scale system integrated into the patient support apparatus, controlling an exit alert system integrated into the support apparatus 20 or 20a, and/or controlling other features of the patient support apparatus 20 or 20a. User interface 60 further includes display 64 integrated therein. Display 64 is a touchscreen display capable of displaying text and/or graphics and sensing the location where a user's finger touches the display, although it will be understood that display 64 could be modified to be a normal LCD display without touchscreen capabilities that uses hard or soft buttons to interact therewith, or still other types of displays.

Controller 56 includes a microcontroller that is programmed to carry out the functions described herein. It will be understood that controller 56 may be varied to include other electronic components that are programmed to carry out the functions described herein, such as, but not limited to, one or more microprocessors, microcontrollers, field programmable gate arrays, systems on a chip, volatile or nonvolatile memory, discrete circuitry, and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units.

Controller 56 is in communication with each of four load cells 36 and receives the outputs from load cells 36. Load cells 36 are positioned adjacent each corner of the patient support surface 28 and cumulatively sense the entire weight of a patient, other person, and/or objects positioned on the patient support surface 28. In one arrangement, the load cells are positioned such that one load cell 36 is positioned adjacent each corner of a load frame (not shown), and the load cells 36 detect forces exerted by a patient support frame upon the load frame (through the load cells). While the construction of the load frame and patient support frame may vary, one example is disclosed in the commonly assigned U.S. Pat. No. 7,690,059 mentioned above and incorporated herein by reference. Another example is disclosed in the Stryker Maintenance Manual for the Model 3002 S3 MedSurg Bed, which has also already been incorporated herein by reference. Other constructions of the frames and positions of the load cells may also be used.

Measurement subsystem 54 is capable of performing a variety of different functions. In some embodiments, measurement subsystem 54 is used to detect whether a patient has exited the patient support apparatus 20 or 20a, or is about to exit the patient support apparatus. One manner in which measurement subsystem 54 is able to use the load cells 36 to determine patient exit, or potential patient exit, is disclosed in commonly assigned, U.S. Pat. No. 5,276,432 issued to Travis and entitled PATIENT EXIT DETECTION MECHANISM FOR HOSPITAL BED, the complete disclosure of which is also hereby incorporated herein by reference. Other methods for using the load cells to determine patient bed exit may also be used. In the method disclosed in the U.S. Pat. No. 5,276,432, the force sensed by each load cell is determined and used, in combination with the location of each load cell, to determine the center of gravity of the forces exerted on the load cells. If the center of gravity of the forces is within a predefined region, no patient exit is presumed. If the center of gravity moves outside of a predefined region, a patient exit is presumed, and an alarm issues on the patient support apparatus 20, 20a, and/or at a remote location in communication with patient the support apparatus 20, 20a, such as a nurses' station. In some embodiments, there are multiple predefined regions, and a caregiver may be able to select which region the center of gravity has to move outside of in order to cause a patient exit alert to issue.

In addition to determining whether a patient has exited the patient support apparatus 20, 20a, or may be about to exit the patient support apparatus 20, 20a, measurement subsystem 54 is also able to determine a weight of a patient positioned on patient support apparatus 20 or 20a. Such weight measurements are based upon a summation of the total forces sensed by the load cells 48, minus the weight of the non-patient objects that exert a force on the load cells.

In the embodiment shown in FIG. 3, measurement subsystem 54 is configured to always remain on while the electrical system of the patient support apparatus 20, 20a is turned on. In other embodiments, subsystem 54 is automatically activated based upon other events, such as the brake being turned on, an electrical cord being plugged into an electrical wall outlet, or another event. By always remaining on, or substantially always remaining on, measurement subsystem 54 is able to continuously monitor the weight sensed by load cells 36. The continuous weight readings taken by measurement subsystem 54 are stored in memory 58 and used for one or more of the purposes discussed in greater detail below. Memory 58 is any conventional electronic memory that is non-volatile, such as one or more EEPROMs, flash memory, or other suitable memory.

By having measurement subsystem 54 remain always on, or substantially always on, it is highly likely that weight readings will be taken by controller 56 prior to a patient entering the patient support apparatus 20, 20a. Measurement subsystem 54 therefore captures the weight detected by load cells 36 both prior to a patient entering patient support surface 28 and after the patient is positioned thereon. By capturing both of these weights, measurement subsystem 54 is able to determine the weight of the patient by subtracting the weight (if any) sensed by load cells 36 prior to the patient entering onto the support surface 28 from the weight sensed by load cells 36 after the patient has entered the support surface 28. This difference is equal to the patient's weight. Further, because the weight sensed by load cells 36 prior to the patient entering onto support surface 28 is known, the caregiver does not need to zero measurement system 54 prior to the patient entering onto patient support surface 28, as was required in many instances in the past.

In other words, in many past patient support apparatuses, if a patient entered onto the patient support surface prior to the caregiver zeroing the system, the subsequent weight reading would include whatever weight the patient was exerting on patient support surface, plus whatever weight was previously being exerted on the support surface (e.g. mattress, pillows, blankets). The weight reading would therefore be inaccurate with respect to the patient, and the patient would have to be removed to zero the system. Thereafter, the patient would re-enter the patient support surface and an accurate weight reading could be taken.

Measurement system 54 therefore eliminates the need for any manual zeroing of its weight measurement function. That is, one of the features that is able to be incorporated into measurement subsystem 54 is an auto-zeroing function for the scale system. By measuring the outputs of the load cells 36 nearly continuously, measurement subsystem 54 is able to determine a baseline weight sensed by load cells 36 prior to the patient entering, and then subtract this baseline weight from the weight measured after the patient enters the patient support apparatus 20, 20a, thereby avoiding the need to manually zero the weight scale system prior to the patient entering the bed. The extent the load cells were detecting weights prior to the patient entering the patient support apparatus 20, 20a, those readings are automatically eliminated from the patient's weight reading.

Figure 4:
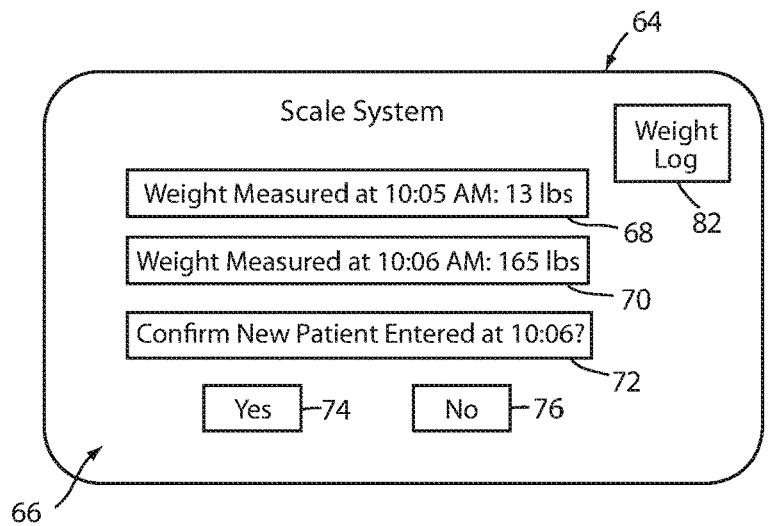
FIG. 4 is a view of an illustrative screen shot showing an auto-zeroing function of the measurement subsystem.

In at least one embodiment, measurement subsystem 54 communicates with display 64 on user interface 60 and shows the caregiver the weight readings both prior to and after the patient enters the patient support apparatus 20 or 20a. FIG. 4 shows an illustrative example of a screen shot 66 displayed on touchscreen display 64 that enables a caregiver to auto-zero a scale system contained with patient support apparatus 20 or 20a. Controller 56 is adapted to cause screen shot 66 to automatically appear after it detects what it concludes is the entry of a patient onto patient support apparatus 20, 20a. In other embodiments, controller 56 does not automatically display screen shot 66, but instead allows a caregiver to access screen shot 66 through appropriate manipulation of icons and/or menus on touchscreen display 64. Such icons may include, for example, an icon that brings up information regarding the scale system on patient support apparatus 20, 20a, and the screen shot with scale system information includes a link, button, menu, or other feature that enables a caregiver to access screen shot 66.

Regardless of how it is accessed, screen shot 66 includes a baseline weight indication 68 (FIG. 4). Baseline weight indication 68 tells the caregiver what cumulative weight was measured by load cells 36 prior to a patient entering on the patient support surface 28 of patient support apparatus 20, 20a. The number indicated in FIG. 4 is thirteen pounds, but this has been done merely for illustration purposes. The actual baseline weight reading is determined by taking a suitable number of readings from load cells 36 during a period of relative stability and averaging them. Appropriate filtering of the outputs may be performed in order to ensure the outputs are representative of a stable reading. If the baseline reading changes by a constant amount prior to the patient entering patient support surface 28, then controller 56 will display the most recent baseline reading at baseline weight indication 68. Further, any such changes in the baseline weight reading will be logged, as will be described in greater detail below, and made available for review by the caregiver.

Screen shot 66 (FIG. 4) further includes a current total weight indication 70. Current total weight indication 70 displays the current total weight detected by load cells 36. This total weight is read from the load cells and calculated in any conventional manner, as would be known to one of ordinary skill in the art.

Screen shot 66 (FIG. 4) also includes a confirmation indicator 72 showing that controller 56 has determined that it is likely that a patient has entered patient support surface 28. Confirmation indicator 72 requests that the caregiver confirm that a patient has indeed entered onto patient support surface 28. Confirmation is provided or rejected by way of a yes button 74 or a no button 76. Yes and no buttons 74 and 76 are not physical buttons, but instead are images displayed on touchscreen display 64 that, when pressed cause controller 56—or a controller inside of user interface 60—to react appropriately. In some alternative embodiments, measurement subsystem 54 is configured to automatically recognize that a patient has entered onto patient support surface 28 without asking for confirmation from the caregiver. Regardless of whether confirmation is needed or not, controller 56 determines, in one embodiment, that a patient has likely entered onto patient support surface 28 when a weight increase above a predefined threshold takes place. Such threshold may vary, but in one embodiment is one hundred pounds. In other embodiments, as will be discussed in greater detail below, controller 56 determines that a patient has likely entered onto patient support surface 28 by also, or alternatively, consulting signals from one or more vital sign sensors that are adapted to detect one or more vital signs of a patient positioned on patient support surface 28.

Figure 5:
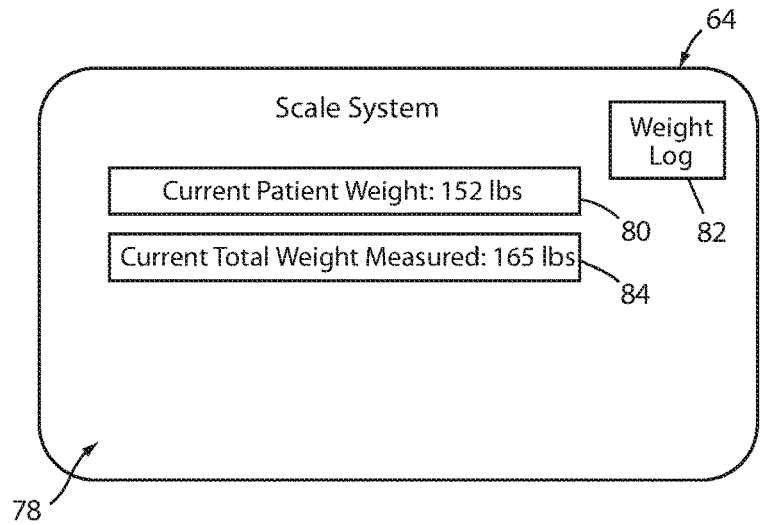
FIG. 5 is a view of another illustrative screen shot showing a weight display function of the measurement subsystem.

If a caregiver presses the yes button 74 (FIG. 4) and confirms that a patient has indeed entered patient support surface 28, then a new screenshot 78 is displayed, one illustrative example of which is shown in FIG. 5. Screenshot 78 includes a total patient weight indicator 80 that displays the currently measured weight of the patient. In this example, the currently measured patient weight is 152 pounds, although it will be understood that this is merely an illustrative example. This patient weight is computed by subtracting the baseline weight displayed in indicator 68 (13 pounds in FIG. 4) from the total weight displayed in indicator 70 (165 pounds in FIG. 4). By confirming that a patient entered onto patient support surface 28 immediately following the baseline weight reading shown at indicator 68, controller 56 knows that the weight increase that took place at approximately 10:06 AM was due to a patient, and is therefore able to attribute this weight change to the patient. Because the baseline weight was known immediately previously to this change, it is not necessary for the caregiver to zero the system to determine this patient weight because this zeroing effectively happens automatically through the subtraction of the weight reading displayed at indicator 68 from the weight reading displayed at indicator 70.

Figure 7:
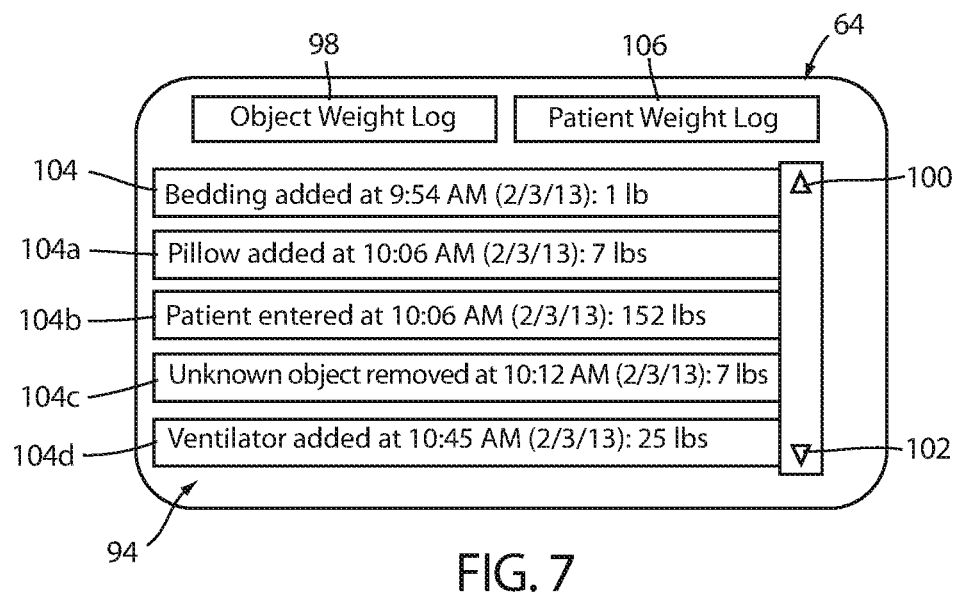
FIG. 7 is a view of another illustrative screen shot showing one portion of a weight log maintained by the measurement subsystem.

Screen shot 78 further includes an indicator 84 that displays the current total weight measured by load cells 36. In this illustrated example, the current total weight matches that measured at 10:06 AM (as shown in indicator 70 in FIG. 4) because no other objects have been added or removed from the patient support surface 28 since the patient entered it. However, if objects are added to, or subtracted from, the patient support surface 28 after the patient has entered (e.g. after 10:06 AM in this example), the weight displayed at indicator 84 will change. As will be explained in greater detail below, a caregiver is able to obtain additional information about these subsequent weight changes by pressing on a weight log icon 82 that will bring up a weight log screenshot 94, one example of which is shown in FIG. 7, which includes an explanation for this weight change.

Figure 6:
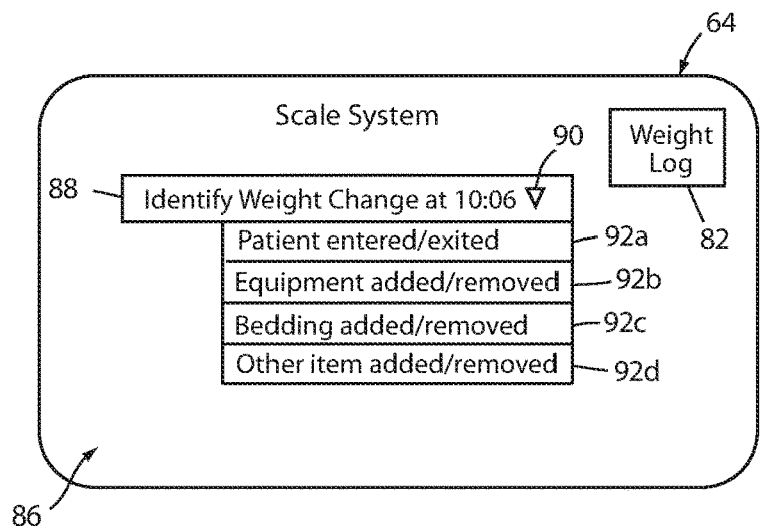
FIG. 6 is a view of another illustrative screen shot showing a weight event identification function of the measurement subsystem.

If a caregiver rejects the patient entry indication of indicator 72 (FIG. 4) by pressing on no button 76, then display 64 will display a different screen shot, such as a screen shot 86 shown in FIG. 6. Screen shot 86 displays an identify indicator 88 that enables a caregiver to identify what caused the weight change indicated on screen shot 66 (i.e. the weight change at 10:06 AM in this example). Identify indicator 88 includes a menu icon 90 that, as displayed, is a downward arrow. Pressing on menu icon 90 generates a number of potential identity indicators 92a, 92b, 92c, 92d, etc. that are displayed underneath identity indicator 88. Potential identity indicators 92 list possible identifications of the cause for the weight change detected at 10:06 AM (in this example). As shown, potential identity indicator 92a corresponds to a patient having entered or exited patient support surface 28; potential identity indicator 92b corresponds to a piece of equipment having been added or removed from patient support surface 28; potential identity indicator 92c corresponds to bedding being added or removed from patient support surface 28; and potential identity indicator 92d corresponds to an unidentified object being removed or added to patient support surface 28. Once a caregiver presses on the appropriate identity indicator 92, controller 56 will store that identity in memory, including the weight change corresponding to that identity, as well as the time when that weight change occurred. In other words, the selection made by the caregiver from the various identity indicators 92 will be stored in a weight log that, as discussed in more detail below, is accessible by pressing on weight log icon 82.

The list of potential identity indicators 92 shown in the screen shot 86 of FIG. 6 is not intended to be a complete list. Additional potential identities can be added. As but one example, a potential identity indicator 92 corresponding to the addition or removal of pillows could be added. Still other potential identity indicators 92 are possible.

The "other item" potential object identity indicator 92d shown in FIG. 6 enables a caregiver to custom identify an object whose identity does not appear in the list of potential identity indicators 92 displayed on screen shot 86. When a caregiver presses on indicator 92d in FIG. 6, a screen shot (not shown) is displayed that includes a full QWERTY keyboard and a space for typing a custom identity of the object that was added or removed (in this example, the object added at 10:06 AM). After the caregiver types the appropriate identification, he or she presses an enter or return icon that records the typed identification in the weight log. If the caregiver does not know the identity of the object added or removed, the caregiver can type in "unknown," or decline to type anything, in which case the object will be automatically identified by measurement system 54 as "unknown" in the weight log.

In some embodiments, greater granularity is provided to a caregiver after selecting one of the potential identity indicators 92. That is, after the caregiver presses one of these buttons, another menu of items that are described with greater specificity is provided, and the caregiver is able to select a more specific object corresponding to the weight change. For example, if the caregiver presses on the equipment added/removed indicator 92b, a subsequent menu is displayed that identifies various specific types of equipment. Such equipment includes, for example, pumps, ventilators, respirators, IV poles, etc. Once the caregiver selects the specific types of equipment (or enters a default equipment identity if the correct one is not listed), measurement subsystem 54 records the identity in the weight log.

FIG. 7 shows an illustrative weight log screen shot 94 that is displayable on touch screen display 64 in response to a caregiver pressing the weight log icon 82, which appears in screen shot 66 (FIG. 4), screen shot 78 (FIG. 5), and screen shot 86 (FIG. 6). Access to weight log screen shot 94 may also be provided in different manners (such as a button or icon on a main menu for touch screen display 64). Weight log screen shot 94 provides two different types of weight changes—those associated with patient weight changes and those associated with object removals or additions. It will be understood by those skilled in the art that, in other embodiments, the weight changes for the patient's weight could be combined into a single log with the object weight changes. In the example shown in FIG. 7, the object weight log has been chosen for display, as indicated by a darkened object weight log indicator 98.

Weight log screen shot 94 (FIG. 7) displays a log of weight changes, including when the weight changes occurred, the magnitude of the weight change, and a magnitude of the weight change. As shown, these elements are displayed in chronological order, with older weight changes appearing at the top and more recent weight changes appearing at the bottom. An up arrow icon 100 and a down arrow icon 102 change the time range for the displayed set of logged weight changes when pressed. In other words, pressing on up arrow icon 100 in the example of FIG. 7 will display weight log events that occurred prior to 9:54 AM, while pressing on down arrow icon 102 will display weight log events that occurred after 10:45 AM (if any). The speed at which the time range changes may accelerate if the caregiver presses and holds down on either of up or down arrow icons 100 or 102. Further, other icons or inputs can be included on screen shot 94 that enable the caregiver to enter a custom time range.

The weight events included in the weight log are initially generated automatically by controller 56 based on one or more algorithms that will be described in greater detail below. However, the caregiver is provided the opportunity to confirm or reject each and every one of the automatically generated identifications. Such rejection and confirmation can be carried out in a variety of different manners. One manner is illustrated in FIG. 4 and described above for confirming or rejecting the entry of a patient onto patient support surface 28. Another method includes touching any of weight event indicators 104 shown in FIG. 7. Touching weight event indicator 104 will bring up another screen shot (not shown) in which the caregiver is given the opportunity to confirm or reject the identification of the object proposed by controller 56. If the caregiver rejects the proposed identification, he or she is given the opportunity to input a custom identification of the weight event. Whatever custom identification he or she inputs will then be displayed as a weight event 104 on screen shot 94. If he or she chooses not to enter any identification, the weight event 104 will be listed as "unknown."

If a caregiver accepts a proposed identification of a weight event 104, the identification is recorded by controller 56 and stored in memory. Further, in some embodiments, controller 56 is configured to change an aspect of the confirmed weight event indicators 104 so that they are differentiated from those weight event indicators 104 that have not been confirmed by the caregiver. This differentiation may be made in any suitable manner, such as by changing the background colors of the confirmed weight event indicators 104 to a color different from the unconfirmed weight event indicators, changing the border line color or thickness for the event indicators 104, adding or changing a symbol positioned in or adjacent to each of the event indicators, or by other means. Whatever method is utilized, the caregiver is presented with a log of weight events 104 on screen 94 wherein those weight events 104 that have been confirmed are clearly and easily distinguishable from those weight events 104 that have not been confirmed. To the extent desired, the caregiver can then confirm any unconfirmed weight events 104, or otherwise alter them so that they are correct. The weight log entries shown in FIG. 7 are stored in memory 58 on board the patient support apparatus 20, 20a and retained until a caregiver manually erases them. In some embodiments, as will be discussed in greater detail below, the weight event log entries are forwarded to one or more healthcare network applications or servers running on a healthcare network. Such applications or servers may include, among others, an electronic medical record system.

As was noted, the screen shot 94 shown in FIG. 7 illustrates the weight events 104 that are associated with object entry and exit (as well as patient exit and entry). Measurement subsystem 54 also keeps track of changes in patient weight. In order for a caregiver to access these, he or she presses on the patient weight log indicator 106 shown in FIG. 7. Such pressing will bring up another screen shot on display 64, such as the screen shot 108 shown in FIG. 8. Screen shot 108 is associated with patient weight change events, as indicated by the darkened background of patient weight log indicator 106. Pressing on object weight log 98 on screen shot 108 will return the caregiver to screen shot 94 of FIG. 7.

Patient weight log indicator 106 (FIG. 8) includes a listing or log of patient weight events 110. These patient weight events 110 are displayed in chronological order in a fashion similar to the object weight event indicators 104 of FIG. 7. Further, the patient weight events 110 are displayed over a time range that is adjustable through the use of up and down arrow icons 100 and 102, in the same manner as has been discussed above with respect to FIG. 7. The patient weight events 110 listed on screen shot 108 include the time and measured weight of the patient whenever he or she enters patient support surface 28, as well as whenever he or she leaves patient support surface 28. Further, the patient weight events 110 listed on screen shot 108 include the amount of weight gained or lost by the patient while residing on the patient support surface 28, including the beginning time and ending time of the measured weight change. Patient weight event indicators 110a and 110c in FIG. 8 show examples of this type of patient weight change event, including the time interval over which these changes occurred.

Figure 8:
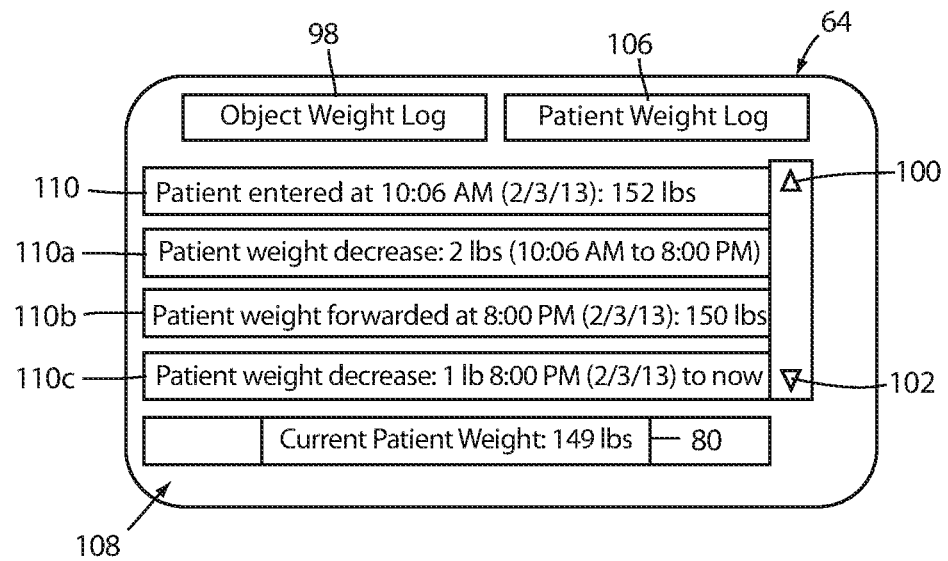
FIG. 8 is view of another illustrative screen shot showing a second portion of the weight log maintained by the measurement subsystem.

In the embodiment shown in FIG. 8, screen shot 108 also lists patient weight events 110 corresponding to weight measurements that have been forwarded by a caregiver to a location remote from the patient support apparatus 20, 20a, such as an electronic medical record system. An example of this is shown by weight event 110b where the caregiver forwarded the patient weight reading taken at 8:00 PM to the patient's electronic medical record. This forwarding is carried out in any suitable manner, such as by transmitting it through a WiFi connection on the bed to a healthcare network having an electronic medical records system server or application.

Still further, although not shown on the illustrative screen shot 108 of FIG. 8, measurement subsystem 54 also records and lists as a patient weight event 110 any auto-zeroing function carried out by a caregiver. Such auto-zeroing can take place shortly after a patient enters the patient support surface 28 (as was described above with respect to FIGS. 4 and 5), or it may take place at any time that a caregiver chooses, regardless of how long the patient may or may not have been lying on the patient support surface 28. By pressing an appropriate button 62 on user interface 60, or touching an appropriate icon on touch screen display 64, measurement subsystem 54 allows a caregiver to manually zero the weight readings sensed by load cells 36 at any time. If a patient is already positioned on patient support surface 28, controller 56 will capture the current weight reading and subtract from it the last baseline weight reading corresponding to when the patient first entered the patient support surface. This baseline reading is computed by subtracting from the currently captured weight reading all recorded non-patient weight increases that have occurred since the time the patient first entered the patient support surface 28, and adding to the currently captured weight reading all recorded non-patient weight decreases (e.g. to account for objects that may have been removed). Recorded weight changes that correspond to changes in the patient weight (e.g. patient weight gain or weight loss entries 104) are neither subtracted nor added to the currently captured weight reading.

Therefore, for example, if the patient had entered five hours previously, and during those five hours a one pound pillow had been removed and a thirty-five pound piece of medical equipment had been set on the patient support surface 28 (or other a portion of the patient support apparatus 20, 20a that influenced the load cells 36), controller 56 would add one pound to the current total weight reading and subtract thirty-five pounds from the currently captured total weight reading, for a net change of negative 34 pounds. Therefore, if the current total weight reading was 180 pounds, controller 56 would calculate that the current weight of the patient is 146 pounds (180+1−35=146). Any changes in the patient weight that had been detected in the five hours since the patient entered onto patient support surface 28, which would be recorded as patient weight event indicators 104, would not be used in this auto-zeroing calculation.

Figure 9:
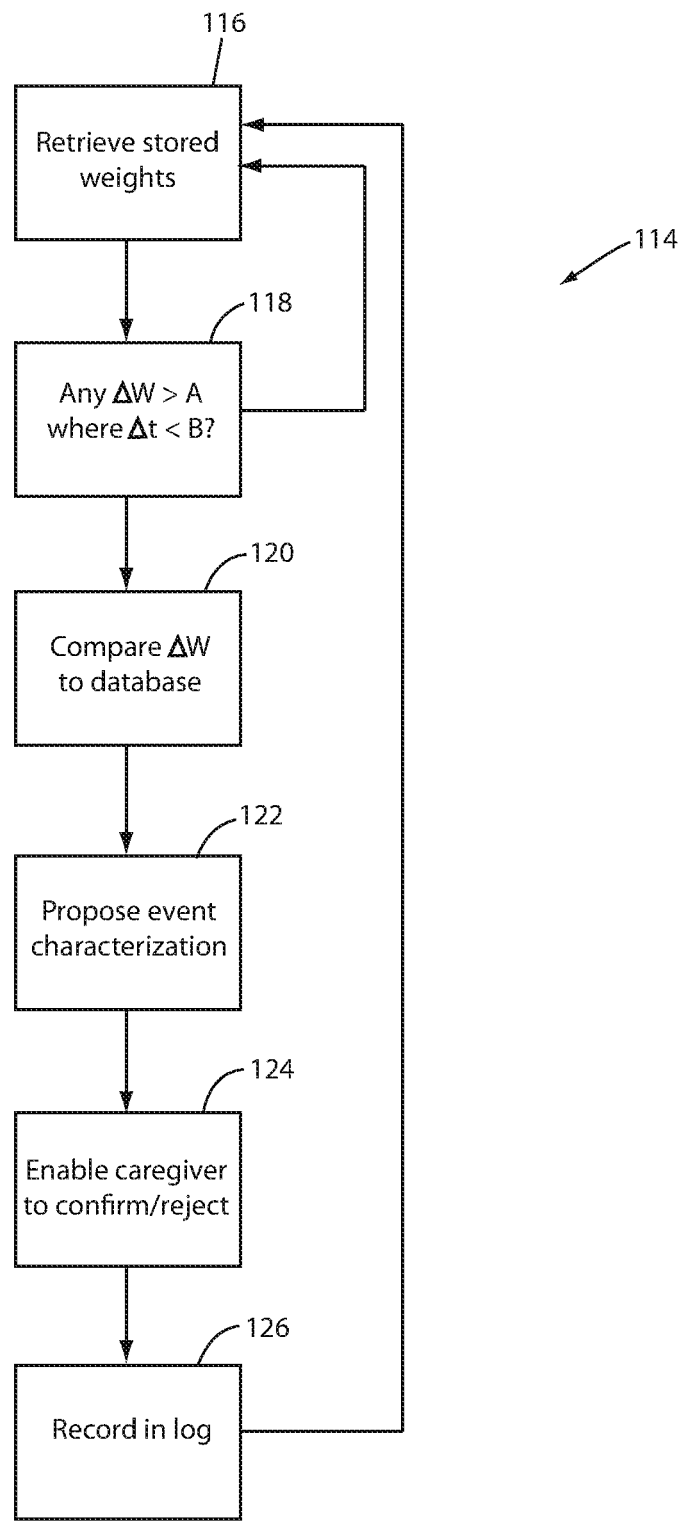
FIG. 9 is a flowchart of a weight event identification algorithm that is used by the measurement subsystem.

FIG. 9 illustrates an event identification algorithm 114 that is used by controller 56 in proposing the identification or characterization of events in the patient and object weight logs. Algorithm 114 begins at a retrieval step 116 where weight readings taken by load cells 36 are retrieved from memory 58. Such weight readings, as was noted previously, are taken nearly continuously from the moment power is supplied to patient support apparatus 20 or 20a, or another initiation event occurs. These weight readings are taken multiple times per second and recorded in memory 58. Algorithm 114 finds and characterizes events of significance in these recorded weights by first retrieving them at step 116, and then examining them at step 118. More specifically, during step 118, controller 56 examines the retrieved weight readings to determine if the weight readings represent a change in weight greater than a weight threshold (exemplified as threshold A in FIG. 9) that occurs during a time period less than a time threshold (exemplified as threshold B in FIG. 9). In other words, controller 56 examines the weight retrieved at step 118 to see if there are any significant weight changes (greater than the weight threshold) that occur within a relatively short time period (less than time threshold B). If the weight changes are less than the threshold, then controller 56 interprets these changes as being due to the patient's weight slowly changing. Such miniscule changes are not individually noted as a patient weight event 110, but instead are recorded, cumulatively summed, and entered into the patient weight log as an event 110 when another event occurs, such as the patient entering or leaving the patient support surface 28, or an object being added or removed from patient support surface 28. While the precise value of the weight threshold may vary, in one embodiment, it is on the order of a fraction of a pound.

Controller 56 also examines at step 118 the time period over which a weight change occurs. If the weight change occurs gradually, then controller 56 interprets this as the patient's weight changing. If the weight change occurs suddenly, then controller 56 interprets this as an object or person entering or exiting the patient support surface 28. While the precise time may vary, in one embodiment the time threshold is on the order of a couple of seconds.

If no weight changes are detected at step 118 that meet both the time and weight change thresholds (A and B in FIG. 9), the controller returns to step 116 and retrieves any stored weights that have not yet been analyzed by algorithm 114. If a weight change is detected at step 118 that meets both the time and weight change thresholds, the controller moves to step 120 where it compares the weight change to a database. The database contains a listing of weight change ranges that are mapped to potential objects or reasons for the weight change. For example, the database may characterize any weight changes of greater than 100 pounds as likely corresponding to a patient entering or exiting the patient support surface 28. Other thresholds for characterizing the weight change as a person exiting or entering can, of course, be used (particularly if the patient support apparatus is used in a pediatric setting). The database might also characterize any weight changes of less than 5 pounds but greater than the weigh threshold A (step 118 of FIG. 9) as likely corresponding to a change in bedding or a pillow being added or removed. Changes in weight greater than this threshold, but less than the threshold corresponding to a patient entering or exiting, could be assigned as corresponding to medical equipment being removed or added. To give algorithm 114 greater accuracy, the weights of medical devices, bedding, and/or other objects that are commonly used in conjunction with the patient support apparatus 20 can be input into the database along with their identity (all of which is stored in memory 58).

At step 122, controller 56 characterizes the weight change based upon the information located in the database at step 120. That is, controller 56 searches through the database and finds the weight entry stored therein that is the closest match for the weight change identified at step 118. If there are no close matches, then controller 56 characterizes the weight change at step 122 as "unknown," or some other equivalent characterization. If controller 56 finds a match in the database, it characterizes the weight change according to what is identified in the database. Examples of such weight characterizations are shown in FIGS. 6 and 7 and illustrated in potential identity indicators 92 and weight event indicators 104. In other words, controller 56 will characterize weight events at step 122 in such manner as: pillow added/removed; or bedding added/removed; or ventilator added/removed; or medical device added/removed; or patient exited/entered; or unknown object added/removed; or the like.

After making a preliminary or proposed identification of the weight events detected by controller 56, controller 56 enables the caregiver to confirm or reject these preliminary or proposed identifications at step 124 of algorithm 114. If the caregiver neither confirms nor rejects these proposed identifications, they are recorded at step 126 as unconfirmed. If the caregiver accepts the proposed identifications, they are recorded at step 126 as confirmed. If the caregiver rejects the proposed identification, the caregiver is given the opportunity to manually identify the weight event, which then is recorded at step 124 as confirmed. If the caregiver does not manually identify the rejected weight event, it is recorded as an unknown weight event at step 126.

The records recorded into the log at step 126 are made available for viewing by the caregiver via touch screen display 64. FIGS. 7 and 8 illustrate arbitrary examples of the display of these records. Further, as was noted above, the illustrative screen shots of FIGS. 7 and 8 allow, in at least some embodiments, a caregiver to confirm or reject the proposed characterization simply by pressing on the item 104, 110, which will bring up a different screen (not shown) that enables a caregiver to identify the object.

Figure 10:
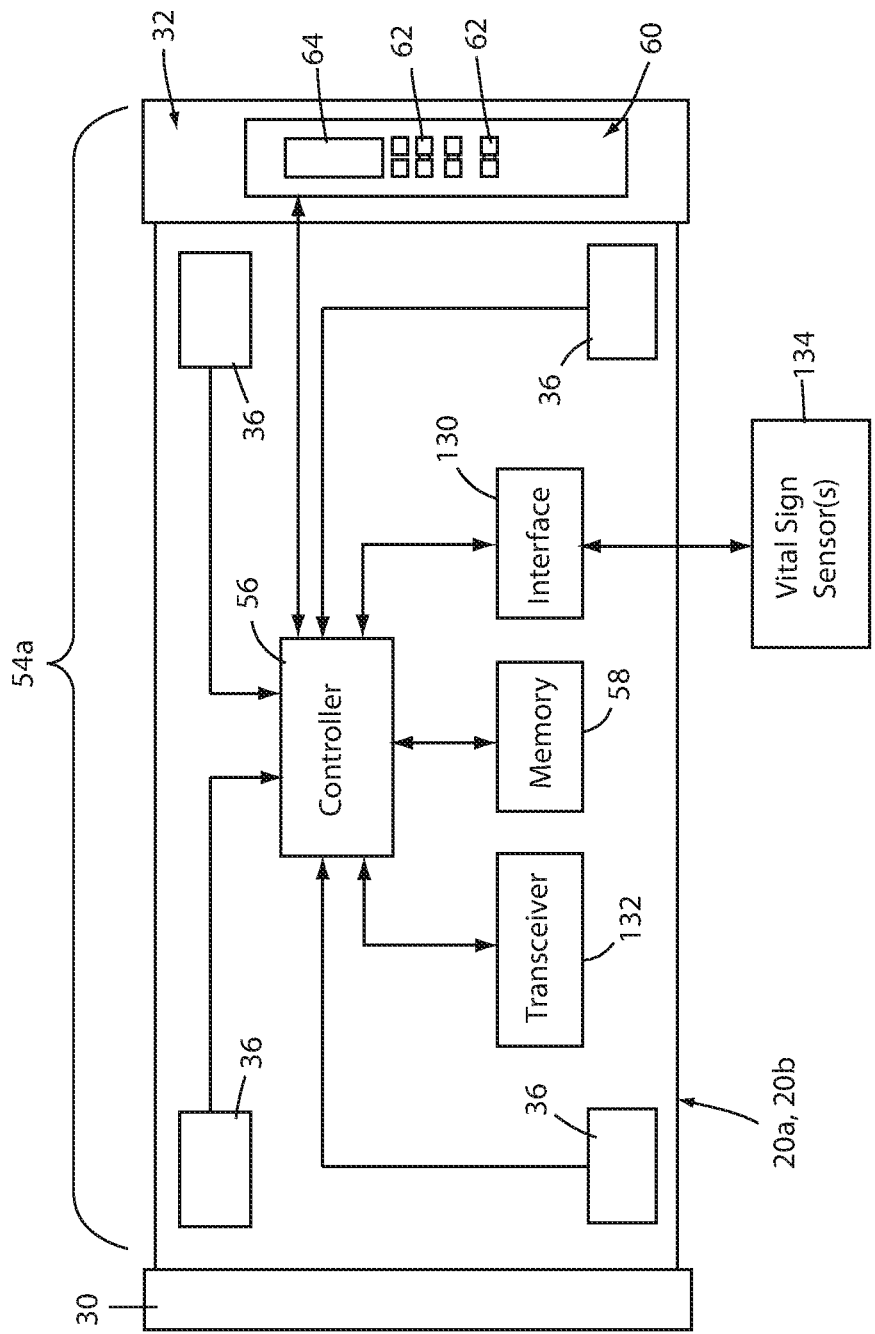
FIG. 10 is a plan view diagram of a second measurement subsystem that may be incorporated into either of the patient support apparatuses of FIG. 1 or 2.

FIG. 10 illustrates an alternative embodiment of a measurement subsystem 54a. Measurements subsystem 54a is capable of being incorporated into either or both of patient support apparatuses 20 and 20a. Those components of measurement subsystem 54a that are the same as corresponding components of measurement subsystem 54 are identified by the same reference number, while those components of measurement subsystem 54a that are not in subsystem 54 are identified by new reference numbers.

The physical architecture of measurement subsystem 54a differs from subsystem 54 in that it includes an interface 130 and a transceiver 132, both of which are in electrical communication with controller 56. Interface 130 is adapted to communicate with one or more vital sign sensors 134 so that controller 56 may use these vital sign signals (or absence of them) for improving the characterization of weight events, and/or for other purposes, as will be described herein. Interface 130 is a USB (Universal Serial Bus) port in one embodiment, although it will be understood by those skilled in the art that it may take on a variety of different forms, such as, but not limited to, an RS-232 port, a wireless interface, or any other suitable port for communicating information with vital sign sensor 134.

Transceiver 132 is used by controller 56 for forwarding selected information from measurement subsystem 54a to other devices, such as a hospital Ethernet, or another recipient. In one embodiment, transceiver 132 is a WiFi radio capable of communicating with a wireless access point of the hospital Ethernet in accordance with IEEE 802.11 standards, or in accordance with other standards. More specific uses of transceiver 132 are discussed below.

The vital sign sensor 134 may be any conventional sensor used to measure one or more patient vital signs, such as, but not limited to, respiration rate and heart rate. While other types of sensors can be used, non-invasive vital sign sensors 134 have advantages over invasive sensors 134 in that the vital signs can be measured without having to attach anything to the patient. In one embodiment, vital sign sensor 134 is a pressure sensing mat that is positioned on top of, or integrated into, a mattress (not shown) positioned on top of patient support surface 28. Such a pressure sensing mat includes an array of pressure sensors adapted to detect interface pressure exerted by a patient on the mattress. By analyzing those pressure sensors positioned in the vicinity of the patient's thoracic cavity, respiration and/or heart rate signals can be determined. In one embodiment, vital signs sensor 134 is a pressure sensing flexible mat like that disclosed in commonly assigned PCT patent application serial number PCT/US12/27402 filed Mar. 2, 2012 by Stryker Corporation, and entitled SENSING SYSTEM FOR PATIENT SUPPORTS, the complete disclosure of which is hereby incorporated herein by reference. In such an embodiment, the pressure sensing flexible mat outputs both a patient respiration rate and a patient heart rate.

In another embodiment, vital signs sensor 134 is a vital sign sensor incorporated into a mattress, such as the mattress disclosed in commonly assigned U.S. patent application Ser. Nos. 13/836,813 and 61/697,010, entitled INFLATABLE MATTRESS AND CONTROL METHODS and PATIENT SUPPORT, respectively, the former of which was filed Mar. 15, 2013 and the latter of which was filed Sep. 5, 2012, the complete disclosures of both of which are hereby incorporated herein by reference. When incorporated into a mattress, the vital sign sensor, in some embodiments, detects respiration and/or heart rates by a pressure sensor included within the mattress that detects fluid pressure changes within one or more bladders contained within the mattress. Such fluid pressure changes are filtered for frequencies within those of the normal heart rate and breathing rate and processed, such as through Fourier analysis, or otherwise, to yield a heart rate and/or respiration rate. In embodiments using the mattress construction disclosed in the above-referenced Ser. Nos. 13/836,813 and/or 61/697,010 applications, the mattress also includes a plurality of depth sensors that measure the depth which the patient has sunk into the mattress. These depth sensor signals may be combined with the air pressure signals to determine a patient's breathing rate and or heart rate.

In still another embodiment, vital signs sensor 134 is incorporated into the patient support apparatus 20 or 20a itself. For example, in one embodiment, the vital signs sensor uses the load cells 36 to detect vibrations caused by the patient's breathing and/or heart beating. These signals are processed—such as by controller 56 or another suitable controller—to determine a patient's heart rate and/or breathing rate. A more detailed description of how the load cells 36 can be used to determine a patient's breathing rate and/or heart rate is disclosed in commonly assigned U.S. Pat. No. 7,699,784 issued to Wan Fong et al. and entitled SYSTEM FOR DETECTING AND MONITORING VITAL SIGNS, the complete disclosure of which is hereby incorporated herein by reference.

Figure 11:
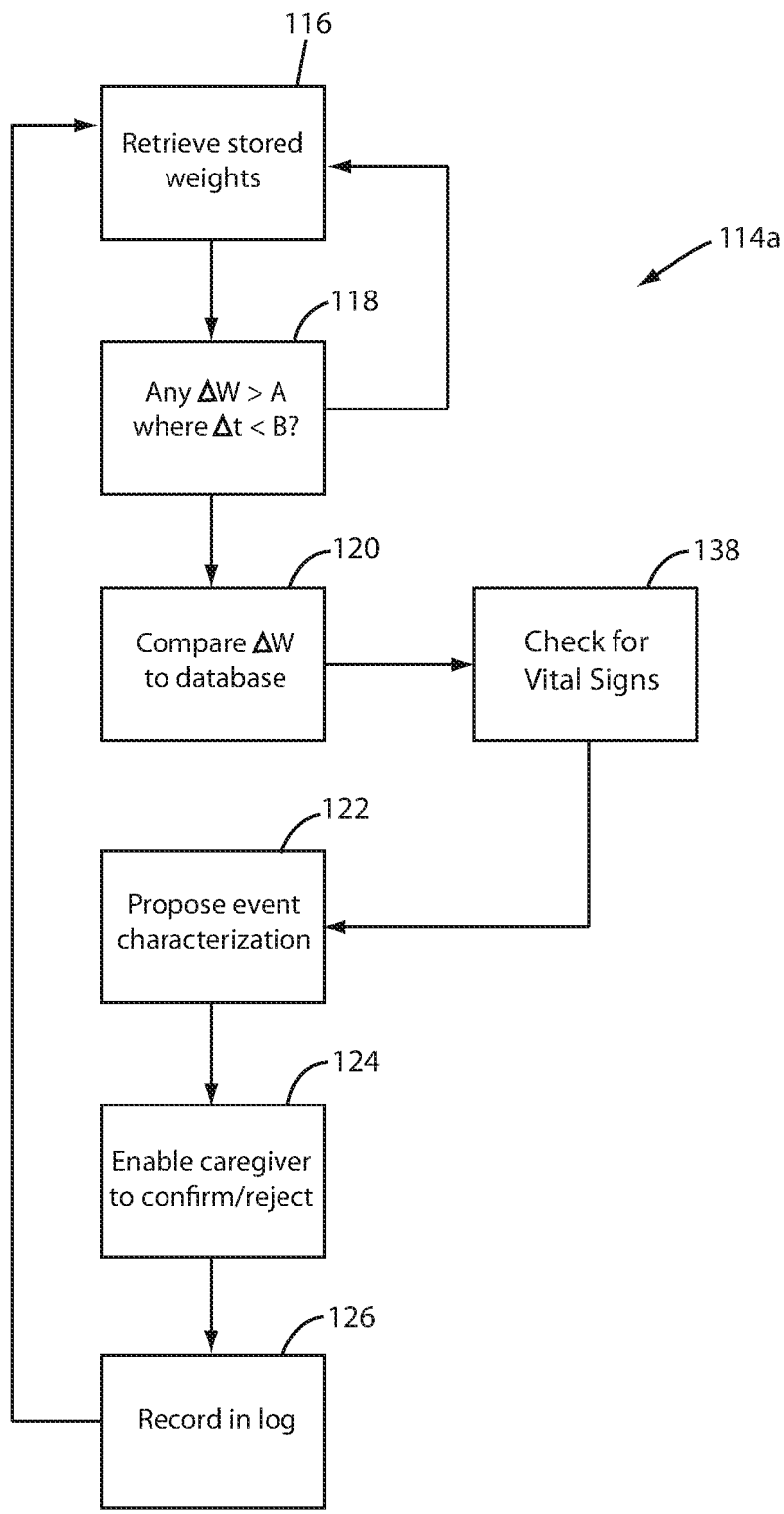
FIG. 11 is a flowchart of a second weight event identification algorithm that may be used by the measurement subsystems of FIG. 10 or 15.

Regardless of the physical form of the vital sign sensors 134, controller 56 is adapted, in at least one embodiment, to use these vital sign signals to distinguish between non-human objects on patient support surface and humans positioned thereon. Knowing this difference is useful in at least several different situations. For example, the vital sign information can be used for better identifying the weight events listed in any of the weight logs discussed herein. More particularly, FIG. 11 illustrates an alternative event identification algorithm 114a that uses the vital sign information from sensors 134 to facilitate the identification of the objects that are added to, or removed from, patient support surface 28. The steps of algorithm 114a that are the same as those of algorithm 114 are labeled with the same reference numbers and carry out the same functions that have been previously been described above with respect to algorithm 114. The difference between algorithms 114a and 114 is the addition of a vital signs check step 138.

Vital signs check step (FIG. 11) follows step 120 where controller 56 has consulted a database of weight changes and potential objects/persons that might correspond to the detected changes. Controller 56 uses the presence or absence of vital sign signals at step 138 to better select the proper characterization from the event database. That is, if no vital signs are detected at step 138, then controller 56 will not characterize a weight increase as a patient entering the patient support apparatus, even if the weight increase is otherwise above the threshold corresponding to a potential human entering the patient support apparatus (e.g. 100 pounds, in some embodiments). Still further, controller 56 records the absence or presence of vital signs signals from sensor 134 and uses the history of these signals near the time of the weight event to help characterize the event. For example, if the load cells detect the removal of, say, 90 pounds of weight, controller 56 will check to see if vital signs were detected immediately before this 90 pound weight removal, and if vital signs are currently being detected (after the removal). If vital signs were previously detected, but are not currently detected, controller 56 interprets this removal of 90 pounds as a patient exit. However, if vital signs were previously detected and are still detected, then controller 56 concludes that the patient is still on the patient support surface, and characterizes this weight loss as an object removal, not a person removal. In still other situations, if no vital signs were detected both before and after the weight decrease, controller 56 will characterize the weight removal as an object removal.

Vital signs sensor 134 therefore provides additional information to controller 56 that enables it to better characterize the weight change events detected by load cells 36. In particular, vital signs sensor 124 allows controller 56 to better distinguish between the movement of inanimate objects and living beings onto and off the patient support surface. After checking for the absence or presence of vital signs at step 138, controller 56 proceeds to step 122 and proposes a characterization of the weight event, in the same manner that has been previously discussed. The rest of algorithm 114a operates in the same manner as algorithm 114.

Figure 12:
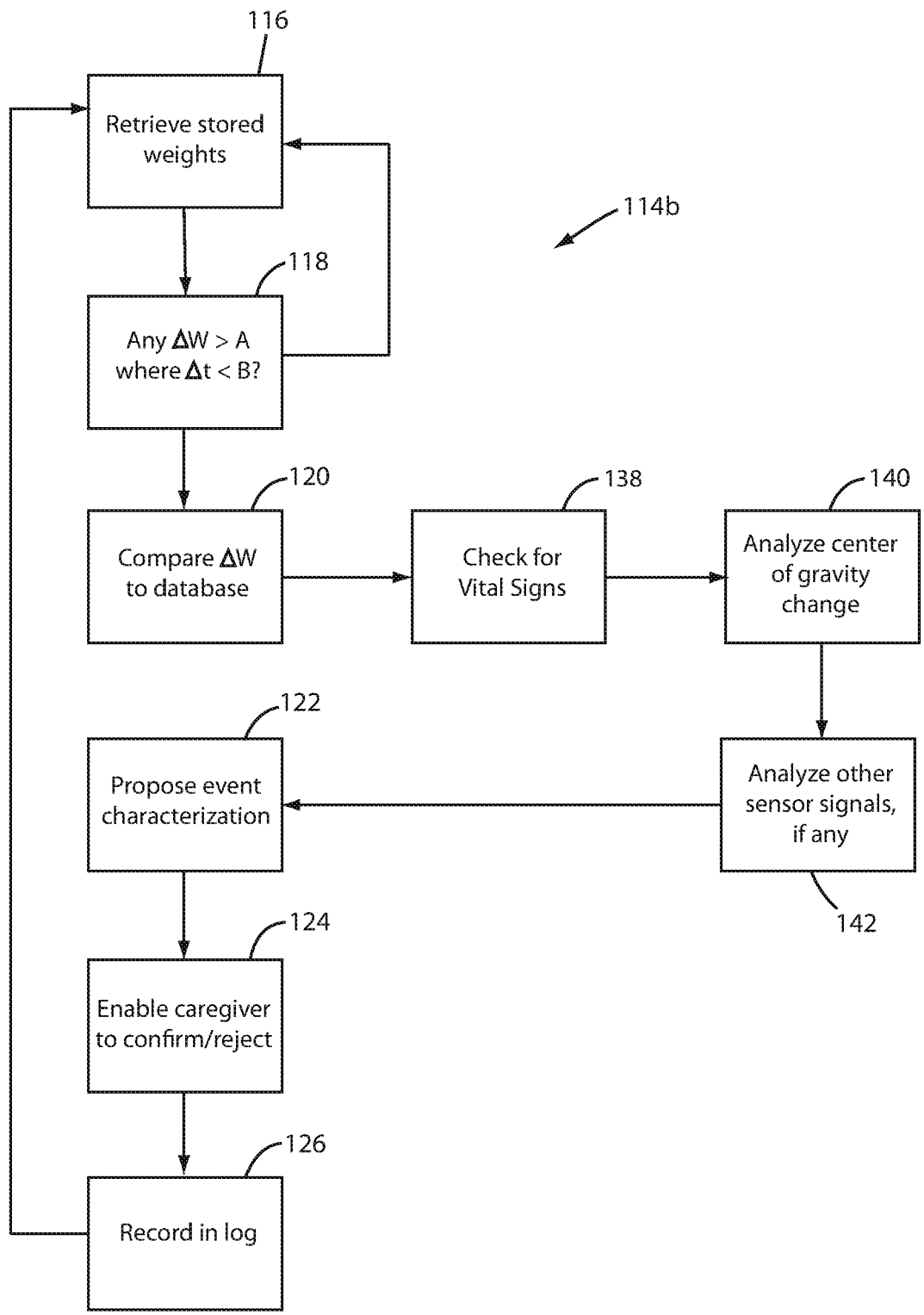
FIG. 12 is a flowchart of a third weight event identification algorithm that may be used by the measurement subsystems of FIG. 10 or 15.

FIG. 12 illustrates another alternative embodiment of an event identification algorithm 114b. As with algorithms 114 and 114a, algorithm 114b is carried out by controller 56, and may be implemented on any of the patient support apparatuses described herein (e.g. 20 or 20a). Algorithm 114b differs from algorithm 114a by the addition of two additional steps: a center of gravity analysis step 140 and an additional sensor analysis step 142 (if any additional sensors are present). During center of gravity analysis step 140, controller 56 compares the calculated center of gravity of the mass on patient support surface immediately prior to the weight event to the calculated center of gravity immediately after the weight event. These calculations of the center of gravity are performed using known techniques, such as those disclosed in commonly assigned U.S. Pat. No. 5,276,432 issued to Travis and entitled PATIENT EXIT DETECTION MECHANISM FOR HOSPITAL BED, the complete disclosure of which is hereby incorporated herein by reference.

During the comparison of the calculated centers of gravity immediately prior to and immediately after the weight event at step 140, controller 56 determines which direction the center of gravity has moved, and the magnitude of the change in the center of gravity. This direction and magnitude are used by controller 56 in its proposed identification of the objects added to, or removed from, patient support surface 28. For example, if the center of gravity shifts toward the head end of patient support apparatus 20 in a manner that is generally consistent with the usual placement of a pillow, controller 56 will use this information to identify the object added or removed as a pillow (assuming the weight change is within the expected weight range for pillows). As another example, if bedding is removed or added, the center of gravity of such bedding is very close to the center of the patient support surface 28 (because the bedding is normally spread out over the entire support surface, or nearly the entire support surface), and little, if any, change in the center of gravity will be detected. Controller 56 uses this information in identifying, or ruling out, the addition or removal of bedding as corresponding to the weight event. In still other situations, the use of medical equipment added to, or removed from, the patient support apparatus may normally be expected to occur at certain positions on the patient support surface, which will change the center of gravity in predictable manners. These expected changes in centers of gravity are stored in memory 58 and used for more accurate identification of the weight events detected by the load cells 36.

After completing step 140, controller 56 moves onto step 142 in algorithm 114*b* (FIG. 12). At step 142, controller 56 analyzes any additional sensor information in order to be able to more accurately characterize the weight event at step 122. Such additional sensor information may include any suitable sensors. In one embodiment, the additional sensors include a flexible pressure sensing array positioned on top of, or incorporated into, the mattress supported on the patient support apparatus. One example of such a flexible pressure sensing array is disclosed in the above-mentioned commonly-assigned PCT patent application serial number PCT/US12/27402 filed Mar. 2, 2012 by Stryker Corporation, and entitled SENSING SYSTEM FOR PATIENT SUPPORTS. In addition to, or in lieu of, sensing vital signs, this pressure sensing mat is also able to detect the overall shape of the patient or object positioned on the mattress. This overall shape is processed by either controller 56, or a controller within the flexible pressure sensing mat, to determine whether the shape corresponds to a human or an object. The result of this determination is used by controller 56 at step 142 to distinguish between the objects and humans moving onto or off the patient support apparatus.

In yet another embodiment, the additional sensors used at step 142 include one or more near field transceivers incorporated into patient support apparatus 20 or 20*a* that are able to communicate via near field communication with near field tags worn by patients or caregivers, or which are attached to equipment. If the tags are worn by patients, controller 56 is able to easily detect via this near field communication whether or not the patient is the same or a new patient. If the tags are attached to equipment, then controller 56 may be able to use the ID in that tag to identify the equipment, and therefore use that identification in the weight event log. Examples of near field transceivers that may be incorporated into patient support apparatuses and used to detect patient, caregiver, and/or equipment ID tags is disclosed in commonly assigned U.S. patent application Ser. No. 13/802,992, filed Mar. 14, 2013 by applicants Michael Hayes et al., and entitled COMMUNICATION SYSTEMS FOR PATIENT SUPPORT APPARATUSES, the complete disclosure of which is hereby incorporated herein by reference. Still other types of sensors that detect other patient or object information may be used and processed at step 142.

After completing step 142 (if any additional sensors are available), controller 56 proceeds to step 122 where it characterizes the weight event based on the analyses carried out in steps 120, 138, 140, and 142. The characterization is then presented to the caregiver for confirmation/rejection at step 124, and recorded in the weight event log at step 126, in the same manners as have been previously described above.

While the foregoing descriptions of measurement subsystems 54 and 54*a* have described a patient exit and/or entry event as merely corresponding to a generic patient, measurement subsystems 54 and/or 54*a* can be modified to distinguish between new patients that are entering the patient support surface 28 for the first time, and old patients that have previously been on the patient support surface 28. More particularly, step 122 of algorithms 114, 114*a*, and/or 114*b* can be modified to include the sub steps identified collectively as step 122*a* set forth in FIG. 13. It will therefore be understood that step 122*a* in FIG. 13 can replace step 122 in any of algorithms 114, 114*a*, and/or 114*b*.

Figure 13:
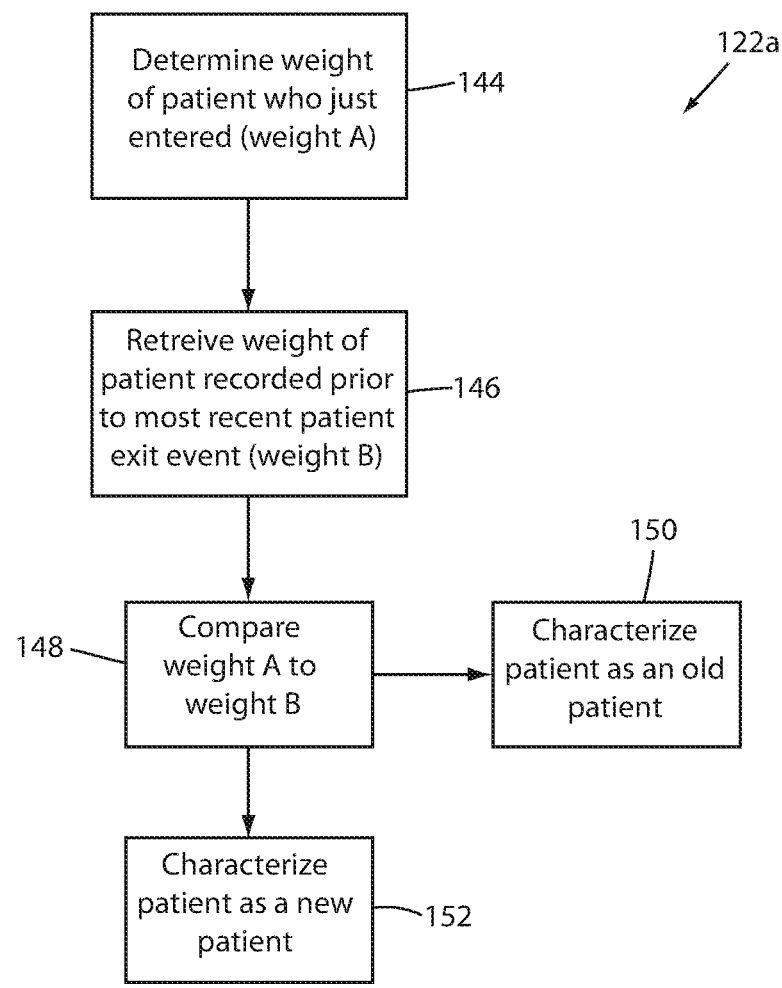
FIG. 13 is a flowchart of a first modification that may be made to one of the steps in the identification algorithms of FIG. 9, 11, or 12.

Step 122*a* of FIG. 13 begins at a sub step 144 that is only invoked if controller 56 has previously determined that a weight event corresponds to a patient entering patient support surface 28. In other words, step 122*a* is not invoked if controller 56 determines that a weight event corresponds to an object being removed from, or added, to patient support surface 28, or if it corresponds to a patient exiting patient support surface 28. During sub step 144, controller 56 determines the weight of the patient (or other person) who has just entered patient support surface. This weight has been arbitrarily labeled "weight A" in FIG. 13. This weight determination takes place automatically in the manners described above (that is, it includes any zeroing out of weights detected by load cells 36 that do not correspond to patient weight).

After controller 56 has determined at sub step 144 the weight of the patient who has just entered onto patient support surface 28 (weight A in FIG. 13), controller 56 moves to sub step 146, where it retrieves from memory 58 the patient weight recorded moments before the most recent patient exit event (identified as "weight B" in FIG. 13). That is, as has been noted above, measurement subsystems 54 and 54*a* are both configured to automatically take repeated weight measurements substantially continuously and record those, or at least record any changes of significance (any series of multiple weight recordings that do not have any significant change can be stored in memory as a constant weight with a beginning and ending time in order to save memory). At sub step 146, controller 56 retrieves from memory the patient weight that was recorded at a moment preceding (either immediately, or closely preceding) the last patient exit from patient support surface (weight B). If there are no previously recorded patient exits, then the patient who just entered the patient support apparatus must be a new patient, so controller 56 skips to sub step 152 (discussed below) where it characterizes the patient as a new patient.

However, in those cases where a previous patient exit event was recorded, controller 56 retrieves the patient weight B and moves to sub step 148 where it compares weights A and B to each other. More specifically, at sub step 148, controller 56 determines the percentage of difference (if any) between weights A and B. If weight A differs from weight B by more than a threshold percentage, then controller 56 concludes that the patient who just recently entered patient support surface 28 is a patient different from the one who previously occupied patient support surface 28, and therefore corresponds to a new patient. Controller 56 therefore moves onto sub step 152 where it characterizes in the weight event log the patient entry as corresponding to a new patient. As with all entries in the weight log, the caregiver has the opportunity to confirm or reject this characterization.

If weight A does not differ from weight B by more than the threshold percentage, then controller 56 moves onto sub step 150, where it characterizes the recent patient who just recently entered the patient support surface 28 as the same patient (i.e. an old patient) who was previously occupying patient support surface 28. This characterization is recorded in the weight event log and the caregiver has the opportunity to confirm or reject it.

The threshold percentage used in sub step 148 may vary from embodiment to embodiment, but will generally be in the neighborhood of one or two percent. Such small percentage changes in weight may be due to a variety of different activities that the patient may have engaged in during the time they exited the patient support surface. Such activities include the patient removing or adding clothing, eating food, drinking liquids, and/or visiting the restroom. Any weight changes greater than this threshold will be assumed to indicate that a new patient has entered the patient support surface 28. In some embodiments, the threshold percentage may be dynamically correlated to time: that is, the longer the patient is gone from the patient support surface, the more the threshold percentage may increase, which would reflect the fact that greater periods of time away from the patient support surface would afford greater time for weight-changing activities.

Modified weight characterization step 122*a* therefore gives measurement subsystems 54 and/or 54*a* the added ability of providing greater information about the patient weight events by being able to distinguish between old and new patients. Modified step 122*a*, however, can be improved even further in other embodiments. That is, modified step 122*a* is still not able to distinguish between a new patient and an old patient who happen to have the same weight (or have weights that are less than the threshold of sub step 146). In order to address this possibility, characterization step 122*a* can be modified to an even greater step in some embodiments.

Figure 14:
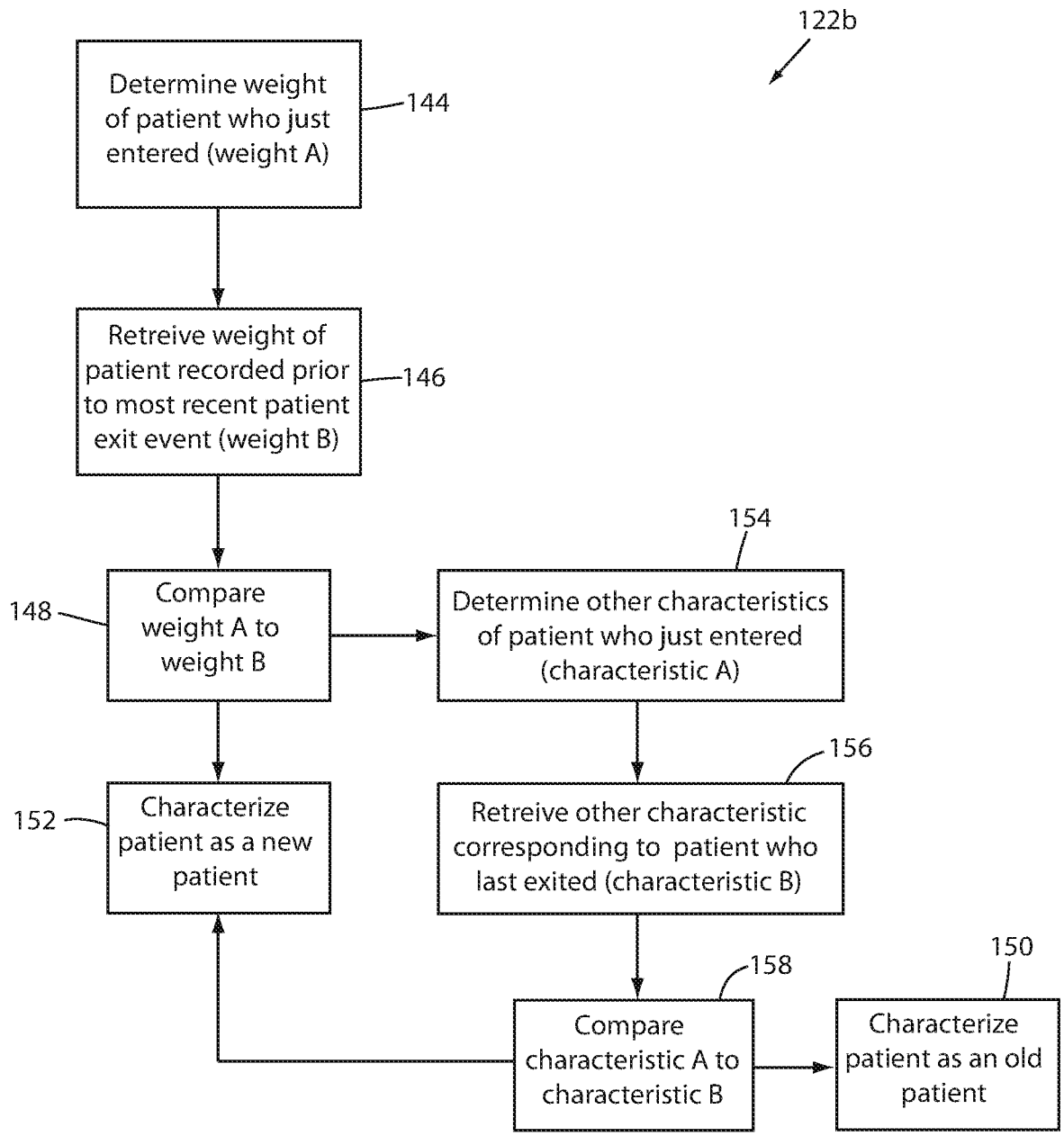
FIG. 14 is a flowchart of a second modification that may be made to one of the steps in the identification algorithms of FIG. 9, 11, or 12.

FIG. 14 illustrates another modified characterization step 122*b* that is adapted to be able to better distinguish between old and new patients who have the same, or nearly the same, weight. Modified characterization step 122*b* is useful in those measurements subsystems, such as subsystem 54*a*, where controller 56 is in electrical communication with one or more additional sensors that provide additional information about the patient. Step 122*b* of FIG. 14, like step 122*a* of FIG. 13, begins at a sub step 144 that is only invoked if controller 56 has previously determined that a weight event corresponds to a patient entering onto patient support surface 28. In other words, step 122*b* is not invoked if controller 56 determines that a weight event corresponds to an object being removed from, or added, to patient support surface 28, or if it corresponds to a patient exiting patient support surface 28.

Sub steps 144, 146, 148, 150, and 152 of modified characterization step 122*b* are the same as those sub steps of modified characterization step 122*a*, with the sole possible exception of sub step 148. Sub step 148 of step 122*b* may differ from sub step 148 of step 122*a* by utilizing a different threshold. In some embodiments, this threshold may be greater than in step 122*a*. This is because modified step 122*b* uses additional information to distinguish between old and new patients, so only greater weight changes will lead controller 56 to conclude a new patient has entered at step 152. Whether or not weight variations less than this increased threshold are the result of weight change or a different patient is resolved by sub steps 154, 156, and 158, as described below.

If controller 56 determines at sub step 148 that the weights A and B are not different by more than the threshold, it moves onto sub step 154, where it determines another characteristic of the patient who has just recently entered onto patient support surface 28. This another characteristic is determined by one or more additional sensors that are in communication with controller 56. One such additional sensor is the vital sign sensor 134 shown in FIG. 10 of measurement subsystem 54*a*. Other sensors can also be used that are coupled to controller 56 by way of an additional interface (not shown). Such other sensors could include a video camera, still frame camera, infrared sensor, or other types of sensors. Regardless of the specific sensor, controller uses the information provided by that sensor to determine a characteristic (characteristic A) of the patient who just entered the patient support surface 28.

After determining characteristic A at sub step 154, controller 56 moves onto sub step 156 where it determines the corresponding characteristic (recorded in memory 58) of the patient who last exited patient support surface 28 (characteristic B). Controller 56 then moves to step 158 where it compares characteristic A to characteristic B. If the two differ by more than a threshold percentage, then controller 56 concludes the two patients are different, and moves to step 152, where it characterizes the patient as a new patient. If the two do not differ by more than the threshold percentage, then controller 56 concludes that the same patient has re-entered patient support surface 28 and moves onto step 150, where it characterizes the patient as an old patient.

The characteristics that are used by step 122*b* in sub steps 154, 156, and 158 may vary. In one embodiment, the characteristic is a patient height. Such patient heights are able to be determined by a flexible pressure sensing mat positioned on top of, or incorporated into, a mattress positioned on top of patient support surface 28. Such mats sense the top-most pressure sensor in the array that is contacted by the patient, as well as the bottom-most pressure sensor in the array that is contacted by the patient. From this, the patient height is able to be determined. One example of such a mat that can be used with step 122*b* and measurement subsystem 54*a* to determine patient height is the mat disclosed in the commonly-assigned PCT application serial number PCT/US12/27402 filed Mar. 2, 2012 by Stryker Corporation, and entitled SENSING SYSTEM FOR PATIENT SUPPORTS, which was previously incorporated herein by reference. As was mentioned above, this type of mat is also able to detect vital signs and can be used as vital signs sensor 134. This mat can therefore serve the dual purpose of providing both vital signs and patient height to controller 56, all via the same interface 130.

As an alternative to patient height, characteristics A and B might refer to other patient distances that are measurable using a flexible pressure sensing mat of the type disclosed in the PCT/US12/27402 application. For example, instead of patient height, the flexible pressure sensing array might detect the distance between two common high pressure points on the patient's body, such as the sacrum and the patient's heels. In other embodiments, the pressure sensing mat might detect lateral patient dimension, such as dimensions characterized by the distance between the patient's shoulders, or the width of the patient's pelvis, or other measurements.

In still another embodiment, patient support apparatus 20 or 20*a* includes a near field transceiver (not shown) that is adapted to communicate with an RF ID tag, or other identification device, worn by each patient. In this embodiment, characteristic A refers to the unique number, or other characteristic, of the ID tag worn by the patient who has just returned to the patient support surface 28, while characteristic B refers to the unique number, or other characteristic, of the ID tag worn by the patient who previously had exited from the patient support surface 28. If the two numbers, or other characteristics, of the tags match, then the same patient has returned to patient support surface 28, while if the two numbers, or other characteristics, do not match, then a new patient has entered onto patient support surface 28. The integration of near field communication transceivers into patient support apparatuses for detecting, among other things, patient ID tags is disclosed in above-mentioned commonly assigned U.S. patent application Ser. No. 13/802, 992, filed Mar. 14, 2013 by applicants Michael Hayes et al, and entitled COMMUNICATION SYSTEMS FOR PATIENT SUPPORT APPARATUSES, the complete disclosure of which has already been incorporated herein by reference.

Regardless of the specific characteristic used in step 122b, controller 56 stores the characteristic each time a patient enters the patient support surface. This is stored in memory 58. When a patient entry event is detected, controller 56 takes a new reading of this characteristic at sub step 154, and retrieves an old reading from memory 58 at sub step 156 (if there is no reading, then controller 56 proceeds to step 150 and characterizes the patient as a new patient). If the two characteristics are different, then controller determines that the two patients are different. If they are the same, then the controller determines that the same patient who previously occupied the patient support surface 28 has re-entered the support surface 28.

Whenever controller 56 determines that a new patient has entered the patient support surface 28, whether at sub step 152 of modified algorithm 122a or modified algorithm 122b, controller 56 is configured to notify the caregiver and prompt the caregiver to clear out any old data corresponding to the previous patient that is stored in memory 58, or any other memories contained on the patient support apparatus 20, 20a. Such notification may involve displaying a prompt on display 64, or it may involve issuing an aural alert, such as one or more beeps, or it may involve issuing a visual alert, such as a light or flashing light. Such notification is intended to remind the caregiver that, because a new patient has entered the patient support apparatus, any old data corresponding to a previous patient should be cleared, and new data may need to be entered for the new patient.

The old data to be cleared, as well as the new data to be entered, can take on a variety of different forms, and will vary from patient support apparatus to patient support apparatus, as well as from healthcare facility to healthcare facility. In general, however, such data may include the patient's name, height, weight, BMI, bed sore risk (e.g. Braden scale), fall risk, infection risk, and other sorts of data. If the caregiver confirms that a new patient has entered the bed, then controller 56, in some embodiments, is programmed to automatically clear the old data corresponding to the old patient from the memory (or memories) on board the patient support apparatus. In other embodiment, controller 56 merely reminds the caregiver to clear this memory, but does not do this clearance automatically. Still further, controller 56 is programmed to remind the caregiver to enter this new information whenever it determines that a new patient has entered the patient support apparatus.

Another feature of measurement subsystems 54 and/or 54a is the ability to characterize whether a patient supported on patient support apparatus 20, 20a is sleeping or not. When this feature is included within subsystems 54 and/or 54a, controller 56 may be programmed to consider sleeping an event that is listed in the patient weight logs. Alternatively, when a patient has fallen asleep, as well as the beginning and ending times of such sleep, may be recorded and displayed via different manners than the weight logs. Regardless of where the sleeping records are stored and/or displayed, measurements subsystems 54 and/or 54a are configured to determine whether a patient is sleeping by monitoring the heart rate and respiration rate of the patient and analyzing those signals to determine the sleeping or waking state of the patient. In other words, measurement subsystems 54 and/or 54a use one or more vital sign sensors 134 to determine whether a patient is asleep or not, and to record the times when the patient is awake and the times when the patient is asleep.

The characteristic changes in a person's breathing rate and heart rate during sleep are known in the art and do not need to be described in detail herein. Generally speaking, however, the breathing rate becomes more regular during sleep and the heart rate is reduced. The patient's temperature also decreases. Consequently, in addition to the respiration and heart rate, measurement subsystem 54 and/or 54a can also include communication between controller 56 and one or more temperature sensors. Regardless of which specific sensors are used, however, controller 56 makes a determination that a patient is asleep or awake and records that for viewing by the caregiver.

Figure 15:
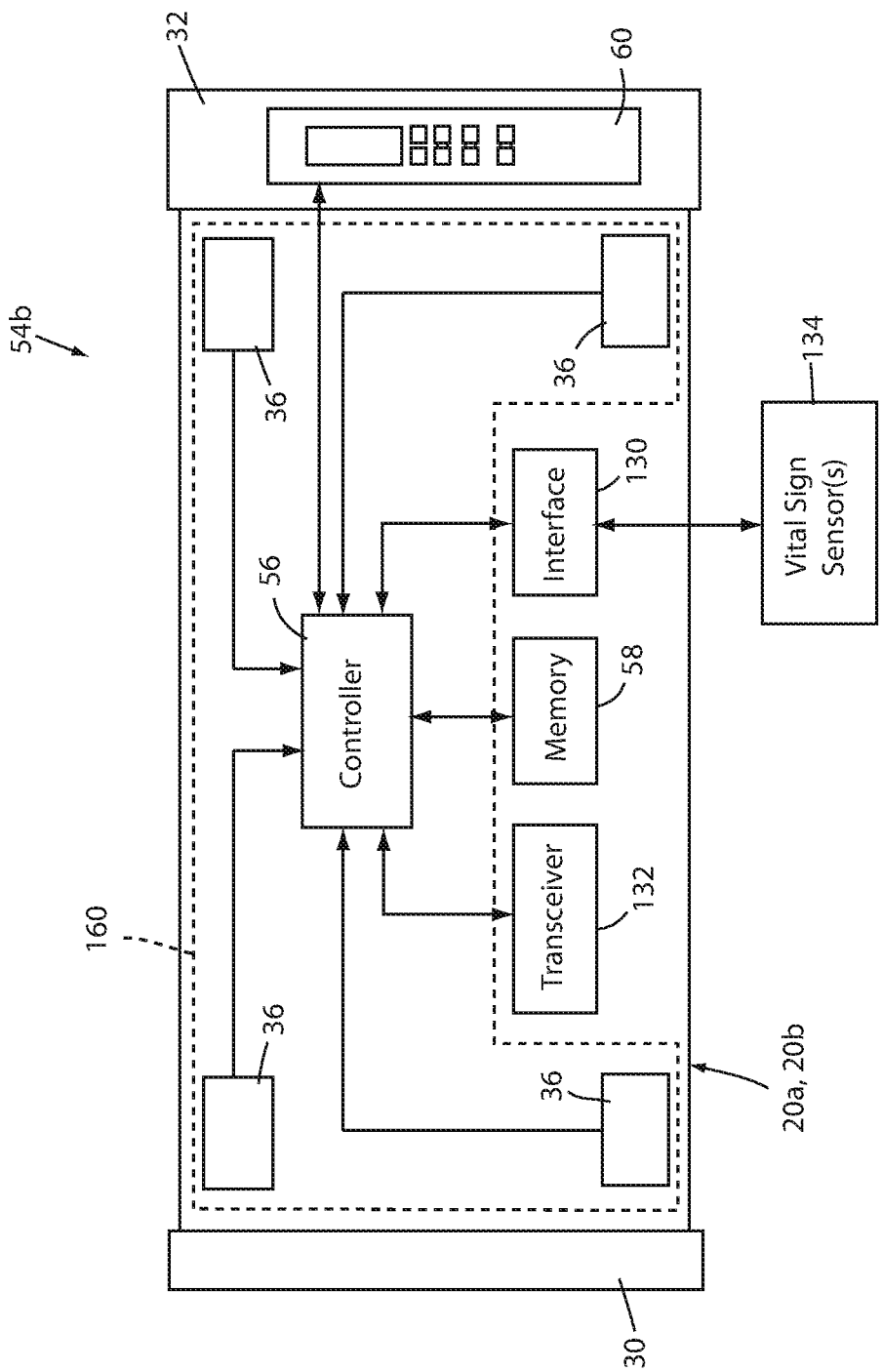
FIG. 15 is a plan view diagram of a third measurement subsystem that may be incorporated into either of the patient support apparatuses of FIG. 1 or 2.

FIG. 15 illustrates another embodiment of a measurement subsystem 54b that may be incorporated into either of patient support apparatuses 20 or 20a. Those components of measurement subsystem 54b that are different from subsystems 54 or 54a are labeled with different reference numbers, while those components that are the same are labeled with the same reference numbers. Measurement subsystem 54b differs from measurement subsystems 54 and 54a in that it explicitly includes an exit alert system 160. Exit alert system 160, in the illustrated embodiment, includes controller 56 and load cells 36. Exit alert system 160 is adapted to issue an alert when a patient has exited, or is about to exit from the patient support surface 28. In some embodiments, exit alert system works by monitoring a patient's center of gravity and issuing an alarm if the patient's center of gravity moves outside of a predefined zone, such as described in the exit system disclosed in the commonly assigned U.S. Pat. No. 5,276,432 issued to Travis and entitled PATIENT EXIT DETECTION MECHANISM FOR HOSPITAL BED, the disclosure of which has already been incorporated herein by reference. In other embodiments, exit alert system is modified to include multiple zones of different dimensions, and a caregiver is allowed to select which zone the patient's center of gravity has to move beyond before an exit alert is issued. Still other forms of exit alert systems 160 are possible.

In addition to including exit alert system 160, measurement subsystem 54b also differs from measurement subsystems 54 and 54a in that it includes the ability to automatically re-arm the exit alert system 160 after a patient returns to patient support apparatus 20 or 20a. Measurement subsystem 54b accomplishes the automatic re-arming of exit alert system 160 by recording when the exit alert system 160 is turned on and when a patient exits, or otherwise moves in a manner that causes the exit alert system 160 to issue an alert. Thereafter, subsystem 54b monitors the load cells 36 (and/or the vital sign sensors, or additional sensors, if the support apparatus is equipped with them) to determine when the patient returns to the patient support surface 28. When the patient has returned, controller 56 of subsystem 54b is configured to automatically re-arm the exit alert system after a threshold amount of time has passed since the patient re-entered the support surface 28. The threshold amount of time may vary. In one embodiment, it is of the order of ten to twenty seconds. Other thresholds can be used.

Measurement subsystem 54b may use any of the techniques described above to determine that a patient has re-entered the patient support system. These include looking solely at the weight of the returning patient and comparing it to the patient's previous weight, as well as looking at vital signs, height measurements, patient dimension measurements, pressure sensor array measurements, and/or other measurements that enable controller 56 to determine that a patient—as opposed to a weighty object—has returned to patient support apparatus 20 or 20*a*.

Indeed, in some embodiments, controller 56 does not look at weight measurements at all, but instead relies upon vital sign signals solely. If the vital sign sensor 134 is able to once again detect vital signs after a patient has previously exited the support apparatus, controller 56 interprets this as evidence that the patient has returned to the support apparatus, and automatically re-enables the exit alert system. In one embodiment, the vital sign sensor 134 used to automatically re-arm the exit alert system is one or more of the load cells where controller 56 examines the vital signs sensed by the load cells, as opposed to the cumulate weight sensed by them. Such vital sign sensing using the load cells is disclosed in the commonly assigned U.S. Pat. No. 7,699,784 issued to Wan Fong et al. and entitled SYSTEM FOR DETECTING AND MONITORING VITAL SIGNS, the complete disclosure of which has already been incorporated herein by reference.

In addition to, or in lieu of, any of the functions of scale system auto-zeroing, weight event characterization, sleep determination, new/old patient detection, and the other features described above that measurement subsystems 54, 54*a*, and/or 54*b* are capable of, any one of these measurement subsystems may be configured to perform yet another function that will now be described. More particularly, any of measurement subsystems 54, 54*a*, and/or 54*b* may be used to perform an activity monitoring feature which will now be described. This activity monitoring function will be described in reference to FIGS. 16 and 17. In general, the activity monitoring function measures the amount of, and times of, movement and/or activity that a patient experiences while positioned on patient support surface 28.

Figure 16:
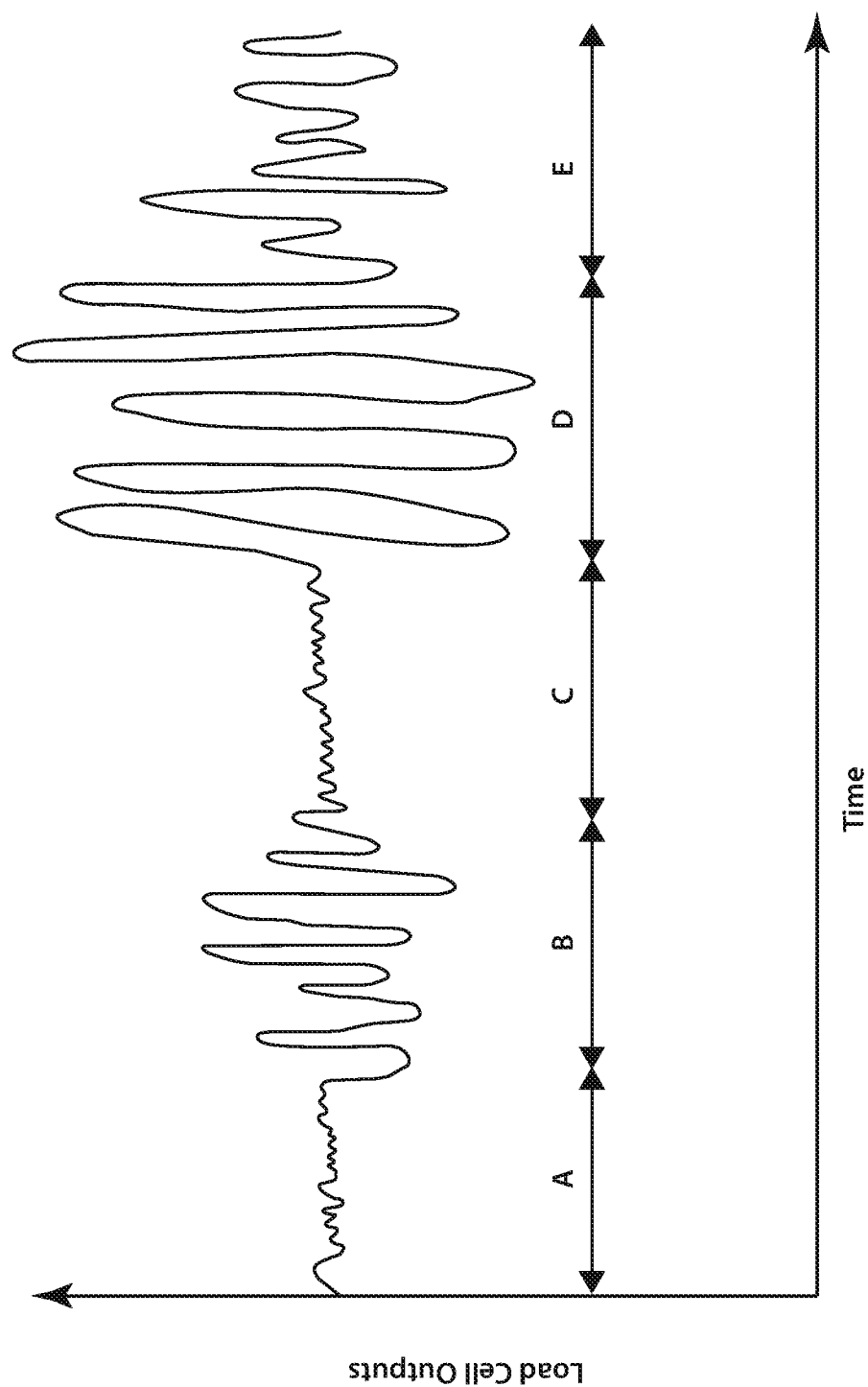
FIG. 16 is a diagram of an illustrative set of outputs that may be generated by force sensors, such as load cells, that are incorporated into any of the measurement subsystems described herein.

FIG. 16 illustrates an example of the outputs that might be generated from load cells 36 while a patient is positioned on patient support surface 28. As can be seen, the movement of the load cells varies at different periods of time. Controller 56 (in any of the measurement subsystems 54, 54*a*, or 54*b*) is adapted to characterize these various levels of movement, sum the total amount of time that a patient engages in these various levels of movement, and make that information available for display to the caregiver, and/or to forward that information to a remote location via transceiver 132. In the embodiment described herein, controller 56 characterizes the level of movement according to three different levels: low movement, medium movement, and large movement. It will be understood by those skilled in the art that different types of characterizations can be used, and that different numbers of movement levels can be used instead of the three described herein.

As shown in FIG. 16, controller 56 analyzes the outputs of the load cells 36 and breaks up their outputs into different time intervals A, B, C, D, E, etc. according to the level of movement that occurs in those intervals. Further, depending upon the level of movement that occurs in those intervals, controller 56 assigns a characterization to that level of movement. More specifically, in the example of FIG. 16, controller 56 assigns a low movement level to time interval A, a medium movement level to time interval B, a low movement level to time interval C, a high movement level to time interval D, and a medium movement level to time interval E. Further, controller 56 sums up the amount of time spent in each movement level, stores it in memory 58, and displays it on display 64 for a caregiver to look at.

The various different levels of movement are, in the example shown in FIG. 16, based on the amplitude of the load cell outputs and their variations. In other embodiments, instead of examining the load cell outputs, controller 56 is configured to examine changes in the center of gravity of the patient, as computed from the load cell 36 outputs. The levels of movement in such an embodiment are therefore based on the degree to which the center of gravity changes. The concept of categorizing the changes, however, remains the same, regardless of whether the load cell amplitudes are categorized, the center of gravity changes are categorized, or other measurements of movement are categorized.

Figure 17:
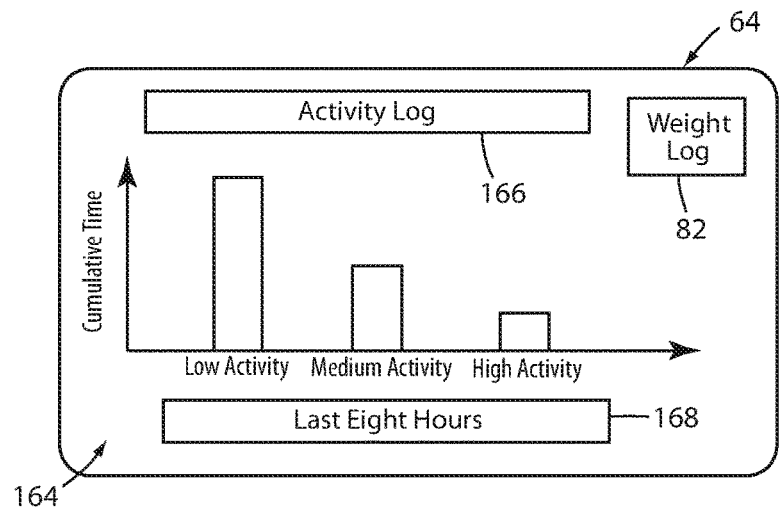
FIG. 17 is a view of an illustrative screen shot showing an activity log maintained by any of the measurement subsystems.

FIG. 17 illustrates one example of the information that controller 56 is configured to display on display 64 regarding the different levels of movement. More specifically, FIG. 17 shows an illustrative screen shot 164 of an activity log 166 that is displayable on touch screen display 64. Activity log 166 includes a bar chart having an X-axis and a Y-axis. The Y-axis corresponds to the total cumulative time (units not shown, and can vary). The X-axis corresponds to the different movement characterization levels that are available—in this example, low activity, medium activity, and high activity. The height of the different bars indicates how much time the patient has spent in each of the low, medium, and high activity states. A time range indicator 168 is included on the bottom of screen shot 164 that shows the time range corresponding to the data displayed in the bar chart. In the example of FIG. 17, the bar chart reflects the different levels of patient activity over the last eight hours. By touching indicator 168, a time range menu is displayed (not shown) that enables a caregiver to change the time range of the displayed data, including entering a custom time range. After the time range is changed, controller 56 re-computes the data for the bar graph according to the selected time range. That is, controller 56 adds up the time intervals A, B, C, etc. (examples of which are shown in FIG. 16) corresponding to each of the different activity levels, and then displays the cumulative sum for each activity level on the bar chart.

Screen shot 164 provides an easy way for a caregiver who has been away from the patient support apparatus 20 or 20*a* to see how active the patient has been during the caregiver's absence. This information can be useful in assessing whether the patient experienced a restful sleep or not, and/or it can be useful for determining what risk level a patient may have for developing bed sores, as well as for other purposes.

In some embodiments, screen shot 164 is modified to indicate what portions of the time displayed in the bar chart correspond to time when the patient was awake and what portions correspond to time when the patient was asleep. The manner of displaying this additional information can vary. In one embodiment, each of the bars is divided into two colors, one of which represents sleep and the other of which represent awake. Other manners of displaying this information can be used. The method for determining whether the patient is awake or not has been discussed above.

Screen shot 164 and controller 56 are further adapted, in at least some embodiments, to allow a caregiver to view the actual data on display 64 that was used to generate the bar chart. In other words, screen shot 164 and controller 56 are adapted, in some embodiments, to display the kind of data shown as an example in FIG. 16. This data provides more information to the caregiver because it indicates the times when the various levels of movement occurred, and the caregiver can therefore see if the periods of high movement were spread out, or occurred at only one or a few times, or otherwise analyze the data.

Figure 19:
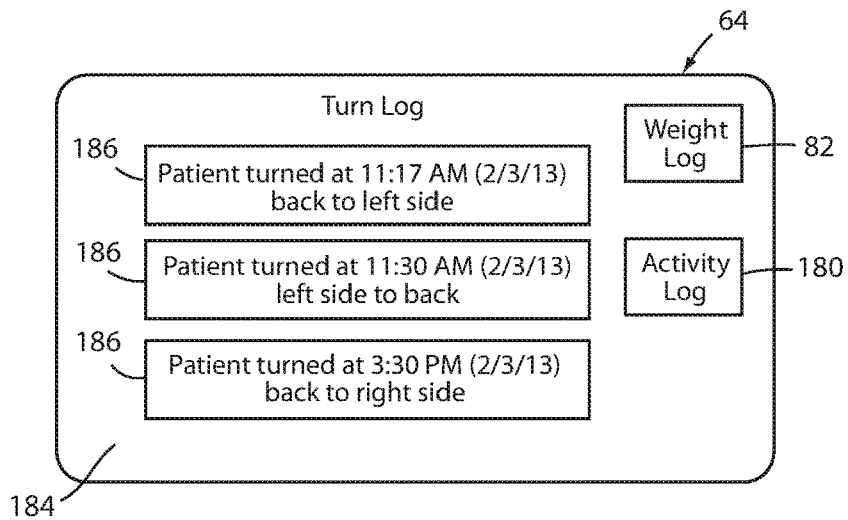
FIG. 19 is a view of an illustrative screen shot showing a turn log that may be maintained by any of the measurement subsystems.

Screen shot 164 also includes a weight log icon 82 (FIG. 17). This is included merely for illustrative purposes, and is not intended to indicate that the activity log shown in FIG. 17 is in any way dependent upon having a weight log feature in the same measurement subsystem. Some embodiments of patient support apparatus 20 or 20a include only a weight log feature, while other embodiments include only an activity log feature, while still other embodiments combine them both. If such a weight log feature is included in a patient support apparatus that also includes the activity log, then a weight log icon 82—such as that shown in FIG. 17—may be included in screen shot 164 to allow a caregiver to view the weight log by pressing on weight log icon 82. Similarly, the screen shots showing the weight log information (e.g. FIGS. 4-8 may be modified to include an activity log icon (one example of which is shown in FIG. 19 by activity log icon 180) that, when pressed, brings the caregiver to screen shot 164. In still other embodiments, the weight log and activity log information may be combined into a common log.

In addition to, or in lieu of, the measurement of different movement levels summarized above, measurement subsystems 54, 54a, and/or 54b can also be also programmed, in some embodiments, to issue an alert when controller 56 determines that a patient's movement level is so low that a patient's risk of developing bed sores has increased. In such embodiments, controller 56 examines two criteria: movement amounts and time. If the patient's level of movement has not exceeded a threshold for a specific amount of time, then controller 56 issues an alert, such as a visual alert on display 64, or an audio alert, or a flashing light, or a remote alert via transceiver 132. The threshold levels of movement and time can be predetermined and set by the manufacturer of the patient support apparatus 20 or 20a, or they can be programmed to be configurable by the caregiver. Indeed, in some embodiments, controller 56 will automatically set both the time and movement thresholds based upon bed sore risk assessment information that a caregiver inputs into patient support apparatus 20, 20a, or that is otherwise communicated to patient support apparatus 20, 20a (such as via transceiver 132). Such information includes Braden scale scores, or other bed sore risk assessments.

In still other embodiments, any of measurement subsystems 54, 54a, and/or 54b may be modified to include a patient turn recognition feature. When equipped with such a patient turn recognition feature, controller 56 automatically records the times when a patient is turned and makes this information available for display and/or for transmission (via transceiver 132) to electronic medical records, or other applications in communication with the healthcare Ethernet (or other communication network).

Figure 18:
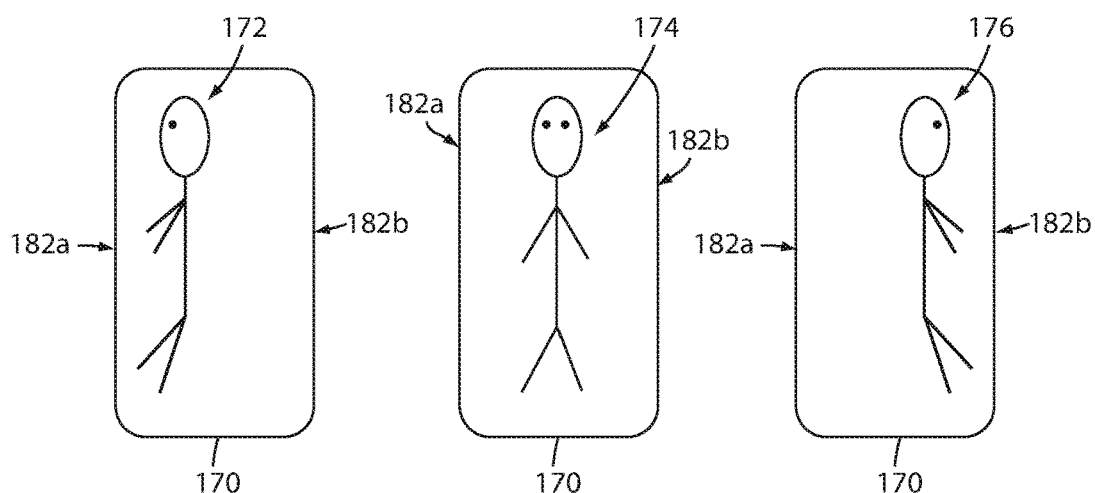
FIG. 18 is a plan view diagram illustrative three general positions in which a patient may be positioned on the patient support apparatus.

The patient turn recognition feature is an automatic feature implemented by any of the measurement subsystems wherein the load cells, or other sensors, are used to automatically detect when a patient turns while positioned on patient support surface 28. As shown in FIG. 18, a patient may rest on a mattress 170 supported on patient support surface 28 by lying on his or her right side—as indicated by position 172—or he or she may be lying on his or her back—as indicated by position 174—or he or she may be lying on his or her left side—as indicated by position 176 (it is rare for a patient to be lying on his or her stomach). The patient turn feature automatically detects which position 172, 174, or 176 the patient is in, automatically records the time at which a change in these positions occurs and the type of change (e.g. back to right side, back to left side, left side to back, or right side to back), and automatically records the amount of time that a patient spends in each different position. This information is made available for caregiver viewing on display 64 and/or it is transmitted to one or more servers or applications running on the healthcare computer network via transceiver 132.

The patient turn recognition feature differs from prior art turn recordation systems in that the patient turning is automatically recognized by measurement subsystem 54 (or 54a or 54b). In some existing patient support apparatuses, a caregiver is able to enter information into the patient support apparatus indicating that he or she has turned a patient. However, this requires manual entry by the caregiver. Further, this does not detect turns that a patient may make by himself or herself without the assistance of the caregiver. Still further, the automatic patient turn recognition feature described herein acts as a backup so that, if a caregiver forgets to enter information into the patient support apparatus indicating that a patient turn was performed, this information will nevertheless be automatically recorded. The automatic patient turn recognition feature also serves as a check to ensure that the caregiver is in fact turning the patient when he or she has indicated.

In some embodiments, the automatic turn recognition feature carried out by controller 56 is integrated into a turning protocol feature that is also present on patient support apparatus 20 or 20a. That is, in some existing beds, a caregiver can enter a protocol into the electronic system on the bed that indicates that the patient should be turned at a regular interval. Such a system can further issue alerts at each time interval if the caregiver does not manually enter information confirming that a turn has taken place. The automatic turn recognition feature described herein can be integrated into such a protocol system so that, if the patient turns on his or her own, the time interval is automatically reset and no alerts are issued or forwarded to the caregiver until a time period equal to the set interval passes without any turns detected. This can reduce the workload on the caregivers.

When automatically resetting any turn interval reminder, controller 56 may, in addition to looking at whether a turn has occurred or not, also look at how long the turn has lasted for. If the turn does not last for longer than a threshold amount of time, then controller 56 does not automatically reset the turn alert interval timer. This is because turns of very short duration are likely not sufficient to reduce the likelihood of a patient developing beds sores. Consequently, only turns that last for greater than a threshold justify automatic resetting of the turn interval reminder timer. In one embodiment, the threshold is initially set by the patient support apparatus manufacturer but is configurable by the caregiver so that it can be adjusted to a particular healthcare's health care protocols, or to the needs of a specific patient.

The patient turn recognition feature is carried out by controller 56. Controller 56 determines whether a patient has turned or not based upon the outputs of load cells 36, or other sensors that controller 56 may be in communication with. Such other sensors may include infrared sensors, cameras, ultrasonic, patient interface pressure sensors, or still other sensors. If relying solely upon load cells 36, controller 56 is programmed to monitor the center of gravity of the patient from the moment he or she enters the patient support surface 28. As can be seen in FIG. 18, when the patient is on his or her right side (position 172), the patient's center of gravity will typically be offset (in a lateral or side-to-side direction) toward a right side 182*a* of the patient support surface 28 (located underneath mattress 170). When the patient is lying on his or her back (position 174), the patient's center of gravity will tend to be near the center (laterally) of the patient support surface 28. Further, when the patient is lying on his or her left side (position 176), the patient's center of gravity will tend to be offset laterally toward a left side 182*b* of the patient support surface 28. By continuously monitoring these locations of the patient's center of gravity, measurement subsystem 54 (or 54*a* or 54*b*) is able to detect when a patient turns, what type of turn it was, and the duration of each of the turns. This information is stored in patient turn log, one example of which is shown in FIG. 19.

FIG. 19 illustrates a screen shot 184 of a patient turn log that may be kept by any of measurement subsystems 54, 54*a*, or 54*b*. Screen shot 184 is displayed by controller 56 on display 64. As can be seen, the patient turn log includes a listing of patient turn events 186 that have been detected by the measurement subsystem. In the example shown in FIG. 19, three turn events 186 are shown: one in which the patient turned from his or her back onto his or her left side; another in which the patient returned to lying on his or her back; and another in which the patient turned from his or her back onto his or her right side. While not shown in FIG. 19, screen shot 184 can be modified to include an icon, or other control, for changing the time period of turn events that are displayed thereon, similar to the time range adjustments for the weight log that can be implemented using up and down arrow icons 102 and 104 (see, e.g. FIGS. 7 and 8). In still other embodiments, controller 56 can be programmed to display, alternatively or in addition to screen shot 184, a screen shot having a bar chart of the cumulative amount of time that a patient spends in each turn position. Such a bar chart could be similar to the bar chart of FIG. 17 except that, instead of the bars identifying the cumulative amount of time spent in each different activity level, the bars would identify the cumulative amount of time spent in each different position 172, 174, and 176.

Screen shot 184 includes a weight log icon 82 and an activity log icon 180. Pressing on weight log icon 82 will cause controller 56 to switch to displaying the weight log, such as that shown in FIGS. 7 and 8, (if a weight log feature is included with the patient support apparatus). Similarly, pressing on activity log icon will cause controller 56 to switch to displaying the activity log, such as that shown in FIG. 17 (if the activity log feature is also included with the patient support apparatus). The inclusion of icons 82 and 180 on screen shot 184 is therefore not intended to suggest that any patient support apparatus having the turn recognition feature also must have both the weight logging feature and/or the activity logging feature. These three features are separate, and a patient support apparatus may include only one of these features, two of them, or all three of them, depending on the particular embodiment. Still further, in some embodiments where all three features are included, controller 56 may be configured to keep a common log that includes patient activity events, weight events, and turn events, rather than three separate logs.

Figure 20:
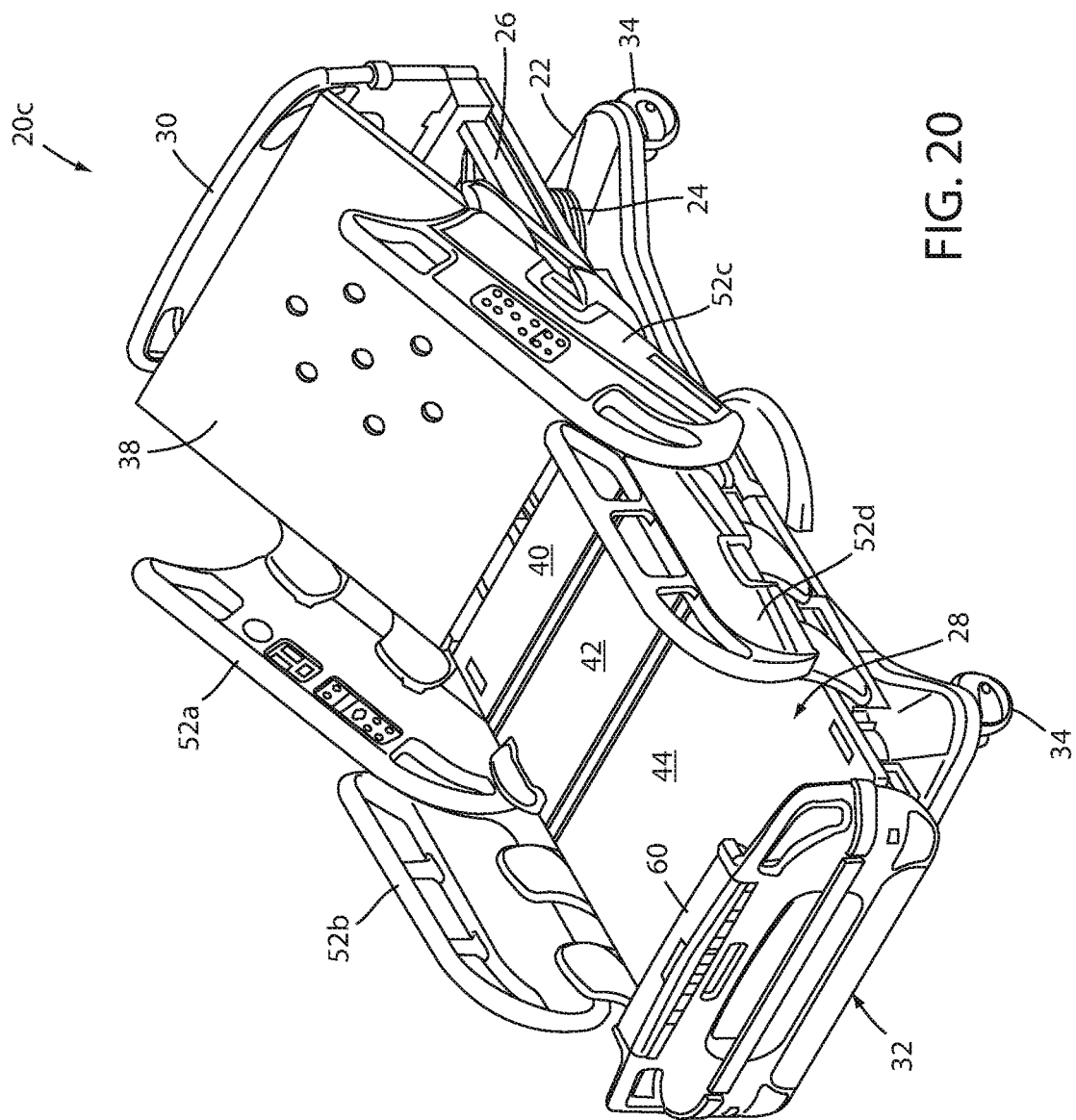
FIG. 20 is a perspective view of another patient support apparatus that may include any one or more of the various features and functions described herein.

Another embodiment of a patient support apparatus 20*c* is shown in FIG. 20. Those components of support apparatus 20*c* that are common to support apparatuses 20, 20*a* and/or 20*b* are labeled with the same reference number and operate in the same manner described previously, unless other indicated below. As shown, patient support apparatus 20*c* includes a vital signs sensor 134 that is used to detect one or more vital signs of a patient positioned on patient support surface 28. Vital signs sensor 134, in the embodiment of FIG. 20, is incorporated into a head siderail 52 of patient support apparatus 20*c*. In some embodiments, patient support apparatus 20*c* includes two vital sign sensors 134—one incorporated into a first siderail 52 positioned on a first side of patient support apparatus 20*c*, and one incorporated into a second siderail 52 positioned on a second side of the patient support apparatus opposite the first side. In still other embodiments, additional vital sign sensors 134 can be included in patient support apparatus 20*c*, and/or vital sign sensors 134 may be positioned in other locations besides siderails 52.

In the embodiment shown in FIG. 20, vital sign sensor 134 is attached to, or incorporated into, right head siderail 52*a*. Vital sign sensor 134 may alternatively be incorporated into left head siderail 52*c*. Due to the operation of vital sign sensor 134, in some embodiments, it may be desirable to avoid positioning vital sign sensor 134 in either of foot end siderails 52*b* or 52*d*.

In one embodiment, vital sign sensor 134 is a non-contact biomotion sensor that measures movement of a patient's torso and derives therefrom the patient's heart rate and/or respiration rate and/or movement levels. In one embodiment, the biomotion sensor 134 emits a series of radio-frequency pulses at 5.8 Gigahertz toward the patient's torso and detects the echoes of these signals as they are reflected from the patient's torso. The echoes are used to determine movement of the patient's chest wall, which is converted into measurements of the patient's breathing rate, heart rate, and/or positional changes. One type of biomotion sensor that may be used as vital sign sensor 134 is a biomotion sensor sold under the trade name SleepMinder by BiancaMed (owned by ResMed) of Dublin, Ireland. Another type of biomotion sensor that may be used as vital sign sensor 134 is a Kai Continuous Respiratory Rate Monitor or Kai Spot Model KMS 200 Respiratory Rate Spot check monitor, both of which are marketed by Kai Medical, Inc. of Honolulu, Hi. Devices other than these specific ones may also be used at vital sign sensor 134.

Vital sign sensor 134 may alternatively be an non-contact ultrasonic sensor that determines a patient's heart rate, breathing rate, and/or movement by emitting ultrasonic waves toward the patient's abdominal walls and/or chest cavity, which are then reflected back to the sensor 134 and detected. The detection of the reflected waves provides an indication of the movement of the patient's abdomen and/or chest cavity, which can be used to determine respiration rate, heart rate, and/or overall movement levels. One such type of ultrasonic sensor is disclosed in the following journal article: Se Dong Min et al., "Noncontact Respiration Rate Measurement System Using an Ultrasonic Proximity Sensor," IEEE Sensors Journal, vol. 10, issue 11, pages 1732-1739 (2010), the complete disclosure of which is hereby incorporated herein by reference.

In still another embodiment, vital sign sensor 134 may be a non-contact sensor that includes a plurality of load cells that are used to detect the downward forces exerted by a patient supported on patient support surface 28. One method and arrangement for detecting vital signs using load cells is disclosed in commonly assigned U.S. Pat. No. 7,699,784 issued to Wan Fong et al., and entitled SYSTEM FOR DETECTING AND MONITORING VITAL SIGNS, the complete disclosure of which is hereby incorporated herein by reference. When using load cells to detect vital signs, such load cells are typically positioned adjacent each corner of the patient support surface 28 and cumulatively sense the entire weight of a patient, other person, and/or objects positioned on the patient support surface 28, as well as downward forces due to breathing and the patient's heart rate. Other examples of the positioning and arrangement of load cells, if used on patient support apparatus 20c, can be found in commonly assigned U.S. Pat. No. 7,690,059, issued to Lemire et al., and entitled HOSPITAL BED, which is incorporated herein by reference in its entirety, as well as in the Stryker Maintenance Manual for the Model 3002 S3 MedSurg Bed, which has also already been incorporated herein by reference. Other constructions of the frames and positions of the load cells may also be used.

In still other embodiments, vital sign sensor may be modified to include the ability to sense a patient's ECG and/or EEG signals using any known manners of measuring these items.

Regardless of the specific configuration of vital sign sensor 134, vital sign sensor 134 communicates its detected signals indicative of heart rate and/or breathing rate to controller 56 positioned on board patient support apparatus 20c. Controller 56 receives the outputs of vital sign sensor 134 and processes them to determine the heart rate and/or breathing rate of a patient positioned on patient support surface 28. Controller 56 further records and analyzes the heart beat and/or respiration rate to make a determination as to whether or not the patient positioned onboard the patient support surface 28 is asleep or awake. Such processing can be carried out in known manners that correlate reduced periods of heart rate and/or breathing rate to periods of sleep. In one embodiment, the analysis of the heart period variability is used to determine which state of sleep a patient is in—REM or non-REM. Such techniques are known in the art, as well as other techniques for correlating heart rate and/or breathing rates to periods of sleep or wakefulness, as would be known to one of ordinary skill in the art.

Figure 21:
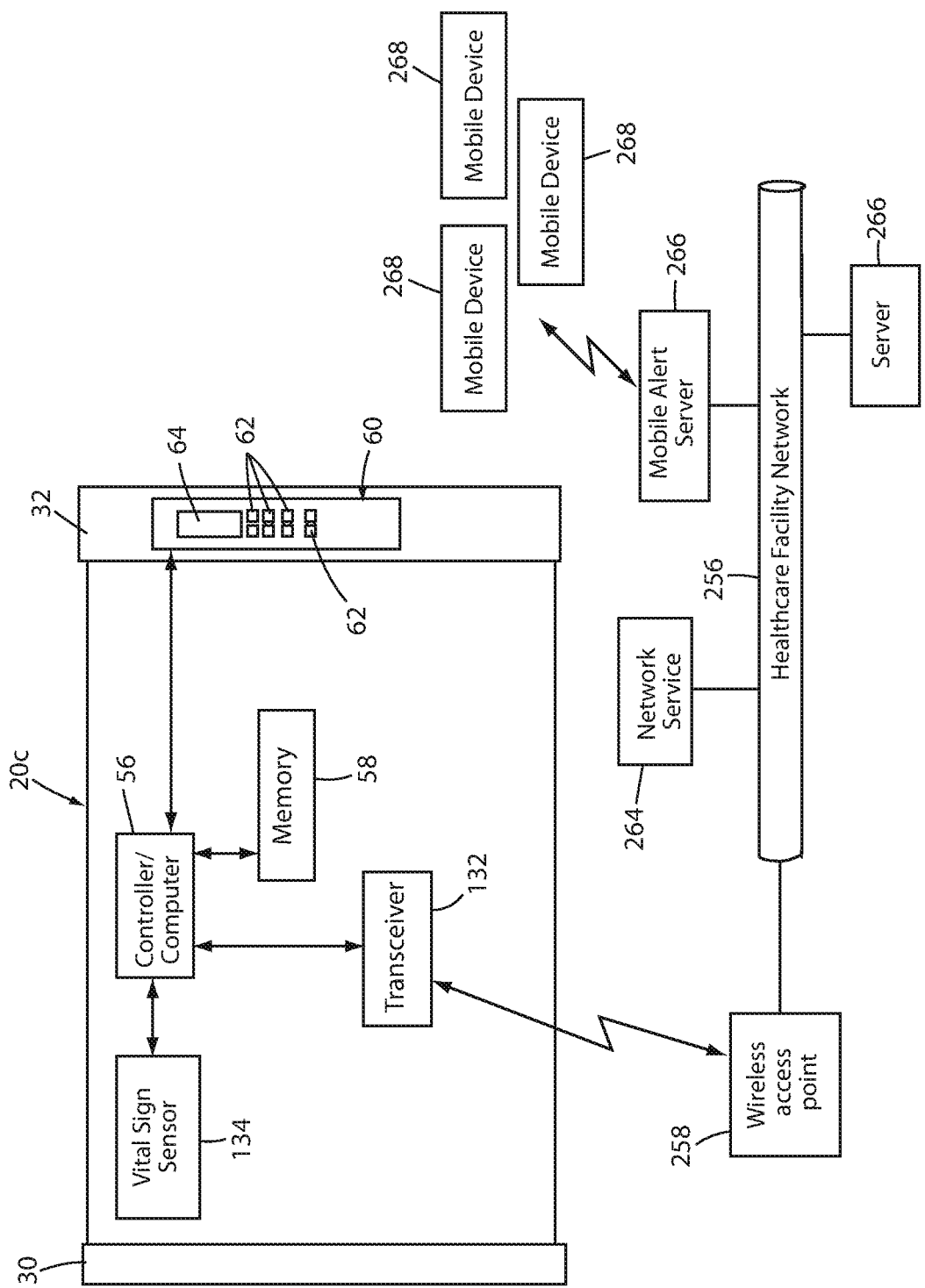
FIG. 21 is a plan view diagram of the patient support apparatus of FIG. 20 shown interacting with a healthcare facility computer network.

As shown more clearly in FIG. 21, controller 56 communicates with additional electronic components besides vital signs sensor 134, such as a memory 58, a wireless transceiver 132, and a user interface 60. Memory 58 stores the instructions used by controller 56 to carry out its algorithms, as well as the data gathered from vital signs sensor 134, both before and after processing. Wireless transceiver 132 is used by controller 56 for forwarding selected information gathered from vital signs sensor 134 to other devices, such as a hospital Ethernet, or another recipient. In one embodiment, transceiver 132 is a WiFi radio capable of communicating with a wireless access point 258 of the hospital Ethernet 256 in accordance with IEEE 802.11 standards (e.g. 802.11(b), 802.11(g), and/or 802.11(n)), or in accordance with other standards.

User interface 60 includes a plurality of buttons 62 that a caregiver presses in order to control various features of the patient support apparatus 20c, such as, but not limited to, raising and lowering the height of frame 26, pivoting one or more of support surface sections 28, turning on and off a brake (not shown), controlling an exit alert system that may be integrated into the support apparatus 20c, and interacting with controller 56 for both controlling controller 56 and viewing the data processed by controller 56, or the results of such processed data. In the embodiment illustrated in FIG. 21, user interface 60 further includes a display 64 integrated therein. Display 64 is a touchscreen display capable of displaying text and/or graphics and sensing the location that a user's finger touches the display, although it will be understood that display 64 could be modified to be a normal LCD display without touchscreen capabilities that used hard or soft buttons to interact therewith, or still other types of displays.

In one embodiment, when controller 56 determines that a patient has awoken or has fallen asleep, controller 56 sends a "patient awake" or "patient asleep" message to transceiver 132 that is communicated wirelessly to either a network service 264 or a server 266 on healthcare facility network 256. In the embodiment shown in FIG. 21, controller 56 sends the message via transceiver 132 to wireless access point 258, which then forwards the message to a mobile alert server 266. Mobile alert server 266 may be a conventional, commercially available server that forwards communications it receives to one or more electronic mobile devices 268 that are worn or carried by healthcare personnel, such as nurse, nurse assistants, doctors, etc. The mobile electronic devices 268 may be any one or more of the following: smart phones, computer laptops, computer netbooks, computer tablets, personal digital assistants, or the like. By communicating a "patient awake" or "patient asleep" message from controller 56 to one or more mobile devices 268, caregivers will be notified of the current sleep status of the patients under their care. This will give the caregivers real time information about the status of their patients, which can allow them to more efficiently organize their nursing duties. For example, the caregivers can delay—to the extent possible—perform those nursing duties on patients who are currently sleeping and would otherwise be awoken if the duties were performed. Similarly, to the extent possible, the caregivers can prioritize their nursing duties by performing them on those patients who are currently awake and will therefore not have to suffer from being awoken during the implementation of those nursing duties.

In another embodiment, controller 56 processes the outputs of one or more vital signs sensors 134 to determine whether a patient who is currently sleeping is likely to wake up in the near future. Controller 56 accomplishes this by looking for characteristic increases in a patient's heart rate and/or breathing rate that are indicative of a patient arousing from a sleep state. Such characteristics are known to a person of ordinary skill in the art. When controller 56 determines that a sleeping patient is likely to awaken due to the changes in his or her heart rate and/or breathing rate, controller 56 sends a message to network 256 (via transceiver 132 and access point 258) indicating that the patient is likely to awaken soon. This message is picked up by mobile alert server which then forwards it to the mobile devices 268 of the one or more caregivers responsible for caring for that particular patient. Depending upon whether or not that particular patient is a fall risk or not, the caregivers will thereby receive advance warning that a patient is waking up, and very well may be likely to exit the patient support apparatus 20c soon. This is particularly true for situations where the patient is awakening to use the restroom. By giving the caregiver(s) advance notice of the likely awakening of a patient, the caregiver(s) can, as appropriate, travel to the patient's room and arrive either before the patient awakens, or shortly thereafter, thereby reducing the chances that the patient will try to leave the patient support apparatus unassisted, and consequently thereby reducing the chances of a patient fall.

Figure 22:
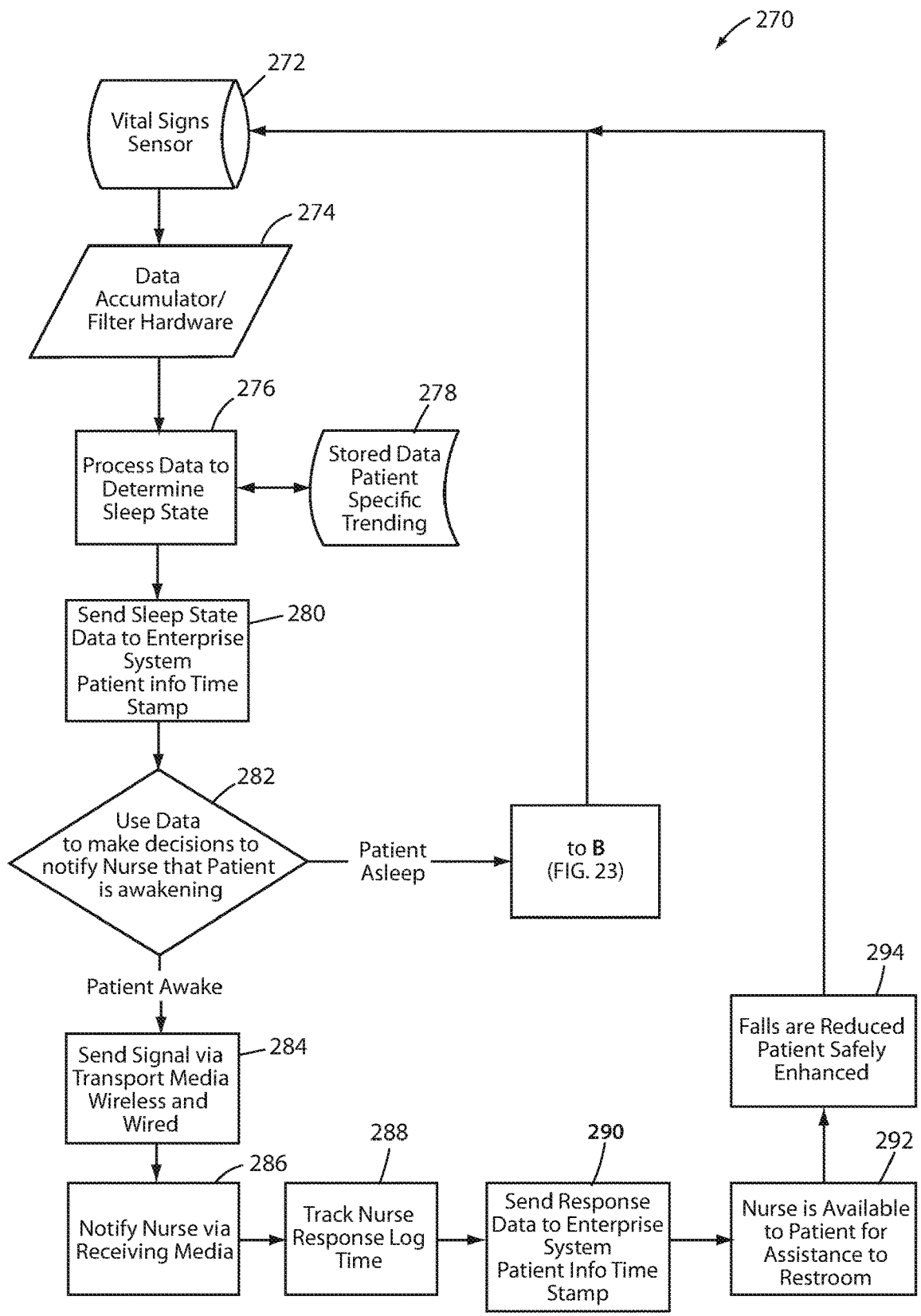
FIG. 22 is a flowchart of a patient monitoring algorithm that may be carried out using any of the patient support apparatuses described herein.

FIG. 22 illustrates a patient care process 270 that is partially carried out by patient support apparatus 20c, partially carried out by components of healthcare facility network 256, and partially carried out by one or more caregivers. Patient care process 270 begins at a first step 272 where data from one or more vital sign sensors 134 is gathered. At subsequent step 272, the gathered data is filtered, as necessary, and accumulated. Step 272 may be carried out by appropriate electronics (e.g. filters) upstream of controller 56, or it may be carried out internally by controller 56, or it may be carried out by a combination of controller 56 and other electronics.

After filtering and accumulation of the data from vital signs sensor 134 is accomplished at step 274, controller 56 carries out step 276 in which is processes the filtered and accumulated data to determine the sleep state of the patient. The sleep state, in some embodiments, simply refers to whether the patient is asleep or awake. As noted, however, is other embodiments, the sleep state may also include whether or not the patient is likely to awaken soon. In still other embodiments, the sleep state includes an indication of whether or not the patient, when sleeping, is in a state of REM (rapid eye movement) sleep or non-REM sleep.

The determination of the patient's sleep state at step 276 is carried out by comparing the current data from vital signs sensor 134 to a database 278 of data from that same patient. In other words, database 278 includes the past readings of the patient's vital signs, including analyses of trends in those past readings. This data is used to analyze the current vital sign data coming from the patient through vital sign sensor 134. Such analysis includes, but is not limited to, analyzing the trends in the patient's breathing rate and/or heart rate. For example, the breathing rate and heart rate of the patient are computed and stored. Further, the rate of change in the breathing rate and heart rate are computed and stored. Sharp changes in the rate of change of either the breathing rate or heart rate can be used as indicators of a patient's imminent waking, or for identifying sleep status. Database 278 is, in one embodiment, maintained in memory 58 on board patient support apparatus 20c.

At step 280, controller 56 optionally sends the processed data about the patient to a remote enterprise system. Such transmitted data is sent with a time stamp so that the recipient enterprise system is able to correlate the data to time. The enterprise system may be a network service 264 or a server 266 that are local to the healthcare facility network 256, or it may be a network service or server that is located remotely from facility network 256 (e.g. in the cloud) and in communication with network 256 via the Internet, or other means. For purposes of the following description, it will be assumed that network service 264, which is in local communication with network 256, is the recipient of the data transmitted at step 280, although, as noted, it will be understood that this is only for purposes of description and that such data may be stored and processed elsewhere.

In one embodiment, network service 264, after receiving the sleep status data from a particular patient support apparatus 20c, will determine whether to notify mobile alert server 266 if the patient's sleep status has changed (either from awake to asleep, or asleep to awake). Network service 264 may be configurable by the healthcare facility to control whether it forwards such a notification to mobile alert server 266. In one embodiment, every time a patient's sleep status changes, network service 264 will notify mobile alert service 266 so that messages indicating the change in sleep are sent to the mobile devices of the one or more caregivers responsible for that particular patient. As was noted previously, in another embodiment, patient support apparatus 20c may alternatively send such messages directly to mobile alert server 266, bypassing network service 264.

At step 282, the processed vital sign (and sleep) data is used to determine whether a sleeping patient is about to wake up or not. Step 282 is, of course, only performed if the patient is currently sleeping on patient support apparatus 20c. If the patient is awake, controller 56 returns back to step 272, where it continues to gather vital sign data, process it, and store it for comparison purposes. Step 282 is carried out by either controller 56 locally on board patient support apparatus 20c, or by network service 264 remote from patient support apparatus 20c. As was noted previously, the determination of whether or not a sleeping patient is about to wake up or not is made by examining changes in the patient's heart rate and/or breathing rate.

If it is determined at step 282 that a patient is likely to awaken soon, control passes to step 284 (FIG. 22). If it is determined at step 282 that the sleeping patient is not likely to awaken soon, control passes to the steps generically identified with the label B in FIG. 22 which are spelled out in detail in FIG. 23.

Turning to step 284, either controller 56 or the enterprise network service 264 sends a message to mobile alert server 266 (via network 256) indicating that a patient is likely going to awaken soon. The content of this message is wirelessly forwarded at step 286, as has been noted, by mobile alert server 266 to the electronic mobile device 268 of the one or more caregivers who are responsible for the patient in patient support apparatus 20c.

In the embodiment shown in FIG. 22, enterprise network service 264 keeps track of the amount of time it takes for the notified caregiver(s) to respond to the message indicating that a patient is about to awaken. This is done at step 288. The amount of time it takes for the caregiver to respond can be measured in a variety of different ways. For example, the caregivers typically will be wearing an ID badge, tag, or the like, that is tied to a conventional and commercially available real-time locating system that healthcare facilities commonly have on their premises. Further, such a real time locating system is commonly in electronic communication with the healthcare facility network 256. Enterprise network service 264 can monitor the response time of a caregiver by monitoring the location of the corresponding caregiver—from the data provided over network 256 by the real time locating system—and counting the amount of time that elapses before the caregiver enters the room in which patient support apparatus 20c is positioned. In another embodiment, patient support apparatus 20c may be configured such that a manual pressing of one or more buttons 62, or touching of the display 64, is required by the caregiver in order to turn off the alerting of potential imminent patient wake-up. When so configured, patient support apparatus 20c notifies network service 264 that such a manual shutting down of the alert has taken place. The time at which network service 264 receives this notice provides an indication of the caregiver response time.

At step 290, the caregiver response time is sent to enterprise network service 264 (if the caregiver response time was determined by an entity other than enterprise network service 264). Enterprise network service 264 records the response time in a database that is maintained for all patient support apparatuses 20c in that healthcare facility. This information is made available to appropriate personnel of the healthcare facility for tracking and evaluation purposes.

At step 292, the notified caregiver has arrived in the room in which patient support apparatus 20c is positioned and is available to assist the patient, should he or she desire to get out of patient support apparatus 20c. If the patient has awoken due to reasons that don't require him or her to exit patient support apparatus 20c, then the caregiver can assist the patient, as appropriate, and return to performing his or her other duties after assisting that patient. Because the visit by the caregiver to the patient's room will occur close to the time the patient is awakening, or shortly after the patient has already awoken, the visit will not cause an interruption the patient's sleep, and therefore should not disturb the patient unnecessarily.

Further, if the patient has awoken because he or she desires to exit patient support apparatus 20c, such as for example, because the patient desires to visit the rest room, then the recent arrival of the caregiver at step 292 will allow the caregiver to assist the patient out of and into patient support apparatus 20c. The risk of a patient fall is therefore reduced, as indicated at step 294. After the caregiver has assisted the patient, he or she will leave the room and patient care process 270 will begin again at step 272.

Figure 23:
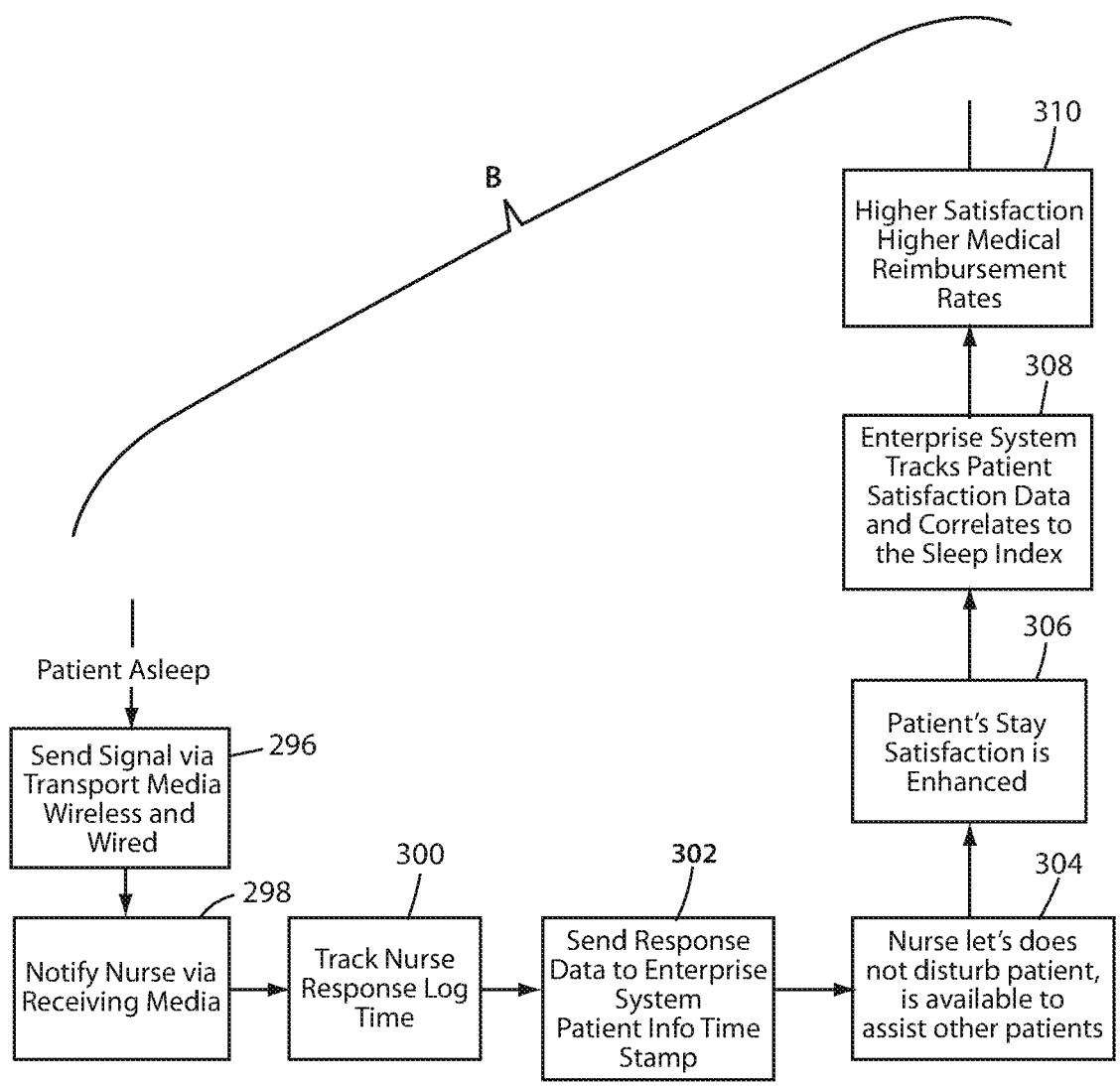
FIG. 23 is a continuation of a portion of the flowchart of FIG. 22.

Turning to FIG. 23, if it is determined at step 282 that a patient is asleep and not likely to awaken soon, then control passes to step 296 (FIG. 23). At step 296, a message is sent to mobile alert server 266 indicating that the patient is sleeping. This message is sent either by controller 56—in one embodiment—or by enterprise network service 264—in another embodiment. The sending of this message may also be omitted, in some embodiments, if the sender has recently sent a similar message within a threshold amount of time. In other words, if controller 56 or network service 264 has determined that the patient is sleeping only several minutes ago, the sending of another message indicating that the patient is still asleep may be omitted. In this manner, the caregiver is not overloaded with messages that repetitively inform him or her that a patient is sleeping. The frequency at which the "patient asleep" message is sent at step 296 is, in one embodiment, configurable by the healthcare administrator, either through user interface 60 of patient support apparatus 20c, or through network access to enterprise network service 264.

At step 298 (FIG. 23), mobile alert server 266 sends one or more wireless messages to one or more mobile electronic devices 268 indicating that the patient is asleep. At step 300, enterprise network service 264 monitors whether or not any caregivers associated with the patient in patient support apparatus 20c enter the room of that patient and potentially interrupt the patient's sleep. This monitoring is accomplished, in one embodiment, via communication with a conventional real time locating system that tracks caregiver movements and that shares such data with clients on healthcare facility network 256, such as enterprise service 264. In another embodiment, the detection of a caregiver's presence or absence is performed by sensors positioned on-board patient support apparatus 20c that are able to detect the nearby presence of RF ID tags, badges, or the like, that are carried by caregivers. One example of sensors that may perform this task are the near field sensors disclosed in commonly assigned, U.S. patent application Ser. No. 13/802,992 filed Mar. 14, 2013 by applicants Michael Hayes et al. and entitled COMMUNICATION SYSTEMS FOR PATIENT SUPPORT APPARATUSES, the complete disclosure of which is hereby incorporated herein by reference.

At step 302, data indicating whether or not a caregiver has entered the room of the patient sleeping on patient support apparatus 20c is forwarded to network service 264 (to the extent network service 264 is not monitoring this information directly). This data is stored and made available to appropriate personnel who can view the data to make process control decisions at the corresponding healthcare institution to help ensure, to the extent feasible, that sleeping patients are not unduly awakened.

As indicated by step 304, when a caregiver receives a notification via their associated mobile electronic device 268 that a patient is asleep, this may give the caregiver the ability to assist other patients who are awake thereby avoiding the need to wake up sleeping patients. Further, as indicated at step 306, by reducing the number of sleep interruptions of one or more patients, the quality of the patient's stay at the healthcare facility will likely improve. At step 308, enterprise network service 264 correlates patient satisfaction data (which may be gathered through patient surveys) with an index indicative of the patient's sleep (such as the number of interruptions to the patient's sleep). By reducing the number of sleep interruptions, the patient satisfaction index would likely be expected to increase, which can have financial benefits to the healthcare facility, which is indicated in step 310. After step 310, control returns to step 272 (FIG. 22).

It will be understood that various modifications to patient care process 270 may be made. For example, in one embodiment, patient care process 270 only monitors sleep and wakefulness, and does not monitor or detect imminent wake-ups. In another embodiment, patient care process 270 monitors imminent wakeups in addition to sleep state. In still another embodiment, quality of sleep is monitored, assessed, and stored for later review. In still another embodiment, enterprise service 264 uses the patient's sleep data (e.g. duration, number of interruptions, quality of sleep) to compute a sleep assessment. Such an assessment may be scored numerically on any suitable scale. The assessment is retained and made available to appropriate personnel to gauge the quality of the patient's rest while at the healthcare facility. Still other modifications may be made.

Figure 24:
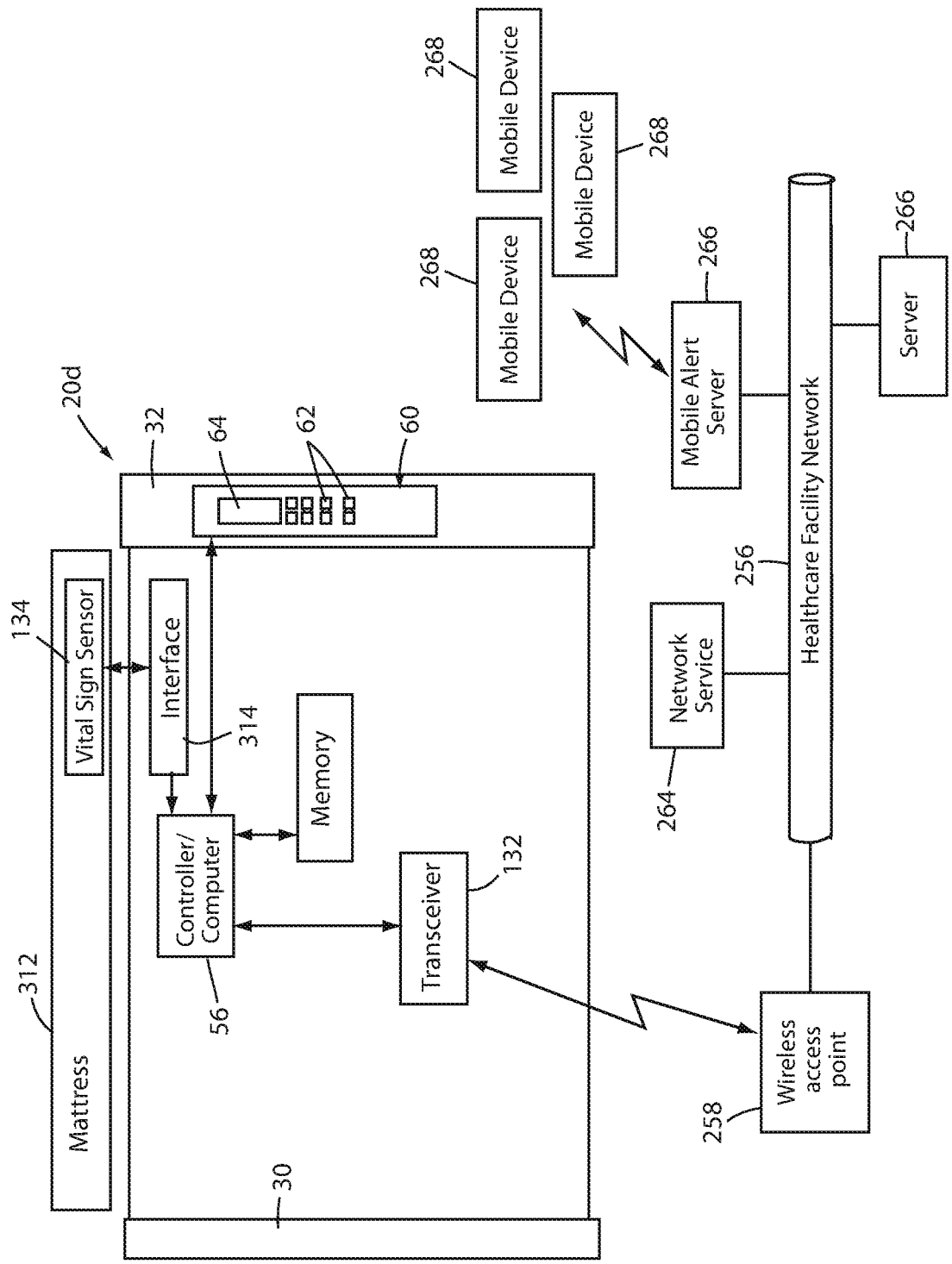
FIG. 24 is a plan view diagram of a patient support apparatus according to another embodiment shown interacting with a healthcare facility computer network.

FIG. 24 illustrates an alternative embodiment of a patient support apparatus 20d. Those components of patient support apparatus 20d that are the same as those found in patient support apparatus 20, 20a, 20b, and/or 20c are labeled with the same number. Such common components operate in the same manner as has been described, unless indicated otherwise below. Patient support apparatus 20d differs from support apparatus 20c in that vital signs sensor 134 is positioned inside of a mattress 312, rather than integrated directly into the patient support apparatus. In one embodiment, vital sign sensor 134 may include one or more air pressure sensors that detect a patient's breathing and heart rate due to the physical compressions on the mattress caused by the patient's breathing and heart beating. Such physical compressions change the air pressure inside the one or more air bladders positioned inside the mattress 312, which are thereby detected by one or more conventional air pressure sensors positioned inside of mattress 312. As was noted above, one such mattress that may be used to detect a patient's vital signs in this manner is disclosed in commonly assigned U.S. patent application Ser. No. 13/836,813 filed Mar. 15, 2013 by applicants Patrick Lafleche et al., and entitled INFLATABLE MATTRESS AND CONTROL METHODS, the complete disclosure of which has already been incorporated herein by reference.

Mattress 312 communicates with patient support apparatus 20d via an interface 314 positioned on board patient support apparatus 20d. Interface 314 may be a wired interface that electrically coupled mattress 312 to patient support apparatus 20d (including controller 56), or it may be a wireless interface that makes such a connection. One example of a suitable wireless interface is disclosed in commonly assigned U.S. patent application Ser. No. 13/296,656 Nov. 15, 2011 by applicants Guy Lemire et al. and entitled PATIENT SUPPORT WITH WIRELESS DATA AND/OR ENERGY TRANSFER, the complete disclosure of which is hereby incorporated herein by reference.

Once the vital sign data from sensor 134 inside mattress 312 is communicated to controller 56, operation of patient support apparatus 20*d* and patient care process 270 takes place in the same various manners that have been described previously.

In still another alternative embodiment, the vital sign data gathered by vital sign sensor 134 used to determine the sleep status of a patient may be supplemented with video data gathered from a video system that monitors the patient by analyzing the patient's movement, facial expressions, and gestures. One such system for gathering such video data and processing it is disclosed in commonly assigned, U.S. patent application Ser. No. 13/242,022 filed Sep. 23, 2011 by applicants Richard Derenne et al. and entitled VIDEO MONITORING SYSTEM, the complete disclosure of which is hereby incorporated herein by reference. The images taken by such a video system may be processed to determine patient movement (or lack thereof), expressions, gestures, etc. and use such information in combination with the vital sign data to determine any one or more of the patient's sleep state, quality of sleep, imminent patient exit, etc.

Figure 25:
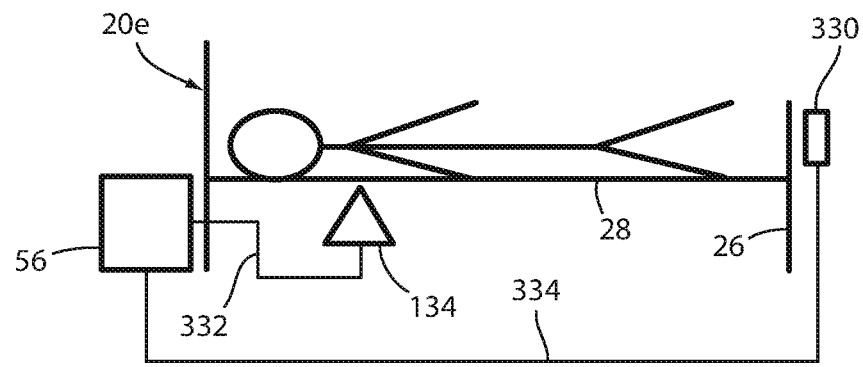
FIG. 25 is a side elevational diagram of a person support apparatus according to one embodiment of the invention.

A person support apparatus 20*e* according to yet another embodiment is shown in FIG. 25. Person support apparatus 20*e* includes a frame 26 and a support surface 28 for supporting a person thereon. Person support apparatus 20*e* further includes at least one vital sign sensor 134, a controller 56, and an indicator 330. Vital sign sensor 134 is either mounted to the person support apparatus 20*e* or positioned in suitable proximity to person support apparatus 20*e* so as to enable it to monitor at least one vital sign of a person while the person is supported on support surface 28. In one embodiment, vital sign sensor 134 includes both a respiration rate sensor and a heart rate sensor. In other embodiments, vital sign sensor 134 includes only a single vital sign sensor; while in still other embodiments, vital sign sensor 134 includes more than two vital sign sensors.

Vital sign sensor 134 is in electrical communication with controller 56 via a first communication link 332. First communication link is, in one embodiment, a wire or cable that enables electrical or optical signals to be transmitted between vital sign sensor 134 and controller 56. In other embodiments, communication link 332 is a network connection, such as a Controller Area Network (CAN) connection, a Local Interconnect Link (LIN) connection, or other type of network connection. Regardless of the specific type of connection, vital sign sensor 134 forwards signals to controller 56 that are indicative of the vital sign measured by sensor 134. Controller 56 uses these vital sign signals to determine a sleep state of the person supported on support surface 28.

Controller 56 is programmed to utilize the outputs of vital sign sensor 134 to determine the sleep status of the person on support surface 28. In one embodiment, controller 56 determines only two sleep states: asleep and awake. In another embodiment, controller 56 determines more than two sleep states. For example, in one embodiment, controller 56 is programmed to determine the five following sleep states: awakening, awake, falling asleep, asleep, and deep sleep. In the awakening state, the person's vital signs are showing that the person is transitioning from either the asleep or deep sleep state to the awake state. In the falling asleep state, the person's vital signs are showing that the person is transitioning from the awake state to either the asleep or deep sleep state. In one embodiment, the sleep state refers to the person being in a REM (rapid eye movement) sleep state, and the deep sleep state corresponds to any non-rapid eye movement sleep (NREM), whether in stages 1, 2, or 3. These definitions can, of course, be changed to refer to different categories of sleep. For example, in another embodiment, the deep sleep state corresponds to only stage 3 slow-wave sleep, as defined by the American Academy of Sleep Medicine, while the asleep state refers to all other sleep states (except for awakening, falling asleep, and awake). In still other embodiments, the sleep states are defined according to still other definitions.

Controller 56 determines the sleep state of the person by recording and analyzing the person's vital signs. In one embodiment, the sleep state is determined by comparing the person's current vital signs with a record of the person's past vital signs from a prior period. For example, controller 56 stores the person's heart beat and/or respiration rate over a period of time and then compares the stored data to the person's current heart rate and/or respiration rate to make a determination as to whether or not the person positioned onboard the support surface 28 is asleep, awake, or in any one or more of the other sleep states mentioned above. Such processing can be carried out in known manners that correlate reduced periods of heart rate and/or breathing rate to periods of sleep. In one embodiment, the analysis of the heart period variability is used to determine which state of sleep a person is in—REM or non-REM. Such techniques are known in the art, as well as other techniques for correlating heart rate and/or breathing rates to periods of sleep or wakefulness, as would be known to one of ordinary skill in the art.

Controller 56 is in electrical communication with indicator 330 via a second communication link 334. In the embodiment shown in FIG. 25, communication link 334 is a wired link and indicator 330 is supported on person support apparatus 20*e*. In other embodiments, communication link 334 is a wireless communication link and indicator 330 is positioned at a location separate from person support apparatus 20*e*. Regardless of its location, indicator 330 is a device that is adapted to provide an aural and/or visual indication to one or more persons within the vicinity of person support apparatus 20*e*. When configured to emit only sound, indicator 330 may be any one or more of a buzzer, a beeper, a speaker, or other device configured to emit sound. When configured to emit light, indicator 330 may be any combination of one or more incandescent lights, fluorescent lights, liquid crystal displays, touch screens, light emitting diodes, or other sources of light.

Indicator 330 is configured to emit a sound and/or a light when one or more triggering events occur on or within the vicinity of person support apparatus 20*e*. For example, in one embodiment, the triggering event is the expiration of a time limit. The expiration of the time limit can result from multiple different scenarios, such as, but not limited to, an alarm clock reaching its programmed alarm time, or a medical care timer expiring that is set for carrying out one or more patient care protocols for a patient positioned on support surface 28 (e.g. the alarm may issues when it is time for a patient to be turned so as to reduce the likelihood of bed sores developing, when it is time for a dressing on the patient to be changed; when it is time for the patient to be bathed; when it is time for medication to be administered, or for vital signs to be measured by a caregiver; or for any other reason related to the care of a patient on support apparatus 20*e*).

The triggering event may also take on a variety of other forms, some of which are dependent upon the particular features and/or design of person support apparatus 20*e*. For example, in some embodiments, the triggering event is the pressing of one or more buttons on the person support apparatus 20*e*. In some embodiments, person support apparatus 20*e* is be designed such that the pressing of certain buttons on person support apparatus 20e normally cause indicator 330 to beep, buzz, or emit another sound when they are pressed in order to provide the user with aural feedback that those buttons have been pressed, or to give the user information that corresponds to the buttons being pressed. For example, indicator 330 may normally emit a sound when a button that moves a particular component of the bed has been pressed and the movement of that component has reached one of its limits. Alternatively, a button may be pressed that relates to a function of the bed that would normally cause indicator 330 to emit voice instructions relating to that particular function. Other configurations are also possible where the pressing of one or more buttons, icons, switches, or the rotation of one or more dials or cranks, or the physical movement of a component of the person support apparatus 20e, or the like, normally causes indicator 330 to emit a sound or light, and any one of those situations could constitute a triggering event.

Still other triggering events are possible, such as the playing of music on or adjacent to person support apparatus 20e. For example, some person support apparatuses 20e include a radio or other electronic audio playback device (e.g. MP3 player) that is built into the support apparatus. Such a radio or audio playback device constitutes one form of indicator 330, and the activation of this radio or audio playback device constitutes one type of triggering event. In this situation, controller 56, as discussed below, causes cessation of this audio playback when it is determined that the person on support surface 28 has entered any one or more of the sleep states. In addition to audio playback devices, the indicator 330 includes a television, or any other entertainment device, and the triggering event will include the activation of indicator 330. Whether indicator 330 is a television, radio, or any other type of entertainment device, it is not necessary that it is incorporated into person support apparatus 20e, but instead could be positioned anywhere within the vicinity of person support apparatus 20e. Upon detecting that the person is in a sleep state, controller 56 will automatically change the volume (e.g. mute or reduce) of the television, radio, or other type of entertainment device, or will completely shut off the radio, television, or other entertainment devices. Still other triggering events are possible, some of which will be discussed below, as well as different forms of indicator 330.

Regardless of the triggering event that causes the aural and/or visual indication to be emitted by indicator 330, controller 56 is configured to allow a user to change the manner in which indicator 330 responds to the triggering event based upon the sleep status of the person on support surface 28. More specifically, controller 56 is configured to allow a user to change how indicator 330 operates so as to reduce the intensity and/or frequency of disturbances to a person on support surface 28 who is sleeping, or who is falling asleep or in a deep sleep state. For example, controller 56 allows the user to completely mute a sound that would otherwise be emitted from indicator 330 when the person is asleep. Alternatively, controller 56 allows the user to reduce the volume of one or more sounds. In at least one embodiment, indicator 330 is responsive to multiple different types of triggering events, and controller 56 is configured to allow a user to customize which the response of indicator 330 for each of the different triggering events.

In addition to changing the volume of indicator 330, controller 56 is also adapted to allow the user to change the character of the response of indicator 330, if the user desires to do so. For example, controller 56 allows a user to change what would otherwise be an aural indication emitted by indicator 330 to be a visual indication when the person is asleep. Controller 56 also allows a user to change what would normally be a visual indication having a first light intensity to be an altered visual indication having a reduced visual intensity. In this manner, by reducing or eliminating sounds, and/or by reducing or eliminating lights, the chances for disrupting a sleeping person are reduced, thereby enabling the person to obtain a better quality of sleep.

Controller 56 further allows a user to customize the response of indicator 330 to each one of the triggering events. In this manner, indicator 330 can be controlled by the user to behave in a precisely defined manner for each and every one of the triggering events. Thus, for example, if a user deems some triggering events to be high priority events in which the sound or light emitted by indicator 330 is not to be reduced or changed, the user can configure controller 56 to leave the action of indicator 330 unchanged for those triggering events. For other triggering events that the user deems to be lower priority events, the user can customize the behavior of indicator 330 so that the actions it takes are altered. Still further, in some embodiments, person support apparatus 20e includes multiple indicators 330, and controller 56 is configured to allow the user to customize each of the behaviors of the indicators 330 individually for each of the different triggering events. When multiple indicators 330 are included, they may be the same (e.g. two speakers), or they may be different (e.g. a beeper and a speaker, a buzzer and a light, etc.).

In at least one embodiment, indicator 330 is a ringer on a telephone that is adapted to ring when a person dials the phone number corresponding to that telephone. Controller 56 communicates with the telephone via second communication link 334 and sends a control signal to the telephone whenever the person positioned on the person support surface is in a sleep state (any of the asleep, falling asleep, or deep sleep states). The telephone responds to this control signal by reducing the volume of its ringer, or completely muting the ringer. The telephone alternatively or additionally responds by changing its ringer or ring-tone from one that emits a sound to one in which a visual indication (e.g. one or more lights) or a mechanical indication (e.g. vibration of the phone) is provided by the telephone in response to an incoming phone call. Still further, the telephone can be configured to automatically route any incoming phone calls to voice mail in response to the control signal.

Person support apparatus 20e therefore enables a user to configure person support apparatus 20e and/or its environment such that aural and/or visual impediments to a person's sleeping on support surface 28 are reduced or eliminated, thereby enabling the person to achieve a better and more restful sleep. Further, controller 56 handles this configuration of the person support apparatus 20e and/or the nearby environment automatically based upon the determination that the person is sleeping. A second person who is awake therefore does not need to, for example, manually shut off a television, manually turn off a radio, manually mute one or more alarms or alerts, or manually re-configure person support apparatus 20e in such a way that the lights or sounds that it would normally emit are changed to behave in a more sleep-favorable manner. Instead, this happens automatically.

Figure 26:
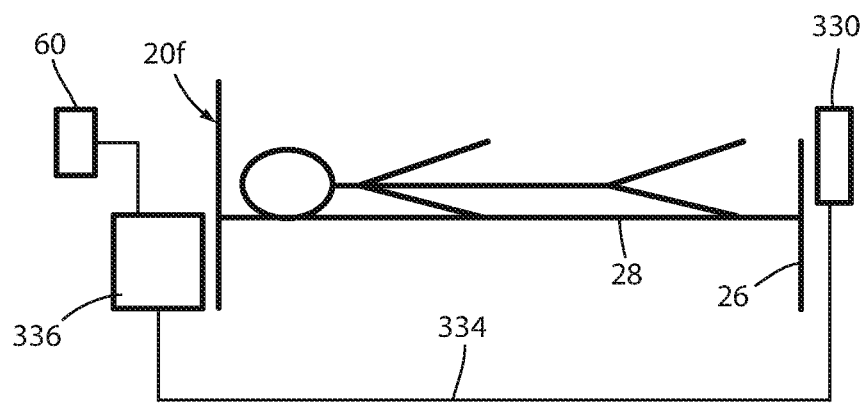
FIG. 26 is a side elevational diagram of a person support apparatus according to a second embodiment of the invention.

FIG. 26 illustrates another embodiment of a person support apparatus 20f. The components of person support apparatus 20f that are common to those of person support apparatus 20e are labeled with common reference numbers and function in the same manner as previously described, and will therefore not be described further. Person support apparatus 20f includes a sleep detector 336 that is adapted to detect whether a person on support surface 28 is asleep or awake (or, in some embodiments, whether the person is in any of the five sleep states mentioned above). Sleep detector 336 differs from vital sign sensor 134 in that it need not necessarily be configured to detect and/or analyze a person's vital signs in order to determine a person's sleep state. For example, in one embodiment, sleep detector 336 includes one or more cameras that are positioned to record visual images of the person supported on surface 28. Sleep detector 336 stores and analyzes these images to determine the amount of movement of the patient, the position of the patient (sitting up, lying down, etc.) and whether the person's eyes are open or shut. Such analysis may be carried out in any known manner, as would be known to one of ordinary skill in the art.

In some embodiments, sleep detector 336 also includes, either in lieu of, or in addition to, one or more cameras, one or more non-visual sensors that monitor movement of the person on support surface 28. For example, in one embodiment, sleep detector 336 includes one or more load cells that are integrated into person support apparatus 20*f* and that detect the load (e.g. weight) that is applied at different locations of support surface 28. In other words, the load cells are arranged to detect the distribution of the person's weight on support surface 28, as well as changes in that distribution. By monitoring these changes in weight distribution, movement of person can be detected and analyzed to determine whether such movement is consistent with one or more of the various sleep states.

In still other embodiments, sleep detector 336 includes one or more vital sign sensors, such as vital sign sensor 134, and the output from the vital sign sensor(s) is used in the determination of the person's sleep state. The use of such vital sign sensors is in lieu of, or in addition to, either or both of the camera and weight distribution sensors (e.g. load cells).

Sleep detector 336 is in communication with a user interface 60, which is any suitable type of user interface, such as an LCD screen, a touch screen, a keypad, a plurality of buttons, switches, or dials, or any combination thereof. User interface 60 allows a user to control the behavior of indicator 330 based on the sleep state of a person on support surface 28. More specifically, user interface 60 allows a user to customize how indicator 330 reacts to one or more triggering events that would otherwise cause indicator 330 to emit one or more sounds and/or lights. Stated alternatively, user interface 60 allows a user to control indicator 330 in any of the same manners that controller 56 can be configured to do so, as discussed above. As with person support apparatus 20*e*, person support apparatus 20*f* may include more than one indicator 330, and user interface 60 allows a user to customize the behavior of each indicator 330 separately from the other for each of the possible triggering events.

FIG. 27 illustrates another embodiment of a person support apparatus 20*g*. The components of person support apparatus 20*g* that are common to those of other support apparatuses described herein (e.g. support apparatuses 20-20*f*) are labeled with common reference numbers and function in the same manner as previously described, and will therefore not be described further. Person support apparatuses 20*g* each include, in addition to components already described above, a transceiver 132 that is adapted to wirelessly communicate, either directly or indirectly, with the other transceiver 132. When communicating directly with each other, transceiver 132 of a first person support apparatus 20*g* sends a wireless message directly to the transceiver 132 of a second person support apparatus 20*g* without having the message pass through any intermediate devices or transceivers. When communicating indirectly with each other, transceiver 132 of the first support apparatus 20*g* sends a wireless message to one or more intermediate devices, and the information in that message is then relayed to the transceiver 132 of the second support apparatus 20*g* via one of the intermediate devices. In some embodiments, the transceivers 132 communicate indirectly by sending wireless messages to and from a computer network within the vicinity of person support apparatus 20*g*, and one or more servers and/or wireless routes or wireless access points function as intermediate devices.

Each user interface 60 in person support apparatuses 20*g* is configured to allow a user to configure its corresponding sleep detector 336 such that the sleep detector will transmit the sleep status of the person on its corresponding support surface 28 via transceiver 132 to other support apparatuses 20*g* (either directly or indirectly). This information is used by the sleep detector 336 of a receiving support apparatus 20*e* to control how that person support apparatus 20*g* will control its indicator 330. In other words, person support apparatus 20*g* is not only configured such that indicator 330 is controllable by a user based upon the sleep state of a person supported on its support surface 28, but it is also configured such that indicator 330 is controllable by a user based upon the sleep state of a person supported on the support surface 28 of a nearby person support apparatus 20*g*. In this manner, for example, if person support apparatuses 20*g* are both positioned within the same room, or otherwise in close proximity to each other, and a person on one of the support apparatuses 20*g* is sleeping, the indicators 330 can both be automatically adjusted so as to reduce or eliminate potentially sleep-interfering audio or visual indications. Thus, the sounds or lights of nearby person support apparatuses can be changed so as to reduce the likelihood that they will interfere with the sleep of a nearby person.

User interface 60 of person support apparatus 20*g* is configured to allow a user to control its corresponding indicator 330 so that it will respond to the sleep status of the person on its own support surface 28 differently from how it will respond to the sleep status of a person on a nearby person support apparatus 20*g*. For example, in some cases, it will be desirable to merely reduce (but not eliminate) the sounds or lights on a person support apparatus 20*g* when a nearby person is asleep, but the person on person support apparatus 20*g* itself is awake; and to completely eliminate the sounds or lights when the person on person support apparatus 20*g* itself is asleep. User interface 60 allows a user to implement such a configuration. User interface 60 therefore allows a user to individually configure the action of indicator 330 for each triggering event based on the sleep status of the person on its corresponding support surface 28, and to also individually configure the action of indicator 330 for each triggering event based on the sleep status of one or more nearby persons.

In one embodiment, transceivers 132 communicate directly with each other using any suitable short-range wireless technology, such as, but not limited to, Bluetooth, or any wireless technologies in accordance with IEEE (Institute of Electrical and Electronic Engineers) standard 802.15.1. In such an embodiment, sleep detector 336 deems the reception of a sleep status message from another person support apparatus 20*g* as evidence that the other person support apparatus 20*g* is positioned within close proximity to itself, and will automatically take into account the sleep status of the person on that nearby person support apparatus.

In another embodiment, transceivers 132 are configured to use longer range wireless technology. In this embodiment, transceivers 132 may also send, in addition to the sleep status of the person on their own support surface 28, their location within a facility. Any person support apparatuses 20g that receive this information will determine whether to respond to, or ignore, the contents of the sleep status message from that transmitting person support apparatus based on whether the location of that transmitting person support apparatus is within a threshold proximity to the receiving person support apparatus.

FIG. 28 illustrates another embodiment of a person support apparatus 20h. The components of person support apparatus 20h that are common to those of previously described support apparatuses (e.g. support apparatuses 20-20g) are labeled with common reference numbers and function in the same manner as previously described, and will therefore not be described further. Person support apparatus 20h, like person support apparatus 20g, includes a transceiver 132 that is adapted to wirelessly transmit sleep status messages. However, person support apparatus 20h is also configured to send control signals to one or more remote devices 342, in addition to sending sleep status signals. Such control signals cause the remote device 342 to behave in a different manner based on the sleep status of the person on support apparatus 20h. Alternatively, communication between transceiver 132 and remote device 342 can be carried out through a wire line that is not shown in FIG. 28. Examples of the wire line include twisted pair, shielded cable, optical cable, telephone line, or wired Local Area Network (LAN).

Remote device 342 may be any of a variety of different types of devices, depending upon the particular usage of person support apparatus 20h and its environment. In one embodiment, when person support apparatus 20h is used in a medical facility, remote device 342 is a computer at a caregiver's station. In another embodiment, remote device 342 is a room light, or room light controller, that provides illumination to the room in which person support apparatus 20h is located. In still another embodiment, remote device 342 is an entertainment device, such as a television or radio. In still other embodiments, remote device 342 takes on different forms.

When remote device 342 is a computer in a medical facility, the receipt by remote device 342 of a control signal, or a status signal indicating that the person is asleep, results in the remote device 342 automatically taking one or more actions. For example, in one embodiment, the computer (remote device 342) includes software that manages and tracks patient care tasks. When the computer receives information from a person support apparatus 20h that the person is in a sleep state, the computer automatically changes the scheduling of the one or more patient care tasks so as to reduce or eliminate interruptions to the person's sleep. Such patient care tasks can include any one or more of the following: bathing the person, taking one or more of the person's vital signs, assisting the person to the rest room, administering medication to the person, or any other task that assists the patient in some manner.

The automatic re-scheduling performed by remote device 342—embodied as the computer—defers those patient care tasks that are not time critical until the patient is awake. Further, the computer automatically changes the patient care tasks of those patients who are awake so as to fill in any scheduled tasks that are deferred. Thus, for example, if a nurse is scheduled to bathe patient A after completing a task with patient B, but patient A is currently asleep, the computer will re-arrange his or her schedule so that the next task is taking care of a patient who is currently awake, such as patient C. This deferment of patient A's bath will continue until patient A awakens, or until the amount of sleep experienced by patient A exceeds a user-configurable threshold. Indeed, the computer is, in at least one embodiment, configured such that a user, such as an administrator, can determine how the sleep status of the one or more patients will affect the scheduling and performance of the various medical care tasks.

When remote device 342 is a computer used by caregivers for providing, scheduling, and/or monitoring the care of patients, the computer is also configurable so as to react to a sleep state of an individual patient based upon not only that patient's current sleep state, but also a database containing a record of that patient's past sleep states. Thus, for example, if the records indicate that a particular patient has not had sufficient sleep for an extended period of time, or has not had sleep of a sufficiently high quality for a threshold amount of time, the computer will automatically defer patient care tasks to a greater extent than if the patient had obtained a sufficiently high amount or quality of sleep in the past. Consequently, as another example, the computer will re-schedule non-time-critical patient care tasks for a greater amount of time for a patient who has not slept for 24 hours than for, say, a patient who has had eight hours of restful sleep within the past 24 hours. Still other ways of controlling the scheduling and/or performance of patient care tasks based upon each individual's past sleep history are possible.

When remote device 342 is a computer used by caregivers for providing, scheduling, and/or monitoring the care of patients, the computer is, in at least some embodiments, additionally or alternatively adapted to use one or more algorithms to predict a patient needs or cares in advance based upon that patient's sleep status and their quality of sleep. Further, remote device 342 is adapted to forward this information to one or more caregivers, such as via one or more emails, text messages, or other means. This information is then usable by the recipient caregiver to adjust his or her schedule, diagnosis, and/or treatment so as to improve the quality of the care delivered to that patient.

The prediction of a patient's needs or cares is based not only upon the sleep quality of the patient and his or her past sleep history, but also clinical data that is input into a database accessible to the computer (remote device 342) and that establishes correlations between various health conditions and a person's sleep quality. Still further, the predictive action, in one embodiment, takes into account the current sickness, disease, or other health condition of the patient. Therefore, if a particular patient is experiencing a reduced amount of sleep or a reduced quality of sleep, the computer is adapted to forward to the assigned caregivers one or more messages indicating that this patient may be at risk of developing any one or more health problems that are related to the quality of their recent sleep and their current health condition. The recipient caregiver then has the option of taking appropriate counter measures to help prevent the actual development of the potential health problem.

In addition to, or in lieu of, predicting potential health problems, the computer (remote device 342) is also adapted, in at least one embodiment, to predict that a patient may be in need of an imminent trip to the rest room based upon the recent sleep history of that patient. Thus, for example, a patient who has been asleep for longer than a threshold amount of time and who has either awoken, or is in the awakening state, will likely need to make a trip to the rest room soon. The computer is configurable by a user to send a message to the corresponding caregiver when this situation is detected so that the caregiver has the option of changing his or her schedule to assist that patient to the rest room, if desired. In this manner, a caregiver can arrive at a patient's room at or about the time a patient's rest room trip is imminent, thereby reducing the risk of a patient fall when the patient exits the person support apparatus.

FIG. 20 illustrates one manner in which one or more indicators 330 may be incorporated into patient support apparatus 20c. Indicator 30a is a speaker positioned inside of one of siderails 68. Indicator 30b is a light positioned on footboard 32. Both of these indicators 30a and 30b are in electrical communication with controller 56 and are controllable in different manners by controllers 56 based upon the sleep status of a person on person the support apparatus. Other indicators besides the two labeled 30a and 30b may also be present, including additional speakers, one or more buzzers or beepers, and one or more other lights.

Although not shown in FIG. 20, person support apparatus 20c is constructed to include, in at least one embodiment, transceiver 132 for communicating with one or more other person support apparatuses and/or for communicating with one or more remote devices 342. Person support apparatus 20c can therefore control its indicators 30a and 30b based on the sleep status of nearby persons, as well as the person on its own support surface 28, as well as controlling the operation of one or more remote devices 342 based on the sleep status of the person on its own support surface 28.

Figure 29A:
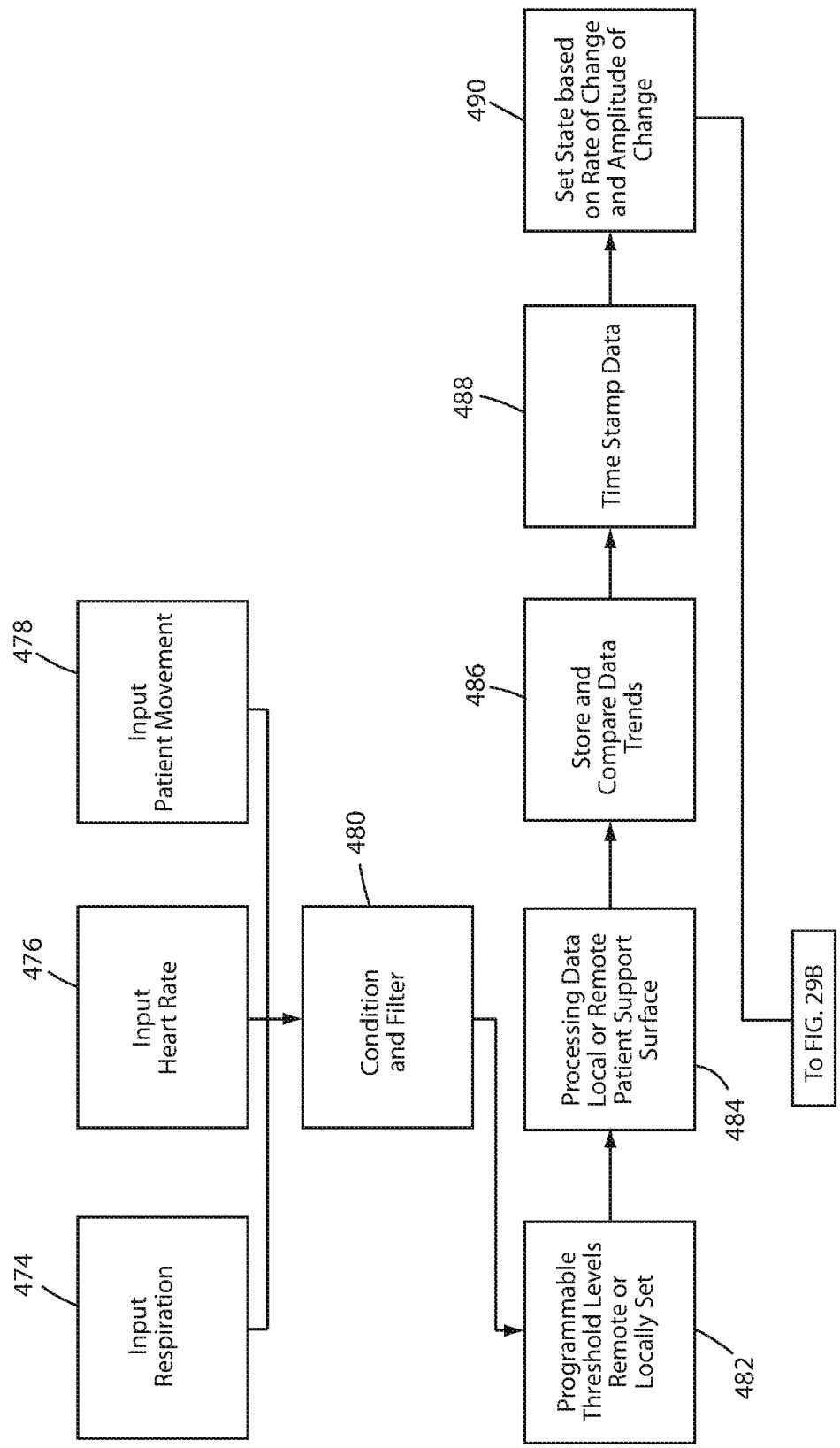
FIG. 29a is a flow diagram of a method of configuring an environment according to yet another embodiment that may be utilized with any one or more of the person support apparatuses disclosed herein.
Figure 29B:
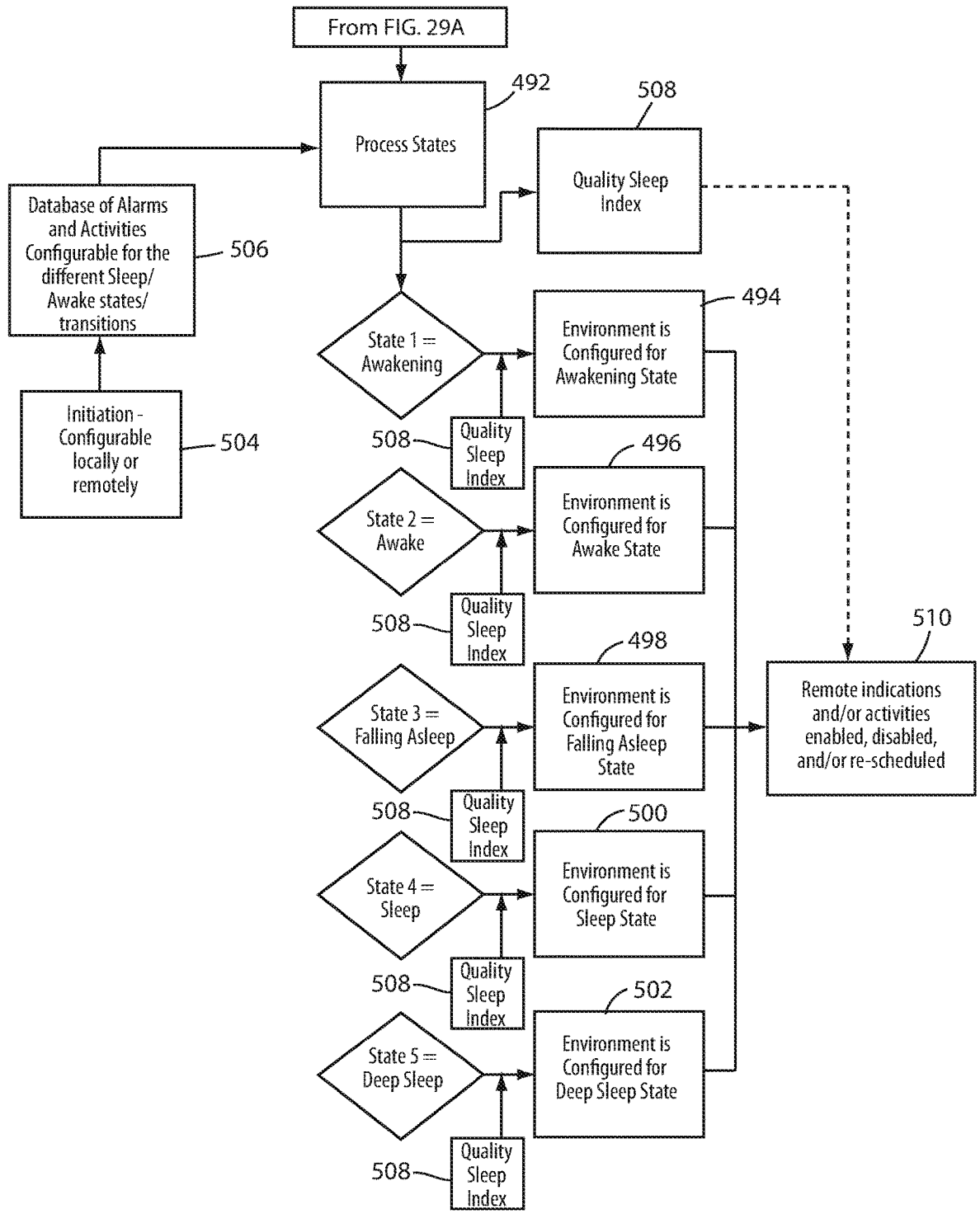

FIGS. 29a and 29b collectively illustrate one embodiment of a control method 372 that is followed by a user or institution using any one or more of the person support apparatuses 20e-20h. Many of the steps of control method 372 are carried out by controller 56, although, as will be apparent from the discussion below, any one or more of these steps may alternatively be carried out by one or more computers that are positioned remotely from the person support apparatus.

Method 372 receives a respiration rate input at step 474, a heart rate input at step 476, and a patient movement input at step 478. Inputs 474 and 476 are generated from one or more vital sign sensors 134 and/or one or more sleep detectors 336. Input 478 is generated from any sensor or sensors that are suitable for monitoring patient movement, such as, but not limited to, the weight distribution sensors (e.g. load cells) and/or video cameras mentioned above. This information is conditioned and filtered at step 480 by controller 56 to remove noise and/or extraneous signals and to place the inputs in a form that is more easily utilized by controller 56 or other computers involved in the processing of the signals received at steps 474, 476, or 478.

At step 482, controller 56, or a remote computer, receives user-configurable data regarding one or more threshold levels that are used in the determination of the sleep status of a person. Step 482 allows a user, such as a hospital administrator or the like, to control how many different sleep states a person's sleep status will be classified into, as well as the threshold criteria that are used for defining each of those sleep states. The number and definitions of the various sleep states are therefore user-configurable.

At step 484, the data received at steps 474, 476, and 478, which is filtered and conditioned at step 480, is processed, either locally by controller 56, or remotely by one or more remote computers. After this data is processed, the data is stored and compared to prior data at step 486. The prior data is data that has been gathered and recorded for the particular person currently on the person support apparatus. At step 488 the most recent data that has been received at steps 474, 476, and 478 is time stamped such that it is usable for determining the current sleep status of the patient, as well as for being added to the database for use in determining future sleep states.

At step 490, the sleep state of the person is determined based upon the comparison of the current vital sign and movement data with past vital sign and movement data. Such a determination includes comparing the rate of change and the amplitude of changes in the vital sign information and movement information. Further, this determination utilizes the thresholds and classifications that were input at step 482.

At step 492 (FIG. 29b), controller 56—or a remote computer—identifies the current sleep state of the person as one of five different states 1, 2, 3, 4, or 5, corresponding to awakening, awake, asleep, sleep, and falling asleep. Although FIGS. 29a and 29b show that the sleep states are categorized into these specific five states, it will be understood by those skilled in the art that a smaller or greater number of sleep states could be utilized, if desired. After identifying the current sleep state, controller 56 proceeds to one of steps 494, 496, 498, 500, or 502, depending upon which sleep state the person is currently in. At steps 494, 496, 498, 500, and 502, controller 56 configures the person support apparatus and/or the local environment in a manner corresponding to the current particular sleep state of the person (e.g. such as by muting one or more sounds or lights from one or more indicators 330, by sending control signals or status signals to another person support apparatus or a remote device, or by other means).

The specific actions that controller 56 takes in each of steps 494-502 is based upon information that is input in steps 504 and 506. At step 504, initial information is input into controller 56, or a computer in electronic communication with controller 56, by a user that is specific to the person who is to be supported on the person support apparatus. In a medical setting, this information may include information as to whether the person is a light sleeper, a deep sleeper, easily awoken by sounds and/or lights, and/or any other information regarding the sleep habits or characteristics of the person who will be utilizing the person support apparatus.

After the person-specific information is input at step 504, additional configuration data is input at step 506, either locally via user interface 60 or remotely via a computer that is in communication with the person support apparatus. The additional information that is input at step 506 includes all of the desired manners in which the action of indicator(s) 330 will be changed based upon the current sleep status, as well as all of the different triggering events for which those changed actions will apply. In other words, step 506 enables a user to dictate how the person support apparatus will react to each triggering event when the person is in each of the different sleep states. Step 506 also allows the user to control how the person support apparatus will react to each triggering event when a person positioned on a nearby person support apparatus is asleep. As was noted above, this reaction is configurable by the user-if desired—to be different than the reaction implemented when it is the person on that person support apparatus who is asleep, as opposed to a nearby person.

After the sleep state of the person has been identified at step 492, a quality sleep index is optionally generated at step 508. This sleep index provides an assessment of the quality of the person's recent past sleep. This enables the person support apparatus and/or the local environment of the person support apparatus to be configured differently depending upon the value of the sleep index. Thus, for example, if the person has recently experienced sleep of poor quality, the configuration actions taken at any of steps 494-502 will be changed so as to reduce the potential for interruptions of the person's sleep beyond what actions would otherwise have been taken had the person experienced higher quality sleep in the recent past. Conversely, the actions taken in steps 494-502 allow for greater potential interruptions of the person's sleep if the person has experienced a threshold amount of high quality sleep in the past.

Using the determination of the sleep state, the information input at steps 504 and 506, as well as the quality sleep index, controller 56 configures the person support apparatus and/or the local environment in the appropriate manner at the one of steps 494-502 that corresponds to the current sleep state. This configuration takes on any of the forms previously mentioned (e.g. muting alarms, reducing the volume of sounds, changing sound notifications to visual notifications, reducing or eliminating visual notifications, etc.). After these steps are taken, control passes to step 510, where one or more appropriate steps are taken remotely based on the sleep status of the person. As was noted above, such remote steps include having a remote device 342 take one or more actions in response to the person's sleep status. When remote device 342 is a computer, the computer is adapted to re-schedule one or more tasks; enable, disable, and/or defer one or more alerts or indications, inform one or more caregivers of the patient's sleep status, issue one or more predictive messages regarding potential health complications that the patient may be at risk of developing based on their sleep history, and/or take other steps. In one embodiment, the actions taken remotely in step 510 are also partially based upon the quality sleep index of step 508, while in another embodiment, these actions taken remotely in step 510 are not based on the quality sleep index of step 508.

After step 510, method 372 begins again and the current sleep status of the person is determined. If the sleep status changes, appropriate changes are made to the person support apparatus, its environment, and/or to one or more remote devices 342. Continuous monitoring of the person's sleep status is therefore provided and adjustments are automatically made based upon changes in that person's sleep status. Further, the continuous monitoring of the person's sleep status provides data for storing baseline information about that patient, as well as data for determining the quality sleep index at step 508.

It will be understood by those skilled in the art that various modifications can be made to the embodiments described herein. For example, instead of using load cells 36, other types of force sensors may be used in any of the measurement subsystems 54, 54*a*, and/or 54*b*. Still further, it will be understood that variations to the layout, content, and sequencing of the screen shots that have been described herein may be made. As one example, in addition to the information displayed thereon discussed above, any of the screen shots can be modified to include additional menu items that enable the caregiver to control other aspects of the patient support apparatus, such as, but not limited to, raising and lowering the height of the patient support surface 28, pivoting one or more sections of the patient support surface 28, turning on and off a brake, setting and/or editing one or more protocol alert timers, configuring a patient exit alert system, and/or other features. In one embodiment, touch screen display 64 includes the same or similar functionalities and screen images shown on the footboard display of the InTouch critical care bed manufactured by Stryker Corporation of Kalamazoo, Mich. Such functionalities and images are described in more detail in the InTouch Critical Care Bed Model FL27 Operations Manual published in 2012 (2131-409-001-Rev B), which is available from Stryker Corporation of Kalamazoo, Mich. and which is incorporated herein by reference in its entirety.

Still other alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:

1. A patient support apparatus comprising:

a base;

a frame supported on the base;

a support surface adapted to support a patient thereon;

a plurality of force sensors coupled to the frame and adapted to output signals corresponding to downward forces exerted on the support surface;

a display coupled to the patient support apparatus; and a controller in communication with the plurality of force sensors and the display, the controller adapted to perform the following:

(a) determine a weight of the patient supported on the support surface based on the signals from the plurality of force sensors;

(b) automatically monitor the signals from the plurality of force sensors while the patient is supported on the support surface and determine if an object has been added to the support surface or removed from the support surface by continuously monitoring a change in weight detected by the plurality of force sensors, comparing the change to a threshold, and concluding the weight change is due to the object being added or removed if the weight change is less than the threshold; and (c) display on the display the weight of the patient and, if the object has been added to or removed from the support surface, a weight of the object.

2. The patient support apparatus of claim 1 wherein the controller is further adapted to conclude the weight change is due to the patient entering or exiting if the weight change is greater than the threshold.

3. The patient support apparatus of claim 1 wherein the controller is further adapted to maintain a weight log of objects added to the support surface, and to add the weight of the object to the weight log if the controller determines that the object has been added to the support surface.

4. The patient support apparatus of claim 3 wherein the controller is further adapted to display a weight log icon on the display.

5. The patient support apparatus of claim 4 wherein the controller displays additional information about the weight log when a user touches the weight log icon.

6. The patient support apparatus of claim 3 wherein the controller is adapted to automatically add the weight of the object to the weight log if the controller determines that the object has been added to the support surface.

7. The patient support apparatus of claim 1 wherein the controller is further adapted to simultaneously display the weight of the patient and the weight of the object.

8. The patient support apparatus of claim 1 further comprising:
a transceiver adapted to communicate with a server remote from the patient support apparatus;
wherein the controller is, in addition, a part of an exit alert system adapted to issue an exit alert if the patient on the support surface exits from the patient support apparatus while the exit alert system is armed, the exit alert system including the plurality of force sensors; and
wherein the controller is further adapted to record the signals from the force sensors during a time period when the patient exits the support surface and to transmit the recorded signals to the remote server.

9. The patient support apparatus of claim 8 wherein the controller is adapted to transmit the recorded signals to the remote server wirelessly using WiFi.

10. The patient support apparatus of claim 8 wherein the controller is adapted to record the signals from the force sensors both prior to, and during, the patient exit, and the controller is adapted to transmit to the remote server the recorded signals from both prior to, and during, the patient exit.

11. The patient support apparatus of claim 8 wherein the plurality of force sensors are load cells adapted to measure the weight of the patient positioned on the support surface.

12. The patient support apparatus of claim 8 wherein the controller is further adapted to receive instructions from the remote server to modify the exit alert system in a manner that is based at least partially upon the recorded signals transmitted to the remote server.

13. A patient support apparatus comprising:
a base;
a frame supported on the base;
a support surface adapted to support a patient thereon;
a plurality of force sensors coupled to the frame and adapted to output signals corresponding to downward forces exerted on the support surface;
a display coupled to the patient support apparatus; and
a controller in communication with the plurality of force sensors and the display, the controller adapted to perform the following:
(a) determine a weight of the patient supported on the support surface based on the signals from the plurality of force sensors;
(b) automatically monitor the signals from the plurality of force sensors while the patient is supported on the support surface and determine if an object has been added to the support surface or removed from the support surface by measuring a speed at which a weight change occurs, comparing the speed to a threshold, concluding the weight change is due to the object if the speed exceeds the threshold, and concluding the weight change is not due to the object if the speed does not exceed the threshold; and
(c) display on the display the weight of the patient and, if the object has been added to or removed from the support surface, a weight of the object.

14. The patient support apparatus of claim 13
wherein the controller is, in addition, a part of an exit alert system adapted to issue an alert if the patient on the support surface exits the patient support apparatus while the exit alert system is armed; and
wherein the controller is further adapted to record a time when the patient positioned on the support surface exits the support surface, regardless of whether the exit alert system is armed or not.

15. The patient support apparatus of claim 14 wherein the controller is further adapted to display the time when the patient positioned on the support surface exited the patient support apparatus.

16. The patient support apparatus of claim 14 wherein the controller is further adapted to record how long the patient remains off of the support surface after exiting the support surface.

17. The patient support apparatus of claim 14 wherein the exit alert system includes the plurality of force sensors, and the plurality of force sensors comprise a plurality of load cells adapted to detect the downward forces exerted on the support surface.

18. The patient support apparatus of claim 17 wherein the controller is adapted to record the signals of the load cells prior to, and during, exiting of the patient from the support surface.

19. The patient support apparatus of claim 18 wherein the controller is further adapted to analyze the recorded signals for any patterns, to use any discovered patterns to analyze future signals of the load cells in order to predict when a different patient may be about to exit the patient support apparatus.

20. The patient support apparatus of claim 19 wherein the controller is adapted to forward the recorded signals of the load cells to a server located remotely from the patient support apparatus for analysis.

* * * * *